United States Patent
Gonzalez et al.

(10) Patent No.: US 11,913,049 B2
(45) Date of Patent: Feb. 27, 2024

(54) BIOCONVERSION OF SHORT-CHAIN HYDROCARBONS TO FUELS AND CHEMICALS

(71) Applicants: Ramon Gonzalez, Friendswood, TX (US); James Clomburg, Houston, TX (US); Alexander Chou, Houston, TX (US)

(72) Inventors: Ramon Gonzalez, Friendswood, TX (US); James Clomburg, Houston, TX (US); Alexander Chou, Houston, TX (US)

(73) Assignee: Ramon Gonzalez, Tampa, FL (US)

( * ) Notice: Subject to any disclaimer, the term of this patent is extended or adjusted under 35 U.S.C. 154(b) by 580 days.

(21) Appl. No.: 16/878,032

(22) Filed: May 19, 2020

(65) Prior Publication Data
US 2020/0347423 A1 Nov. 5, 2020

Related U.S. Application Data

(63) Continuation of application No. 15/562,606, filed as application No. PCT/US2016/025103 on Mar. 31, 2016, now abandoned.

(51) Int. Cl.
*C12N 9/00* (2006.01)
*C12P 19/32* (2006.01)
(Continued)

(52) U.S. Cl.
CPC ........ *C12P 19/32* (2013.01); *C12N 9/00* (2013.01); *C12N 9/001* (2013.01); *C12N 9/0006* (2013.01); *C12N 9/0008* (2013.01); *C12N 9/0077* (2013.01); *C12N 9/13* (2013.01); *C12N 9/88* (2013.01); *C12N 9/90* (2013.01); *C12N 9/93* (2013.01); *C12P 5/02* (2013.01); *C12P 5/026* (2013.01); *C12P 7/02* (2013.01); *C12P 7/24* (2013.01); *C12P 7/40* (2013.01); *C12P 7/42* (2013.01); *C12P 7/46* (2013.01); *C12P 7/625* (2013.01); *C12P 9/00* (2013.01); *C12P 13/001* (2013.01); *C12P 13/04* (2013.01); *C12Y 101/01* (2013.01); *C12Y 101/03039* (2013.01); *C12Y 102/01* (2013.01); *C12Y 102/04001* (2013.01); *C12Y 103/05001* (2013.01); *C12Y 103/99* (2013.01); *C12Y 108/01004* (2013.01); *C12Y 114/15003* (2013.01); *C12Y 203/01012* (2013.01); *C12Y 203/01054* (2013.01); *C12Y 207/01031* (2013.01); *C12Y 208/03* (2013.01); *C12Y 401/00* (2013.01);
(Continued)

(58) Field of Classification Search
CPC .. C12P 19/32; C12P 5/02; C12P 5/026; C12P 7/02; C12P 7/24; C12P 7/40; C12P 7/42; C12P 7/46; C12P 9/00; C12P 13/001; C12P 13/04; C12N 9/0006; C12N 9/0008; C12N 9/001; C12N 9/0077; C12N 9/13; C12N 9/88; C12N 9/90; C12N 9/93; C12Y 101/01; C12Y 101/03039; C12Y 102/01; C12Y 102/04001; C12Y 103/05001; C12Y 103/99; C12Y 108/01004; C12Y 114/15003; C12Y 203/01012; C12Y 203/01054; C12Y 207/01031; C12Y 208/03; C12Y 401/00; C12Y 401/01; C12Y 401/01047; C12Y 401/03024; C12Y 402/01; C12Y 402/01002; C12Y 402/01011; C12Y 501/99001; C12Y 501/99002; C12Y 504/02; C12Y 504/99; C12Y 504/99001; C12Y 504/99002; C12Y 602/01; C12Y 602/01005; C12Y 604/01003; Y02E 50/30
See application file for complete search history.

(56) References Cited

U.S. PATENT DOCUMENTS

2010/0035309 A1* 2/2010 Havemen et al. ............. 435/19
2013/0316413 A1 11/2013 Gonzalez et al.
(Continued)

OTHER PUBLICATIONS

Kniemeyer et al., "Anaerobic oxidation of short-chain hydrocarbons by marine sulphate-reducing bacteria", Nature letters, vol. 449, (Oct. 18, 2007; doi:10.1038/nature06200), pp. 899-902. (Year: 2007).*
(Continued)

*Primary Examiner* — Satyendra K Singh
(74) *Attorney, Agent, or Firm* — Elmore Patent Law Group, P.C.; Mahreen Chaudhry Hoda; Carolyn S. Elmore

(57) ABSTRACT

An engineered microorganism(s) with novel pathways for the conversion of short-chain hydrocarbons to fuels and chemicals (e.g. carboxylic acids, alcohols, hydrocarbons, and their alpha-, beta-, and omega-functionalized derivatives) is described. Key to this approach is the use of hydrocarbon activation enzymes able to overcome the high stability and low reactivity of hydrocarbon compounds through the cleavage of an inert C—H bond. Oxygen-dependent or oxygen-independent activation enzymes can be exploited for this purpose, which when combined with appropriate pathways for the conversion of activated hydrocarbons to key metabolic intermediates, enables the generation of product precursors that can subsequently be converted to desired compounds through established pathways. These novel engineered microorganism(s) provide a route for the production of fuels and chemicals from short chain hydrocarbons such as methane, ethane, propane, butane, and pentane.

13 Claims, 33 Drawing Sheets

Related U.S. Application Data

(60) Provisional application No. 62/140,628, filed on Mar. 31, 2015.

(51) Int. Cl.

| | | |
|---|---|---|
| *C12P 7/02* | (2006.01) | |
| *C12P 7/24* | (2006.01) | |
| *C12P 7/40* | (2006.01) | |
| *C12P 7/46* | (2006.01) | |
| *C12N 9/04* | (2006.01) | |
| *C12N 9/02* | (2006.01) | |
| *C12P 7/625* | (2022.01) | |
| *C12N 9/10* | (2006.01) | |
| *C12N 9/88* | (2006.01) | |
| *C12N 9/90* | (2006.01) | |
| *C12P 5/02* | (2006.01) | |
| *C12P 7/42* | (2006.01) | |
| *C12P 9/00* | (2006.01) | |
| *C12P 13/00* | (2006.01) | |
| *C12P 13/04* | (2006.01) | |

(52) U.S. Cl.
CPC ..... *C12Y 401/01* (2013.01); *C12Y 401/01047* (2013.01); *C12Y 401/03024* (2013.01); *C12Y 402/01* (2013.01); *C12Y 402/01002* (2013.01); *C12Y 402/01011* (2013.01); *C12Y 501/99001* (2013.01); *C12Y 501/99002* (2013.01); *C12Y 504/02* (2013.01); *C12Y 504/99* (2013.01); *C12Y 504/99001* (2013.01); *C12Y 504/99002* (2013.01); *C12Y 602/01* (2013.01); *C12Y 602/01005* (2013.01); *C12Y 604/01003* (2013.01); *Y02E 50/30* (2013.01)

(56) References Cited

U.S. PATENT DOCUMENTS

2014/0256904 A1  9/2014  Schaffer et al.
2014/0273110 A1  9/2014  Gonzalez et al.

OTHER PUBLICATIONS

Callaghan, A. V. et al., "Enzymes involved in the anaerobic oxidation of n-alkanes: from methane to long-chain paraffins", Frontiers in Microbiology, 4, 2013, 89.

Mueller, T. et al., "Methane oxidation by anaerobic archaea for conversion to liquid fuels", Journal of Industrial Microbiology & Biotechnology, 42(3), Epub Nov. 27, 2014, 2015, 391-401.

Musat, F., "The anaerobic degradation of gaseous, nonmethane alkanes—From in situ processes to microorganisms", Computational and Structural Biotechnology Journal, 13, Mar. 19, 2015, 222-228.

Wilkes, "Anaerobic Degradation of N-Hexane in a Denitrifying Bacterium: Further Degradation of the Initial Intermediate (1-methlypentyl) succinate Via C-Skeleton Rearrangement", Arch Microbiol., vol. 177, Dec. 2001, 235-243.

Miralles-Ferrer, et al., "Bacterial Cell Factories for Recombinant Protein Production; Expanding the Catalogue," Microbial Cell Factories, 12:113, pp. 1-4 (2013).

Nakashima, N., et al., "Actinomycetes as Host Cells for Production of Recombinant Proteins," Microbial Cell Factories, 4:7, pp. 1-5 (2005).

* cited by examiner

| TABLE G |
|---|
| A genetically engineered microorganism being a bacteria comprising one or more expression vectors or integrated sequences encoding overexpressed 1) alkane monooxygenase or alkane hydroxylase (EC 1.14.15.3), 2) alcohol dehydrogenase (EC 1.1.1.-), 3) aldehyde dehydrogenase (EC 1.2.1.-), and 4) acyl-CoA synthetase (EC 6.2.1.-); wherein said bacteria is able to convert a short chain alkane (C1-C5, preferably a C1-C4, or C1), to an acyl-CoA. |
| A genetically engineered microorganism being a bacteria comprising one or more expression vectors or integrated sequences encoding overexpressed 1) alkyl succinate synthase (EC 4.1.-), 2) succinyl-CoA:2-methyl-alkyl-succinyl-CoA transferase (EC 2.8.3.-) or 2-methyl-alkyl-succinyl-CoA synthetase (EC 6.2.1.-), 3) 2-methyl-alkyl-malonyl-CoA mutase (EC 5.4.99.-), 4) 2-methyl-alkyl-malonyl-CoA decarboxylase (EC 4.1.1.-), 5) propionyl-CoA carboxylase (EC 6.4.1.3), 6) methylmalonyl-CoA epimerase (EC 5.1.99.1), 7) methylmalonyl-CoA mutase (EC 5.1.99.2), 8) succinyl-CoA:2-methyl-alkyl-succinyl-CoA transferase (EC 2.8.3.-) or succinyl-CoA synthetase (EC 6.2.1.5), and 9) succinate dehydrogenase (EC 1.3.5.1), wherein said bacteria is able to convert a short chain alkane (C1-C5, preferably a C1-C4, or C1), to an acyl-CoA through fumarate addition to said short chain alkane and subsequent regeneration of said fumarate. |
| A genetically engineered microorganism being a bacteria comprising one or more expression vectors or integrated sequences encoding overexpressed 1) methyl succinate synthase (EC 4.1.-), 2) succinyl-CoA:2-methyl-alkyl-succinyl-CoA transferase (EC 2.8.3.-) or 2-methyl-alkyl-succinyl-CoA synthetase (EC 6.2.1.-), 3) 2-methyl-succinyl-CoA dehydrogenase (EC 1.3.99.-), 4) mesaconyl-C1-CoA-C4-CoA transferase (EC 2.8.3.-), 5) mesaconyl-C4-CoA hydratase (EC 4.2.1.153), 6) L-malyl-CoA/citramalyl-CoA lyase (EC 4.1.3.25), 7) pyruvic-malic carboxylase (EC 1.1.1.39), and 8) fumarase (EC 4.2.1.2), wherein said bacteria is able to convert methane to an acyl-coA through fumarate addition to said methane and subsequent regeneration of said fumarate. |
| A genetically engineered microorganism being a bacteria comprising one or more expression vectors encoding overexpressed 1) methyl succinate synthase (EC 4.1.-), 2) succinyl-CoA:2-methyl-alkyl-succinyl-CoA transferase (EC 2.8.3.-) or 2-methyl-alkyl-succinyl-CoA synthetase (EC 6.2.1.-), 3) 2-methyl-alkyl-succinyl-CoA dehydrogenase (EC 1.3.99.-), 4) mesaconyl-CoA hydratase/β-methylmalyl-CoA dehydratase (EC 4.2.1.148), 5) β-methylmalyl-CoA lyase (EC 4.1.3.24), 6) propionyl-CoA carboxylase (EC 6.4.1.3), 7) methylmalonyl-CoA epimerase (EC 5.1.99.1) and methylmalonyl-CoA mutase (EC 5.1.99.2), 8) succinyl-CoA:2-methyl-alkyl-succinyl-CoA transferase (EC 2.8.3.-) or succinyl-CoA synthetase (EC 6.2.1.5), 9) succinate dehydrogenase (EC 1.3.5.1), 10: glyoxylate carboligase (EC 4.1.1.47), 11) tartronate semialdehyde reductase (EC 1.1.1.60), 12) glycerate kinase (EC 2.7.1.31), 13:) glycolytic enzymes (phosphoglycerate mutase (EC 5.4.2.11), enolase (EC 4.2.1.11), pyruvate kinase (EC 2.7.1.40)), and 14) pyruvate dehydrogenase complex (EC 1.2.4.1, EC 2.3.1.12, EC 1.8.1.4) or pyruvate formate lyase (EC 2.3.1.54), wherein said bacteria is able to convert methane to an acyl-coA through fumarate addition to said methane and subsequent regeneration of said fumarate. |
| A genetically engineered microorganism being a bacteria being $E.\ coli$ and comprising one or more expression vectors or integrated sequences encoding overexpressed 1) alkane monooxygenase or alkane hydroxylase (EC 1.14.15.3), 2) alcohol dehydrogenase (EC 1.1.1.-), 3) aldehyde dehydrogenase (EC 1.2.1.-), and 4) acyl-CoA synthetase (EC 6.2.1.-); wherein said bacteria is able to convert a short chain alkane (C1-C5) to an acyl-CoA. |
| A genetically engineered microorganism being a bacteria being $E.\ coli$ and comprising one or more expression vectors or integrated sequences encoding overexpressed 1) alkyl succinate synthase (EC 4.1.-), 2) succinyl-CoA:2-methyl-alkyl-succinyl-CoA transferase (EC 2.8.3.-) or 2-methyl-alkyl-succinyl-CoA synthetase (EC 6.2.1.-), 3) 2-methyl-alkyl-malonyl-CoA mutase (EC 5.4.99.-), 4) 2-methyl-alkyl-malonyl-CoA decarboxylase (EC 4.1.1.-), 5) propionyl-CoA carboxylase (EC 6.4.1.3), 6) methylmalonyl-CoA epimerase (EC 5.1.99.1), 7) methylmalonyl-CoA mutase (EC 5.1.99.2), 8) succinyl-CoA:2-methyl-alkyl-succinyl-CoA transferase (EC 2.8.3.-) or succinyl-CoA synthetase (EC 6.2.1.5), and 9) succinate dehydrogenase (EC 1.3.5.1), wherein said bacteria is able to converts a short chain alkane (C1-C5) to an acyl-CoA through fumarate addition to said short chain alkane and subsequent regeneration of said fumarate. |
| A genetically engineered microorganism being a bacteria being $E.\ coli$ and comprising one or more expression vectors or integrated sequences encoding overexpressed 1) methyl succinate synthase (EC 4.1.-), 2) succinyl-CoA:2-methyl-alkyl-succinyl-CoA transferase (EC 2.8.3.-) or 2-methyl-alkyl-succinyl-CoA synthetase (EC 6.2.1.-), 3) 2-methyl-succinyl-CoA dehydrogenase (EC 1.3.99.-), 4) mesaconyl-C1-CoA-C4-CoA transferase (EC 2.8.3.-), 5) mesaconyl-C4-CoA hydratase (EC 4.2.1.153), 6) L-malyl-CoA/citramalyl-CoA lyase (EC 4.1.3.25), 7) pyruvic-malic carboxylase (EC 1.1.1.39), and 8) fumarase (EC 4.2.1.2), wherein said bacteria is able to convert methane to an acyl-coA through fumarate addition to said methane and subsequent regeneration of said fumarate. |
| A genetically engineered microorganism being a bacteria being $E.\ coli$ and comprising one or more expression vectors or integrated sequences encoding overexpressed 1) methyl succinate synthase (EC 4.1.-), 2) succinyl-CoA:2-methyl-alkyl-succinyl-CoA transferase (EC 2.8.3.-) or 2-methyl-alkyl-succinyl-CoA synthetase (EC 6.2.1.-), 3) 2-methyl-alkyl-succinyl-CoA dehydrogenase (EC 1.3.99.-), 4) mesaconyl-CoA hydratase/β-methylmalyl-CoA dehydratase (EC 4.2.1.148), 5) β-methylmalyl-CoA lyase (EC 4.1.3.24), 6) propionyl-CoA carboxylase (EC 6.4.1.3), 7) methylmalonyl-CoA epimerase (EC 5.1.99.1) and methylmalonyl-CoA mutase (EC 5.1.99.2), 8) succinyl-CoA:2-methyl-alkyl-succinyl-CoA transferase (EC 2.8.3.-) |

FIG. 15

| TABLE G |
|---|
| or succinyl-CoA synthetase (EC 6.2.1.5), 9) succinate dehydrogenase (EC 1.3.5.1), 10: glyoxylate carboligase (EC 4.1.1.47), 11) tartronate semialdehyde reductase (EC 1.1.1.60), 12) glycerate kinase (EC 2.7.1.31), 13:) glycolytic enzymes (phosphoglycerate mutase (EC 5.4.2.11), enolase (EC 4.2.1.11), pyruvate kinase (EC 2.7.1.40)), and 14) pyruvate dehydrogenase complex (EC 1.2.4.1, EC 2.3.1.12, EC 1.8.1.4) or pyruvate formate lyase (EC 2.3.1.54), wherein said bacteria is able to convert methane to an acyl-coA through fumarate addition to said methane and subsequent regeneration of said fumarate. |
| A genetically engineered microorganism converting a short-chain (C1-C5) alkane substrate to a product, said microorganism comprising enzymes or overexpressed enzymes or genes encoding same for : <br> a sequence of reactions for the oxygen-independent activation of a short-chain (C1-C5) alkane via fumarate addition to a 2-methyl-alkyl-succinate and subsequent conversion of said 2-methyl-alkyl-succinate to an acyl-CoA; <br> a sequence of reactions for the generation of product precursor acetyl-CoA and an acyl-CoA or keto-acid from said acyl-CoA; <br> a sequence of reactions for the regeneration of fumarate through the conversion of said acyl-CoA or keto-acid to fumarate; <br> a sequence of reactions for the formation of a desired product from said acetyl-CoA intermediate. |
| A genetically engineered microorganism converting a short-chain (C1-C5) alkane substrate to a product, said microorganism comprising enzymes or overexpressed enzymes or genes encoding same for: <br> a sequence of reactions for the oxygen-dependent activation of a short-chain (C1-C5) alkane to a primary alcohol via terminal addition of a hydroxyl group and subsequent conversion of said alcohol to an acyl-CoA; <br> a sequence of reactions for the generation of product precursor acetyl-CoA from said acyl-CoA; <br> a sequence of reactions for the formation of a desired product from said acetyl-CoA intermediate. |
| Any microorganism herein described, where said expression vectors are inducible expression vectors or said integrated sequences are inducible integrated sequences. |
| Any microorganism herein described, wherein said pathway for the oxygen-independent activation and conversion to an acyl-CoA comprises: <br> an overexpressed alkyl succinate synthase that catalyzes the addition of fumarate to a short-chain (C1-C5) alkane to produce a 2-methyl-alkyl-succinate; <br> an overexpressed succinyl-CoA:2-methyl-alkyl-succinyl-CoA transferase or 2-methyl-alkyl-succinyl-CoA synthetase that catalyzes the conversion of said 2-methyl-alkyl-succinate to a 2-methyl-alkyl-succinyl-CoA; <br> an overexpressed 2-methyl-alkyl-malonyl-CoA mutase that catalyzes the isomerization of said 2-methyl-alkyl-succinyl-CoA to a 2-methyl-alkyl-malonyl-CoA; <br> an overexpressed 2-methyl-alkyl-malonyl-CoA decarboxylase that catalyzes the decarboxylation of said 2-methyl-alkyl-malonyl-CoA to an acyl-CoA; |
| Any microorganism herein described, wherein said pathways for the oxygen-independent activation and conversion to an acyl-CoA and generation of product precursor acetyl-CoA and an acyl-CoA or keto-acid comprises: <br> an overexpressed alkyl succinate synthase that catalyzes the addition of fumarate to a short-chain (C1-C5) alkane to produce a 2-methyl-alkyl-succinate; <br> an overexpressed 2-methyl-alkyl-succinyl-CoA synthetase that catalyzes the conversion of said 2-methyl-alkyl-succinate to a 2-methyl-alkyl-succinyl-CoA; <br> an overexpressed 2-methyl-alkyl-succinyl-CoA dehydrogenase that catalyzes the conversion of said 2-methyl-alkyl-succinyl-CoA to 2-methyl-alkyl-2-butenoyl-CoA; <br> an overexpressed mesaconyl-C1-CoA-C4-CoA transferase that catalyzes the conversion of said 2-methyl-alkyl-2-butenoyl-CoA to 3-methyl-alkyl-2-butenoyl-CoA; <br> an overexpressed mesaconyl-C4-CoA hydratase that catalyzes the conversion of said 3-methyl-alkyl-2-butenoyl-CoA to 3-methyl-alkyl-3-hydroxy-succinyl-CoA; <br> an overexpressed citramalyl-CoA lyase that catalyzes the conversion of said 3-methyl-alkyl-3-hydroxy-succinyl-CoA to acetyl-CoA and a keto-acid; |

FIG. 15 cont.

| TABLE G |
|---|
| Any microorganism herein described, wherein said pathways for the oxygen-independent activation and conversion to an acyl-CoA and generation of product precursor acetyl-CoA and an acyl-CoA or keto-acid comprises:<br>an overexpressed alkyl succinate synthase that catalyzes the addition of fumarate to a short-chain (C1-C5) alkane to produce a 2-methyl-alkyl-succinate;<br>an overexpressed succinyl-CoA:2-methyl-alkyl-succinyl-CoA transferase or 2-methyl-alkyl-succinyl-CoA synthetase that catalyzes the conversion of said 2-methyl-alkyl-succinate to a 2-methyl-alkyl-succinyl-CoA;<br>an overexpressed 2-methyl-alkyl-succinyl-CoA dehydrogenase that catalyzes the conversion of said 2-methyl-alkyl-succinyl-CoA to 2-methyl-alkyl-2-butenoyl-CoA;<br>an overexpressed mesaconyl-CoA hydratase/β-methylmalyl-CoA dehydratase that catalyzes the conversion of said 2-methyl-alkyl-2-butenoyl-CoA to 3-hydroxy-2-methyl-alkyl-succinyl-CoA;<br>an overexpressed β-methylmalyl-CoA lyase that catalyzes the conversion of said 3-hydroxy-2-methyl-alkyl-succinyl-CoA to glyoxylate and an acyl-CoA;<br>an overexpressed glyoxylate carboligase that catalyzes the conversion of said glyoxylate to tartronate semialdehyde;<br>an overexpressed tartronate semialdehyde reductase that catalyzes the conversion of said tartronate semialdehyde to D-glycerate;<br>an overexpressed glycerate kinase that catalyzes the conversion of said D-glycerate to 3-phospho-D-glycerate;<br>glycolytic enzymes (phosphoglycerate mutase, enolase, pyruvate kinase) that catalyze the conversion of said 3-phospho-D-glycerate to pyruvate;<br>a pyruvate formate lyase or pyruvate dehydrogenase that catalyze the conversion of said pyruvate to acetyl-CoA; |
| Any microorganism herein described, wherein said pathway for the generation of product precursor acetyl-CoA and an acyl-CoA or keto-acid comprises:<br>an overexpressed acyl-CoA dehydrogenase that catalyzes the conversion of said acyl-CoA to a transenoyl-CoA;<br>an overexpressed enoyl-CoA hydratase that catalyzes the hydration of said transenoyl-CoA to a 3-hydroxyacyl-CoA;<br>an overexpressed 3-hydroxyacyl-CoA dehydrogenase that catalyzes the oxidation of said 3-hydroxyacyl-CoA to a ß-ketoacyl-CoA;<br>an overexpressed thiolase that catalyzes the cleavage of an acetyl-CoA from said ß-ketoacyl-CoA to produce acetyl-CoA and an acyl-CoA 2-carbons shorter than said starting acyl-CoA; |
| Any microorganism herein described, wherein said pathway for the regeneration of fumarate from an acyl-CoA or keto-acid comprises:<br>an overexpressed propionyl-CoA carboxylase that catalyzes the carboxylation of propionyl-CoA to (S)-methyl-malonyl-CoA;<br>an overexpressed methyl-malonyl-CoA epimerase that catalyzes the interconversion of said (S)-methyl-malonyl-CoA to (R)-methyl-malonyl-CoA;<br>an overexpressed methyl-malonyl-CoA mutase that catalyzes the isomerization of said (R)-methyl-malonyl-CoA to succinyl-CoA;<br>an overexpressed succinyl-CoA:2-methyl-alkyl-succinyl-CoA transferase or succinyl-CoA synthetase that catalyzes the conversion of said succinyl-CoA to succinate; |
| Any microorganism herein described, wherein said pathway for the regeneration of fumarate from an acyl-CoA or keto-acid comprises:<br>an overexpressed malate dehydrogenase for the conversion of said keto-acid (pyruvate) to malate;<br>an overexpressed fumarase for the dehydration of malate to fumarate; |
| Any microorganism herein described, wherein said pathway for the regeneration of fumarate from an acyl-CoA or keto-acid comprises:<br>an overexpressed carboxylic acid omega hydroxylase that catalyzes the conversion of said keto-acid to an omega-hydroxy-2-keto-acid;<br>an overexpressed alcohol dehydrogenase that catalyzes the conversion of said omega-hydroxyketo-acid to an omega-oxo-2-keto-acid;<br>an overexpressed aldehyde dehydrogenase that catalyzes the conversion of said omega-oxo-keto-acid to a dicarboxylic 2-keto-acid;<br>an overexpressed ketoreductase or malate dehydrogenase that catalyzes the conversion of said dicarboxylic 2-keto-acid to malate;<br>an overexpressed fumarase for the dehydration of malate to fumarate. |
| Any microorganism herein described, wherein said pathway for the oxygen-dependent activation and conversion to an acyl-CoA comprises:<br>an overexpressed alkane monooxygenase or alkane hydroxylase that catalyzes the terminal hydroxylation of a short-chain (C1-C5) alkane to produce a primary alcohol;<br>an overexpressed alcohol dehydrogenase that catalyzes the oxidation of said primary alcohol to produce an aldehyde; |

FIG. 15 cont.

| TABLE G |
|---|
| an overexpressed aldehyde dehydrogenase that catalyzes the oxidation of said aldehyde to produce a carboxylic acid and an overexpressed acyl-CoA synthetase that catalyzes the conversion of said carboxylic acid to an acyl-CoA, or an overexpressed acylating aldehyde dehydrogenase that catalyzes the conversion of said aldehyde to an acyl-CoA. |
| Any microorganism herein described, wherein said pathway for the generation of product precursor acetyl-CoA comprises: an overexpressed acyl-CoA dehydrogenase that catalyzes the conversion of said acyl-CoA to a transenoyl-CoA; an overexpressed enoyl-CoA hydratase that catalyzes the hydration of said transenoyl-CoA to a 3-hydroxyacyl-CoA; an overexpressed 3-hydroxyacyl-CoA dehydrogenase that catalyzes the oxidation of said 3-hydroxyacyl-CoA to a ß-ketoacyl-CoA; an overexpressed thiolase that catalyzes the cleavage of an acetyl-CoA from said ß-ketoacyl-CoA to produce acetyl-CoA and an acyl-CoA 2-carbons shorter than said starting acyl-CoA. |
| Any microorganism herein described, wherein said product synthesis pathway is a reverse beta oxidation (BOX-R) cycle that grows a primer by adding a 2-carbon donor thereto in each cycle, said BOX-R cycle comprising: an overexpressed thiolase that catalyzes the non-decarboxylative condensation of an acyl-CoA primer with a 2-carbon donor acetyl-CoA to produce a ß-ketoacyl-CoA; an overexpressed 3-oxoacyl-[acyl-carrier-protein] reductase or overexpressed 3-hydroxyacyl-CoA dehydrogenase that catalyzes the reduction of a ß-ketoacyl-CoA to a ß-hydroxyacyl-CoA; an overexpressed 3-hydroxyacyl-[acyl-carrier-protein] dehydratase or an overexpressed enoyl-CoA hydratase or 3-hydroxyacyl-CoA dehydratase that catalyzes the dehydration of a (3R)-ß-hydroxyacyl-CoA to a transenoyl-CoA; an overexpressed enoyl-[acyl-carrier-protein] reductase or acyl-CoA dehydrogenase or trans-enoyl-CoA reductase that catalyzes the reduction of a transenoyl-CoA to an acyl-CoA that is two carbons longer than said acyl-CoA primer; an overexpressed termination pathway that catalyzes the exit of an intermediate from said BOX-R cycle. |
| Any microorganism herein described, wherein said product synthesis pathway is a fatty acid biosynthesis (FAS) pathway that grows a primer by adding a 2-carbon donor thereto in each cycle, said FAS pathway comprising: an overexpressed acetyl-CoA carboxylase that catalyzes the conversion of acetyl-CoA to malonyl-CoA; an overexpressed malonyl-CoA-[acyl-carrier-protein] ("ACP") transacylase that catalyzes the conversion of said malonyl-CoA to malonyl-ACP; an overexpressed β-ketoacyl-ACP synthase that catalyzes the decarboxylative condensation of said malonyl-ACP with an acyl-ACP primer to produce a ß-ketoacyl-ACP; an overexpressed 3-oxoacyl-ACP reductase that catalyzes the reduction of a ß-ketoacyl-ACP to a ß-hydroxyacyl-ACP; an overexpressed 3-hydroxyacyl-ACP dehydratase that catalyzes the dehydration of a (3R)-ß-hydroxyacyl-ACP to a transenoyl-ACP; an overexpressed enoyl-ACP reductase that catalyzes the reduction of a transenoyl-ACP to an acyl-ACP that is two carbons longer than said acyl-ACP primer; an overexpressed termination pathway that catalyzes the exit of an intermediate from said FAS cycle. |
| Any microorganism herein described, wherein said termination pathway is selected from the group consisting of i) a CoA cleaving thioesterase, ii) an acyl-CoA:acetyl-CoA transferase, and iii) a phosphotransacylase and a carboxylate kinase. |
| Any microorganism herein described, wherein said termination pathway is an ACP cleaving thioesterase. |
| Any microorganism herein described, wherein said microorganism produces a product selected from the group consisting of carboxylic acids, (3R)-β-hydroxy carboxylic acids, β-keto carboxylic acids, and α,β-unsaturated carboxylic acids. |
| Any microorganism herein described, wherein said termination pathway is selected from the group consisting of i) an alcohol-forming coenzyme-A thioester reductase, and ii) an aldehyde-forming CoA thioester reductase and an alcohol dehydrogenase. |
| Any microorganism herein described, wherein said termination pathway is selected from the group consisting of i) an alcohol-forming ACP thioester reductase, and ii) an aldehyde-forming ACP thioester reductase and an alcohol dehydrogenase. |
| Any microorganism herein described, wherein said microorganism produces a product selected from the group consisting of primary alcohols, 1,(3R)-β diols, β-keto primary alcohols, and α,β-unsaturated primary alcohols. |
| Any microorganism herein described, wherein said termination pathway consists of an aldehyde-forming CoA thioester reductase and an aldehyde decarbonylase. |
| Any microorganism herein described, wherein said termination pathway consists of an aldehyde-forming ACP thioester reductase and an aldehyde decarbonylase. |
| Any microorganism herein described, wherein said microorganism produces a product selected from the group consisting of linear alkanes, linear alkan-3-ols, linear methyl-ketones, and 1-alkenes. |

FIG. 15 cont.

| TABLE G |
|---|
| Any microorganism herein described, wherein said termination pathway consists of an aldehyde-forming CoA thioester reductase and a transaminase. |
| Any microorganism herein described, wherein said termination pathway consists of an aldehyde-forming ACP thioester reductase and a transaminase. |
| Any microorganism herein described, wherein said microorganism produces a product selected from the group consisting of primary amines, 3-hydroxy-amines, 3-keto-amines, and α,β-unsaturated primary amines. |
| Any microorganism herein described, wherein said microorganism expresses a carboxylic acid omega hydroxylase and produces a product selected from the group consisting of ω-hydroxylated carboxylic acids, (3R)- β-, ω-dihydroxy carboxylic acids, β-keto, ω-hydroxy carboxylic acids, and α,β-unsaturated ω-hydroxylated carboxylic acids. |
| Any microorganism herein described, wherein said microorganism expresses a carboxylic acid ω hydroxylase, an alcohol oxidase, and an aldehyde dehydrogenase, and produces a product selected from the group consisting of ω-hydroxylated carboxylic acids, (3R)-β-, ω-dihydroxy carboxylic acids, β-keto, ω-hydroxy carboxylic acids, and α,β-unsaturated omega-hydroxylated carboxylic acids. |
| Any microorganism herein described, wherein said microorganism expresses a carboxylic acid ω hydroxylase, and produces a product selected from the group consisting of 1-,ω-diols, 1-,(3R)-β-, ω-triols, β-keto, 1-,ω-diols, and α,β-unsaturated 1-,ω-diols. |
| Any microorganism herein described, wherein said microorganism expresses a carboxylic acid ω hydroxylase, an alcohol oxidase, and an aldehyde dehydrogenase, and produces a product selected from the group consisting of di-carboxylic acids, (3R)-β-hydroxy di-carboxylic acids, β-keto di-carboxylic acids, and α,β-unsaturated di-carboxylic acids. |
| Any microorganism herein described, wherein said microorganism expresses a carboxylic acid ω hydroxylase, an alcohol oxidase, and a transaminase, and produces a product selected from the group consisting of primary alkanolamines (i.e. 1, ω-hydroxyamines), (3R)-β-hydroxy primary alkanolamines, β-keto primary alkanolamines, and α,β-unsaturated primary alkanolamines. |
| Any microorganism herein described, wherein said microorganism expresses a carboxylic acid ω hydroxylase, and produces a product selected from the group consisting of primary alkanolamines (i.e. 1, ω-hydroxyamines), (3R)-β-hydroxy primary alkanolamines, β-keto primary alkanolamines, and α,β-unsaturated primary alkanolamines. |
| Any microorganism herein described, wherein said microorganism expresses a carboxylic acid ω hydroxylase, an alcohol oxidase, and an aldehyde dehydrogenase, and produces a product selected from the group consisting of ω-amino acids, (3R)-β-hydroxy ω-amino acids, β-keto ω-amino acids, and α,β-unsaturated ω-amino acids. |
| Any microorganism herein described, wherein said microorganism expresses a carboxylic acid alpha hydroxylase, and produces a product selected from the group alpha-hydroxy carboxylic acids, alpha-, (3R)-β-dihydroxy carboxylic acids, α-hydroxy, β-keto carboxylic acids, and α,β-unsaturated α-hydroxy carboxylic acids. |
| Any microorganism herein described, wherein said microorganism expresses a carboxylic acid α hydroxylase, and produces a product selected from the group consisting of 1,2-diols, 1,2,3-triols, β-keto, 1,2-diols, and α,β-unsaturated 1,2-diols. |
| Any microorganism herein described, wherein said microorganism expresses a carboxylic acid α hydroxylase, and produces a product selected from the group consisting of α-hydroxylated primary amines, α-, β- dihydroxy primary amines, α-hydroxy, β-keto primary amines, and α-hydroxy, α,β-unsaturated primary amines. |
| Any microorganism herein described, further comprising reduced expression of fermentation enzymes leading to reduced production of lactate, acetate, ethanol and succinate. |
| Any microorganism herein described, wherein said overexpressed alkyl succinate synthase is encoded by *Azoarcus* sp. HxN1 *masBCDEG* (A9J4K0, A9J4K2, A9J4K4, A9J4K6, A9J4J6), *Desulfatibacillum alkenivorans assA1/assB1/assC1/assD1* (ACL03428.1, ACL03427.1, ACL03427.1, ACL03425.1), *Desulfosarcina* sp. BuS5 A39W_RS0101550/A39W_RS0101545/ A39W_RS0101540/A39W_RS0101535/A39W_RS19630/A39W_RS0101580 (WP_027352796.1, WP_027352795.1, WP_027352794.1, WP_027352793.1, WP_051374532.1, WP_027352800.1), *Desulfatibacillum alkenivorans assA2/assB2/assC2/assD2* (ACL03892.1, ACL03893.1, ACL03891.1, ACL03895.1), *Peptococcaceae* sp. SCADC (WP_036747468.1), *Aromatoleum* sp. OcN1 *masD* (CBK27727.1), *Desulfoglaeba alkanexedens assA* (ADJ51097.1), or homologues. |
| Any microorganism herein described, wherein said overexpressed succinyl-CoA:2-methyl-alkyl-succinyl-CoA transferase or 2-methyl-alkyl-succinyl-CoA synthetase is encoded by *Chloroflexus aurantiacus sct* (A9WGE3), *Thauera aromatica bbsEF* (Q9KJF0, Q9KJE9), *Escherichia coli sucCD* (P0A836, P0AGE9), *Desulfatibacillum alkenivorans Dalk_1737* (B8FFM9), or homologues. |
| Any microorganism herein described, wherein said overexpressed 2-methyl-alkyl-malonyl-CoA mutase is encoded by *Desulfatibacillum alkenivorans Dalk_0220/Dalk_0221* (ACL01930.1, ACL01929.1), or homologues. |
| Any microorganism herein described, wherein said overexpressed 2-methyl-alkyl-malonyl-CoA decarboxylase is encoded by *Desulfatibacillum alkenivorans Dalk_1740* (B8FFN2), or homologues. |

FIG. 15 cont.

| TABLE G |
|---|
| Any microorganism herein described, wherein said overexpressed 2-methyl-alkyl-succinyl-CoA dehydrogenase is encoded by *Rhodobacter sphaeroides mcd* (ADC44452.1) or homologues. |
| Any microorganism herein described, wherein said overexpressed mesaconyl-C1-CoA-C4-CoA transferase is encoded by *Chloroflexus aurantiacus mct* (A9WC36) or homologues. |
| Any microorganism herein described, wherein said overexpressed mesaconyl-C4-CoA hydratase is encoded by *Chloroflexus aurantiacus meh* (A9WC41) or homologues. |
| Any microorganism herein described, wherein said overexpressed citramalyl-CoA lyase is encoded by *Chloroflexus aurantiacus mclA* (A9WC35) or homologues. |
| Any microorganism herein described, wherein said overexpressed mesaconyl-CoA hydratase/β-methylmalyl-CoA dehydratase is encoded by *Chloroflexus aurantiacus mch* (A9WC34), *Rhodobacter sphaeroides mch* (Q3IZ78), or homologues. |
| Any microorganism herein described, wherein said overexpressed β-methylmalyl-CoA lyase is encoded by *Rhodobacter sphaeroides mcl1* (B9KLE8) or homologues. |
| Any microorganism herein described, wherein said overexpressed glyoxylate carboligase is encoded by *Escherichia coli gcl* (P0AEP7), or homologues. |
| Any microorganism herein described, wherein said overexpressed tartronate semialdehyde reductase is encoded by *Escherichia coli glxR* (P77161), or homologues. |
| Any microorganism herein described, wherein said overexpressed glycerate kinase is encoded by *Escherichia coli glxK* (P77364), or homologues. |
| Any microorganism herein described, wherein said overexpressed glycerate kinase is encoded by *Escherichia coli glxK* (P77364), or homologues. |
| Any microorganism herein described, wherein said phosphoglycerate mutase is encoded by *Escherichia coli gpmA* (P62707), *Escherichia coli gpmM* (P37689), or homologues. |
| Any microorganism herein described, wherein said enolase is encoded by *Escherichia coli eno* (P0A6P9), or homologues. |
| Any microorganism herein described, wherein said pyruvate kinase is encoded by *Escherichia coli pykA* (P21599), *Escherichia coli pykF* (P0AD61), or homologues. |
| Any microorganism herein described, wherein said pyruvate formate lyase is encoded by *Escherichia coli pflB/pflA* (P09373) or homologues. |
| Any microorganism herein described, wherein said pyruvate dehydrogenase is encoded by *Escherichia coli aceEF/lpd* (P0AFG8, P06959, C3TQA2) or homologues. |
| Any microorganism herein described, wherein said overexpressed acyl-CoA dehydrogenase is encoded by *Ascaris suum* ACDH (Q08523), *Escherichia coli fadE* (AP_000876.1), or homologues. |
| Any microorganism herein described, wherein said overexpressed enoyl-CoA hydratase encoded by *Pseudomonas putida fadB1x* (NP_744366.1), *Pseudomonas putida phaL* (NP_745413.1), *Alcanivorax borkumensis ech1* (YP_691868.1), *Alcanivorax borkumensis ech2* (YP_692707.1) *Alcanivorax borkumensis phaB* (YP_692246.1), *Escherichia coli fadB* (NP_418288.1), or homologues. |
| Any microorganism herein described, wherein said overexpressed 3-hydroxyacyl-CoA dehydrogenase is encoded by *Pseudomonas putida fadB2x* (Q88KS5), *Ascaris suum* GS_18673, *Escherichia coli fadB* (NP_418288.1), or homologues. |
| Any microorganism herein described, wherein said overexpressed thiolase is encoded by *Pseudomonas putida fadAx* (NP_744364.1), *Alcanivorax borkumensis fadAx* (YP_692368.1), *Escherichia coli atoB* (NP_416728.1), *Escherichia coli yqeF* (NP_417321.2), *Escherichia coli fadA* (YP_026272.1), *Escherichia coli fadI* (NP_416844.1), *Ralstonia eutropha bktB* (AAC38322.1), or homologues. |
| Any microorganism herein described, wherein said overexpressed propionyl-CoA carboxylase is encoded by *Chloroflexus aurantiacus Caur_2034/Caur_3435* (A9WEI4, A9WKJ2), *Rhodobacter sphaeroides pccAB* (Q3J4D9, Q3J4E3), or homologues. |
| Any microorganism herein described, wherein said overexpressed methyl-malonyl-CoA epimerase is encoded by *Metallosphaera sedula Msed_0639* (A4YEG2) or homologues. |
| Any microorganism herein described, wherein said overexpressed methyl-malonyl-CoA mutase is encoded by *Rhodobacter sphaeroides mcmA* (Q3J4D7), or homologues. |
| Any microorganism herein described, wherein said overexpressed succinyl-CoA synthetase is encoded by *Escherichia coli sucCD* (P0A836, P0AGE9), or homologues. |
| Any microorganism herein described, wherein said overexpressed malate dehydrogenase is encoded by *Escherichia coli maeA* (P26616), *Escherichia coli maeB* (P76558), or homologues. |
| Any microorganism herein described, wherein said overexpressed fumarase is encoded by *Escherichia coli fumA* (P0AC33), *Escherichia coli fumB* (P14407), *Escherichia coli fumC* (P05042), or homologues. |

FIG. 15 cont.

| TABLE G |
|---|
| Any microorganism herein described, wherein said overexpressed carboxylic acid omega hydroxylase is encoded by *Pseudomonas putida* alkBGT (YP_009076004.1, Q9WWW4.1, Q9L4M8.1), *Marinobacter aquaeolei* CYP153A (ABM17701.1), *Mycobacterium marinum* CYP153A16 (YP_001851443.1), *Polaromonas* sp. CYP153A (YP_548418.1), *Nicotiana tabacum* CYP94A5 (AAL54887.1), *Vicia sativa* CYP94A1 (AAD10204.1), *Vicia sativa* CYP94A2 (AAG33645.1), *Arabidopsis thaliana* CYP94B1 (BAB08810.1), *Arabidopsis thaliana* CYP86A8 (CAC67445.1), *Candida tropicalis* CYP52A1 (AAA63568.1, AAA34354.1, AAA34334.1), *Candida tropicalis* CYP52A2 (AAA34353.2, CAA35593.1), *Homo sapiens* CYP4A11 (AAQ56847.1), or homologs. |
| Any microorganism herein described, wherein said overexpressed alcohol dehydrogenase is encoded by *Rhodococcus ruber* SC1 cddC (AAL14237.1), *Acinetobacter* sp. SE19 chnD (AAG10028.1), *Escherichia coli* betA (NP_414845.1), *Escherichia coli* dkgA (NP_417485.4), *Escherichia coli* eutG (NP_416948.4), *Escherichia coli* fucO (NP_417279.2), *Escherichia coli* ucpA (NP_416921.4), *Escherichia coli* yahK (NP_414859.1), *Escherichia coli* ybbO (NP_415026.1), *Escherichia coli* ybdH (NP_415132.1), *Escherichia coli* yiaY (YP_026233.1), *Escherichia coli* yjgB (NP_418690.4), or homologues. |
| Any microorganism herein described, wherein said overexpressed aldehyde dehydrogenase is encoded by *Rhodococcus ruber* SC1 cddD (AAL14238.1), *Acinetobacter* sp. SE19 chnE (AAG10022.1), or homologues. |
| Any microorganism herein described, wherein said overexpressed ketoreductase/malate dehydrogenase is encoded by *Escherichia coli* mdh (P61889), or homologues. |
| Any microorganism herein described, wherein said overexpressed alkane monooxygenase or alkane hydroxylase is encoded by *Pseudomonas putida* alkBGT (YP_009076004.1, Q9WWW4.1, Q9L4M8.1), *Mycobacterium* sp. strain HXN-1500 CYP153A6 (Q5K1Y6), *Gordonia* sp. TY-5 prmABCD (AB112920.1), *Thauera butanivorans* bmoXYZ/bmoC/bmoB (Q8KQF0, Q8KQE9, Q8KQE7, Q8KQE6, Q8KQE8), *Alcanivorax borkumensis* alkB1 (Q0VKZ3.1), *Alcanivorax borkumensis* alkB2 (Q0VTH3.1), *Sphingopyxis macrogoltabida* ahpG3 (Q5F4D3), *Methylosinus trichosporium* OB3b mmoXYZBC/orfY (P27353, P27354, P27355, Q53563, P27356, Q53562), *Methylococcus capsulatus* Bath mmoXYZBC/orfY (P22869, P18798, P11987, P18797, 22868, P22867), *Rhodobacter sphaeroides* RSP2792/RSP2793/RSP2794/RSP2795 (YP_352924.1, (YP_352923.1, YP_352922.1, YP_352921.1), or homologues. |
| Any microorganism herein described, wherein said overexpressed alcohol dehydrogenase is encoded by *Pseudomonas putida* alkJ (Q9WWW2), *Gordonia* sp. TY-5 adh1 (AB112920.1), *Bacillus methanolicus* mdh (P31005), *Mycobacterium* sp. DSM 3803 mdo (C5MRT8), *Methylobacterium extorquens* moxI, moxF (P14775, P16027), *Escherichia coli* betA (NP_414845.1), *Escherichia coli* dkgA (NP_417485.4), *Escherichia coli* eutG (NP_416948.4), *Escherichia coli* fucO (NP_417279.2), *Escherichia coli* ucpA (NP_416921.4), *Escherichia coli* yahK (NP_414859.1), *Escherichia coli* ybbO (NP_415026.1), *Escherichia coli* ybdH (NP_415132.1), *Escherichia coli* yiaY (YP_026233.1), *Escherichia coli* yjgB (NP_418690.4), or homologues. |
| Any microorganism herein described, wherein said overexpressed aldehyde dehydrogenase is encoded by *Escherichia coli* aldA (P25553), *Escherichia coli* aldB (P37685), *Escherichia coli* puuC (P23883), *Pseudomonas putida* alkH (Q9WWW3), *Klebsiella pneumoniae* KPN_01018 (A6T782), *Rhodococcus erythropolis* aldhR (Q4F895), or homologues. |
| Any microorganism herein described, wherein said overexpressed acyl-CoA synthetase is encoded by *Escherichia coli* fadD (P69451), *Escherichia coli* fadK (P38135), *Pseudomonas putida* alkK (Q9L4M6), or homologues. |
| Any microorganism herein described, wherein said overexpressed acylating aldehyde dehydrogenase is encoded by *E. coli* mhpF (NP_414885.1), *Pseudomonas* sp. CF600 dmpF (Q52060), or homologues. |
| Any microorganism herein described, wherein said overexpressed acyl-CoA dehydrogenase is encoded by *Escherichia coli* fadE (AP_000876.1), or homologues. |
| Any microorganism herein described, wherein said overexpressed enoyl-CoA hydratase encoded by *Escherichia coli* fadB (NP_418288.1), or homologues. |
| Any microorganism herein described, wherein said overexpressed 3-hydroxyacyl-CoA dehydrogenase is encoded by *Escherichia coli* fadB (NP_418288.1), or homologues. |
| Any microorganism herein described, wherein said overexpressed thiolase is encoded by, *Escherichia coli* atoB (NP_416728.1), *Escherichia coli* yqeF (NP_417321.2), *Escherichia coli* fadA (YP_026272.1), *Escherichia coli* fadI (NP_416844.1), or homologues. |
| Any microorganism herein described, wherein said overexpressed thiolase is encoded by *E. coli* atoB (NP_416728.1), *E. coli* yqeF (NP_417321.2), *E. coli* fadA (YP_026272.1), *E. coli* fadI (NP_416844.1), *Ralstonia eutropha* bktB (AAC38322.1), *Pseudomonas* sp. Strain B13 catF (AAL02407.1), *E coli* paaJ (NP_415915.1), *Pseudomonas putida* pcaF (AAA85138.1), *Rhodococcus opacus* pcaF (YP_002778248.1), *Streptomyces* sp. pcaF (AAD22035.1), *Ralstonia eutropha* phaA (AEI80291.1), *Clostridium acetobutylicum* thlA (AAC26023.1), or *Clostridium acetobutylicum* thlB (AAC26026.1), or homologues. |
| Any microorganism herein described, wherein said overexpressed 3-hydroxyacyl-CoA dehydrogenase or 3-oxoacyl-[acyl-carrier-protein] reductase is encoded by *E. coli* fadB (NP_418288.1), *E. coli* fadJ (NP_416843.1), *Ralstonia eutropha* phaB1 |

FIG. 15 cont.

| TABLE G |
|---|
| (YP_725942.1), *Ralstonia eutropha phaB2* (YP_726470.1), *Ralstonia eutropha phaB3* (YP_726636.1), *E. coli paaH* (P76083), *E. coli fabG* (NP_415611.1), or homologues. |
| Any microorganism herein described, wherein said overexpressed enoyl-CoA hydratase, 3-hydroxyacyl-CoA dehydratase, or 3-hydroxyacyl-[acyl-carrier-protein] dehydratase is encoded by *E. coli fadB* (NP_418288.1), *E. coli fadJ* (NP_416843.1), *Aeromonas caviae phaJ* (O32472.1), *Pseudomonas aeruginosa phaJ1* (BAA92740.1), *Pseudomonas aeruginosa phaJ2* (BAA92741.1), *Pseudomonas aeruginosa phaJ3* (BAC44834.1), *Pseudomonas aeruginosa phaJ4* (BAC44835.1), *E. coli paaF* (P76082), *E. coli fabA* (NP_415474.1), *E. coli fabZ* (NP_414722.1), or homologues. |
| Any microorganism herein described, wherein said trans-enoyl-CoA reductase or enoyl-[acyl-carrier-protein] reductase is encoded by *E. coli ydiO* (P0A9U8), *Euglena gracilis egTER* (Q5EU90.1), *Treponema denticola tdTER* (NP_971211.1), *E. coli fabI* (NP_415804.1), *Enterococcus faecalis fabK* (NP_816503.1), *Bacillus subtilis fabL* (KFK80655.1), *Vibrio cholerae fabV* (ABX38717.1), or homologues. |
| Any microorganism herein described, wherein said overexpressed acetyl-CoA carboxylase is encoded by *E. coli accABCD* (P0ABD5, P0ABD8, P24182, P0A9Q5), or homologues. |
| Any microorganism herein described, wherein said overexpressed malonyl-CoA-ACP transacylase is encoded by *E. coli fabD* (P0AAI9), or homologues. |
| Any microorganism herein described, wherein said overexpressed β-ketoacyl-ACP synthase is encoded by *E. coli fabB* (P0A953), *E. coli fabF* (P0AAI5), *E. coli fabH* (P0A6R0), or homologues. |
| Any microorganism herein described, wherein said overexpressed 3-oxoacyl-[acyl-carrier-protein] reductase is encoded by *E. coli fabG* (NP_415611.1), or homologues. |
| Any microorganism herein described, wherein said overexpressed 3-hydroxyacyl-[acyl-carrier-protein] dehydratase is encoded by *E. coli fabA* (NP_415474.1), *E. coli fabZ* (NP_414722.1), or homologues. |
| Any microorganism herein described, wherein said enoyl-[acyl-carrier-protein] reductase is encoded by *E. coli fabI* (NP_415804.1), *Enterococcus faecalis fabK* (NP_816503.1), *Bacillus subtilis fabL* (KFK80655.1), *Vibrio cholerae fabV* (ABX38717.1), or homologues. |
| Any microorganism herein described, wherein said overexpressed thioesterase is encoded by *E. coli tesA* (NP_415027.1), *E. coli tesB* (NP_414986.1), *E. coli yciA* (NP_415769.1), *E. coli fadM* (NP_414977.1), *E. coli ydil* (NP_416201.1), *E. coli ybgC* (NP_415264.1), *Alcanivorax borkumensis tesB2* (YP_692749.1) *Fibrobacter succinogenes Fs2108* (YP_005822012.1), *Prevotella ruminicola Pr655* (YP_003574018.1) *Prevotella ruminicola Pr1687* (YP_003574982.1), or homologues. |
| Any microorganism herein described, wherein said overexpressed acyl-CoA:acetyl-CoA transferase is encoded by *E. coli atoD* (NP_416725.1), *Clostridium kluyveri cat2* (AAA92344.1), *Clostridium acetobutylicum ctfAB* (NP_149326.1, NP_149327.1) or *E. coli ydiF* (NP_416209.1), ), or homologues. |
| Any microorganism herein described, wherein said overexpressed phosphotransacylase is encoded by *Clostridium acetobutylicum ptb* (NP_349676.1), *Enterococcus faecalis ptb* (AAD55374.1), *Salmonella enterica pduL* (AAD39011.1), or homologues. |
| Any microorganism herein described, wherein said overexpressed carboxylate kinase is encoded by *Clostridium acetobutylicum buk* (AAK81015.1), *Enterococcus faecalis buk* (AAD55375.1), *Salmonella enterica pduW* (AAD39021.1), or homologues. |
| Any microorganism herein described, wherein said overexpressed ACP-cleaving thioesterase is encoded by *E. coli tesA* (NP_415027.1), *Cuphea palustris fatB1* (AAC49179.1), *Cuphea viscosissima fatB3* (AEM72524.1), *Ulmus americana fatB1* (AAB71731.1), *Cocos nucifera fatB2* (AEM72520.1), *Elaeis guineensis PTE* (AAD42220.2), *Clostridium perfringens CPF_2954* (ABG82470.1), *Umbellularia californica fatB1* (AAA34215.1), or homologues. |
| Any microorganism herein described, wherein said overexpressed alcohol-forming coenzyme-A thioester reductase is encoded by *Clostridium acetobutylicum adhE2* (YP_009076789.1), *Arabidopsis thaliana At3g11980* (AEE75132.1), *Arabidopsis thaliana At3g44560* (AEE77915.1), *Arabidopsis thaliana At3g56700* (AEE79553.1), *Arabidopsis thaliana At5g22500* (AED93034.1), *Arabidopsis thaliana CER4* (AEE86278.1), *Marinobacter aquaeolei VT8 maqu_2220* (YP_959486.1), *Marinobacter aquaeolei VT8 maqu_2507* (YP_959769.1), or homologues. |
| Any microorganism herein described, wherein said overexpressed aldehyde-forming CoA thioester reductase is encoded by *Acinetobacter calcoaceticus acr1* (AAC45217.1), *Acinetobacter sp Strain M-1 acrM* (BAB85476.1), *Clostridium beijerinckii ald* (AAT66436.1), *E. coli eutE* (NP_416950.1), *Salmonella enterica eutE* (AAA80209.1), *E. coli mhpF* (NP_414885.1), or homologues. |
| Any microorganism herein described, wherein said overexpressed alcohol-forming ACP thioester reductase is encoded by *Marinobacter aquaeolei VT8 maqu_2220* (YP_959486.1), *Hahella chejuensis hch_05075* (ABC31758.1), *Marinobacter algicola MDG893_11561* (A6EVI7), *Bermanella marisrubri RED65_09894* (Q1N697), or homologues. |
| Any microorganism herein described, wherein said overexpressed aldehyde-forming ACP thioester reductase is encoded by *Nostoc punctiforme Npun_R1710* (ACC80381.1), *Synechococcus elongates Synpcc7942_1594* (Q54765), *Prochlorococcus marinus P9515_05971* (A2BVJ5), *Synechocystis sp. PCC 6803 sll0209* (YP_005652204.1), or homologues. |

FIG. 15 cont.

| TABLE G |
|---|
| Any microorganism herein described, wherein said overexpressed alcohol dehydrogenase is encoded by *E. coli betA* (NP_414845.1), *E. coli dkgA* (NP_417485.4), *E. coli eutG* (NP_416948.4), *E. coli fucO* (NP_417279.2), *E. coli ucpA* (NP_416921.4), *E. coli yahK* (NP_414859.1), *E. coli ybbO* (NP_415026.1), *E. coli ybdH* (NP_415132.1), *E. coli yiaY* (YP_026233.1), *E. coli yjgB* (NP_418690.4), homologues. |
| Any microorganism herein described, wherein said aldehyde decarbonylase overexpressed is encoded by *Synechococcus elongatus* PCC7942 orf1593 (Q54764.1), *Nostoc punctiforme* PCC73102 npun_R1711 (B2J1M1.1), *Prochlorococcus marinus* MIT9313 pmt1231 (Q7V6D4.1), or homologues. |
| Any microorganism herein described, wherein said overexpressed transaminase is encoded by *Arabidopsis thaliana* At3g22200 (NP_001189947.1), *Alcaligenes denitrificans* aptA (AAP92672.1), *Bordetella bronchiseptica* BB0869 (WP_015041039.1), *Bordetella parapertussis* BPP0784 (WP_010927683.1), *Brucella melitensis* BAWG_0478 (EEW88370.1), *Burkholderia pseudomallei* BP1026B_I0669 (AFI65333.1), *Chromobacterium violaceum* CV2025 (AAQ59697.1), *Oceanicola granulosus* OG2516_07293 (WP_007254984.1), *Paracoccus denitrificans* PD1222 Pden_3984 (ABL72050.1), *Pseudogulbenkiania ferrooxidans* ω-TA (WP_008952788.1), *Pseudomonas putida* ω-TA (P28269.1), *Ralstonia solanacearum* ω-TA (YP_002258353.1), *Rhizobium meliloti* SMc01534 (NP_386510.1), and *Vibrio fluvialis* ω-TA (AEA39183.1), *Mus musculus* abaT (AAH58521.1) *E. coli gabT* (YP_490877.1), or homologues. |
| Any microorganism herein described, wherein said overexpressed carboxylic acid omega hydroxylase is encoded by *Pseudomonas putida* alkBGT (YP_009076004.1, Q9WWW4.1, Q9L4M8.1), *Marinobacter aquaeolei* CYP153A (ABM17701.1), *Mycobacterium marinum* CYP153A16 (YP_001851443.1), *Polaromonas sp.* CYP153A (YP_548418.1), *Nicotiana tabacum* CYP94A5 (AAL54887.1), *Vicia sativa* CYP94A1 (AAD10204.1), *Vicia sativa* CYP94A2 (AAG33645.1), *Arabidopsis thaliana* CYP94B1 (BAB08810.1), *Arabidopsis thaliana* CYP86A8 (CAC67445.1), *Candida tropicalis* CYP52A1 (AAA63568.1, AAA34354.1, AAA34334.1), *Candida tropicalis* CYP52A2 (AAA34353.2, CAA35593.1), *Homo sapiens* CYP4A11 (AAQ56847.1), or homologues. |
| Any microorganism herein described, wherein said overexpressed alcohol oxidase is encoded by *Rhodococcus ruber* SC1 cddC (AAL14237.1), *Acinetobacter sp.* SE19 chnD (AAG10028.1), *E. coli yahK* (NP_414859.1), *E. coli yjgB* (NP_418690.4), or homologues. |
| Any microorganism herein described, wherein said overexpressed aldehyde dehydrogenase is encoded by *Rhodococcus ruber* SC1 cddD (AAL14238.1), *Acinetobacter sp.* SE19 chnE (AAG10022.1), or homologues. |
| Any microorganism herein described, wherein said overexpressed fatty acid alpha hydroxylases is encoded by *Myxococcus xanthus* MXAN_0191 (YP_628473.1), *Stigmatella aurantiaca* STIAU_3334 (YP_003957653.1), or homologues. |
| Any microorganism herein described, wherein said reduced expression of fermentation enzymes are ΔadhE, (Δpta or ΔackA or ΔackApta), ΔpoxB, ΔldhA, and ΔfrdA and less acetate, lactate, ethanol and succinate are thereby produced. |
| A method of a product comprising growing a genetically engineered microorganism or recombinant bacteria according to any of claims 1-114 in a culture broth containing an alkane as the sole carbon source, activating said alkane, generating precursor intermediate acetyl-CoA, producing a product from said acetyl-CoA, and isolating said product. |
| A method of a product comprising growing a genetically engineered microorganism or recombinant bacteria according to any of claims 1-114 in a culture broth containing an alkane as the sole carbon source and a terminal electron acceptor (such as $SO_4^{2-}$, $NO_3^-$, $Fe^{3+}$, $O_2$, $Mn^{4+}$), activating said alkane, generating precursor intermediate acetyl-CoA, producing a product from said acetyl-CoA, and isolating said product. |

FIG. 15 cont.

BIOCONVERSION OF SHORT-CHAIN HYDROCARBONS TO FUELS AND CHEMICALS

PRIOR RELATED APPLICATIONS

This application is a continuation of U.S. application Ser. No. 15/562,606, filed Sep. 28, 2017, which is a 371 application of International Application No. PCT/US16/25103, published in English and filed on Mar. 31, 2016, which claims priority to U.S. Ser. No. 62/140,628, filed Mar. 31, 2015. The entire teachings of the above applications are incorporated herein by reference.

FEDERALLY SPONSORED RESEARCH STATEMENT

Not applicable.

FIELD OF THE DISCLOSURE

The disclosure generally relates to the use of microorganisms with novel pathways for the conversion of short-chain hydrocarbons (e.g. methane, ethane, propane, butane, pentane) to fuels and chemicals (e.g. carboxylic acids, alcohols, hydrocarbons, and their alpha-, beta-, and omega-functionalized derivatives).

BACKGROUND OF THE DISCLOSURE

Global natural gas ($CH_4$) resources that are technically recoverable with new horizontal drilling and efficient extraction technologies are estimated at $7.2 \times 10^3$ trillion cubic feet (Tcf), with estimates for the US ranging between $0.65 \times 10^3$ Tcf and up to $2 \times 10^3$ Tcf. Furthermore, about 5 trillion cubic feet (Tcf) of natural gas liquids or NGLs (primarily ethane, propane and butane) are produced annually in the United States and technically recoverable reserves of this resource are estimated at over 400 Tcf based on wet natural gas estimates.

The invention re-purposes native pathways for anaerobic and aerobic activation of medium- and long-chain hydrocarbons ($C_6$-$C_{20}$) to function with short-chain substrates ($C_1$-$C_5$). Through these engineered pathways, the short-chain hydrocarbon substrates are converted to central, intracellular metabolites such as acetyl-CoA, which can in turn be converted to a variety of fuels and chemicals through other native or engineered pathways.

SUMMARY OF THE DISCLOSURE

This invention demonstrates pathways that can be utilized for the conversion of short chain hydrocarbon feedstocks to a variety of fuels and chemicals. This is accomplished through key pathway modules for hydrocarbon activation and conversion to an acyl-CoA intermediate, generation of product precursor acetyl-CoA, which in certain cases also entails the generation of an addition acyl-CoA or keto-acid, and the formation of a desired product from acetyl-CoA. Dependent on the type of hydrocarbon activation pathway utilized, the regeneration of compounds required for activation from an acyl-CoA or keto-acid intermediate are also required.

Two main approaches for short chain hydrocarbon activation are exploited: 1) the oxygen-independent activation via fumarate addition, which given the need for fumarate during oxygen-independent activation also requires pathways for the regeneration of this intermediate for continued activation cycles, and 2) the oxygen-dependent activation via the terminal addition of a hydroxyl group to the alkane.

As used herein, an "oxygen-independent activation via fumarate addition" is the addition of fumarate to an alkane leading a 2-methyl-alkyl-succinate:

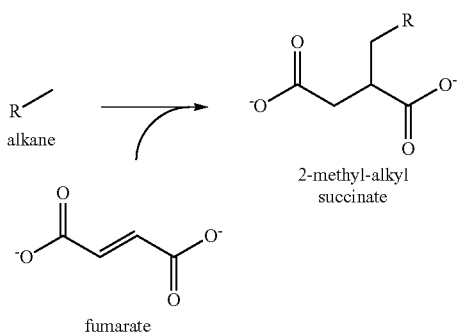

The enzyme that catalyzes this reaction is an "alkyl succinate synthase," and more than 40 such examples are exemplified herein. Alkyl succinate synthases that are specific for methane as a substrate are called "methyl succinate synthases," for ethane they are called "ethyl succinate synthases," and so on, although there are of course enzymes with broader substrate specificity.

As used herein, an "oxygen-dependent activation" is the terminal addition of a hydroxyl group to the alkane to form a primary alcohol.

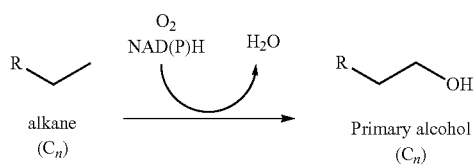

The enzyme that catalyzes this reaction is an "alkane monooxygenase" or "alkane hydroxylase", and as above, they may sometimes be named according the alkane substrate specificity, although there are of course enzymes in both classes with broader substrate specificity. Several examples are provided herein.

Regardless of the activation pathway utilized, the resulting activated compound is then converted into an acyl-CoA intermediate through a series of reactions. Once the given acyl-CoA intermediate is produced, various pathways dependent on the type of acyl-CoA generated can be exploited for the generation of the product precursor acetyl-CoA.

Synthesis of the desired product(s) from acetyl-CoA can be accomplished through various engineered metabolic pathways, including a reversal of the beta-oxidation cycle (BOX-R) or the fatty acid biosynthesis (FAS) pathway. Following chain elongation through either of these pathways, the selection of a given termination pathway enables the synthesis of various product families.

As used herein "termination pathway" or "termination enzyme(s)" refers to one or more enzymes (or genes encoding same) that will pull reaction intermediates out the BOX-R or FAS cycle and produce the desired end product.

By "primary termination pathway" what is meant is an intermediate from the BOX-R or FAS cycle is pulled out of the BOX-R or FAS cycle by one (which can have more than one activity) or more termination enzymes and results in i) carboxylic acids, ii) primary alcohols, iii) hydrocarbons, or iv) primary amines, from CoA intermediates as described in FIG. 1.

By "secondary termination pathway" what is meant is that the intermediate pulled out of the BOX-R or FAS cycle by a primary termination pathway enzyme is further modified by one or more enzymes.

Many examples of termination pathways are available and the following table provides several examples:

TABLE A

Termination Pathways for Conversion of CoA Intermediates to Desired Products

| Reaction | Illustration | EC | Enzyme names | Source organism and gene name | Protein Accession Numbers |
|---|---|---|---|---|---|
| Acyl-CoA→ Carboxylic acid | An acyl-CoA → A carboxylic acid | 3.1.2.- | Thioesterase | E. coli tesA | NP_415027.1 |
| | | | | E. coli tesB | NP_414986.1 |
| | | | | E. coli yciA | NP_415769.1 |
| | | | | E. coli fadM | NP_414977.1 |
| | | | | E. coli ydiI | NP_416201.1 |
| | | | | E. coli ybgC | NP_415264.1 |
| | | | | Alcanivorax borkumensis tesB2 | YP_692749.1 |
| | | | | Fibrobacter succinogenes Fs2108 | YP_005822012.1 |
| | | | | Prevotella rumincola Pr655 | YP_003574018.1 |
| | | | | Prevotella ruminicola Pr1687 | YP_003574982.1 |
| | | 2.8.3.8 | Acyl-CoA:acetyl-CoA transferese | E. coli atoD | NP_416725.1 |
| | | | | Clostridium kluyveri cat2 | AAA92344.1 |
| | | | | Clostridium acebotuylicum ctfAB | NP_149326.1 |
| | | | | | NP_149327.1 |
| | | | | E. coli ydiF | NP_416209.1 |
| | | 2,3,1,-; 2.7.2.1; 2.7.2.15 | Phosphotrans-acylase + Carboxylate kinase | Clostridium acetobutylicum ptb | NP_349676.1 |
| | | | | Enterococcus faecalis ptb | AAD55374.1 |
| | | | | Salmonella enterica pduL | AAD39011.1 |
| | | | | Clostridium acetobutylicum buk | AAK81015.1 |
| | | | | Enterococcus faecalis buk | AAD55375.1 |
| | | | | Salmonella enterica pduW | AAD39021.1 |
| Acyl-CoA→ Alcohol | An acyl-CoA → An alcohol | 1.2.1.84 | Alcohol-forming CoA reductase | Clostridium acetobutylicum adhE2 | YP_009076789.1 |
| | | | | Arabidopsis thaliana At3g11980 | AEE75132.1 |
| | | | | Arabidopsis thaliana At3g44560 | AEE77915.1 |
| | | | | Arabidopsis thaliana At3g56700 | AEE79553.1 |
| | | | | Arabidopsis thaliana At5g22500 | AED93034.1 |
| | | | | Arabidopsis thaliana CER4 | AEE86278.1 |
| | | | | Marinobacter aquaeolei VTB maqu_2220 | YP_959486.1 |
| | | | | Marinobacter aquaeolei VTB maqu_2507 | YP_959769.1 |
| Acyl-CoA→ Aldehyde | An acyl-CoA → An aldehyde | 1.2.1.10 | Aldehyde forming CoA reductase | Acinetobacter calcoaceticus acr1 | AAC45217.1 |
| | | | | Acinetobacter sp Strain M-1 acrM | BAB85476.1 |
| | | | | Clostridium beijerinckii ald | AAT66436.1 |
| | | | | E. coli eutE | NP_416950.1 |
| | | | | Salmonella enterica eutE | AAA80209.1 |
| | | | | E. coli mhpF | NP_414885.1 |
| Aldehyde→ Alcohol | An aldehyde → An alcohol | 1.1.1.- | Alcohol dehydrogenase | E. coli betA | NP_414845.1 |
| | | | | E. coli dkgA | NP_417485.4 |
| | | | | E. coli eutG | NP_416948.4 |
| | | | | E. coli fucO | NP_417279.2 |
| | | | | E. coli upcA | NP_416921.1 |
| | | | | E. coli yahK | NP_414859.1 |
| | | | | E. coli ybbO | NP_415026.1 |
| | | | | E. coli ybdH | NP_415132.1 |
| | | | | E. coli yiaY | YP_026233.1 |
| | | | | E. coli yjgB | NP_418690.4 |
| Aldehyde→ Alkane | An aldehyde → An alkane | 4.1.99.5 | Aldehyde decarbonylase | Synechococcus elongatus PCC7942 orf1593 | Q54764.1 |
| | | | | Nostoc punctiforme PCC73102 npun_R1711 | B2J1M1.1 |
| | | | | Prochlorococcus marinus MIT9313 pmt1231 | Q7V6D4.1 |

TABLE A-continued

Termination Pathways for Conversion of CoA Intermediates to Desired Products

| Reaction | Illustration | EC | Enzyme names | Source organism and gene name | Protein Accession Numbers |
|---|---|---|---|---|---|
| Aldehyde→Amine | An aldehyde → An amine | 2.6.1.- | Transaminase | Arabidopsis thaliana At3g22200 | NP_001189947.1 |
| | | | | Alcaligenes denitrificans AptA | AAP92672.1 |
| | | | | Bordetella bronchiseptica BB0869 | WP_015041039.1 |
| | | | | Bordetella parapertussis BPP0784 | WP_010927683.1 |
| | | | | Brucella melitensis BAWG_0478 | EEW88370.1 |
| | | | | Burkholderia pseudomallei BP1026B_I0669 | AFI65333.1 |
| | | | | Chromobacterium violaceum CV2025 | AAQ59697.1 |
| | | | | Oceanicola granulosus OG2516_07293 | WP_007254984.1 |
| | | | | Paracoccus denitrificans PD1222 Pden_3984 | ABL72050.1 |
| | | | | Pseudogulbenkiania ferrooxidans ω-TA | WP_008952788.1 |
| | | | | Pseudomonas putida ω-TA | P28269.1 |
| | | | | Ralstonia solanacearum ω-TA | YP_002258353.1 |
| | | | | Rhizobium meliloti SMc01534 | NP_386510.1 |
| | | | | Vibrio fluvialis ω-TA | AEA39183.1 |
| | | | | Mus musculus abaT | AAH58521.1 |
| | | | | E. coli gabT | YP_490877.1 |
| Carboxylic Acid→ω-hydroxy-acid | Carboxylic Acid → ω-Hydroxy-Carboxylic Acid | 1.14.- | Carboxylic acid omega hydroxylase | Pseudomonas putida alkBGT | YP_009076004.1, Q9WWW4.1, Q9L4M8.1 |
| | | | | Marinobacter aquaeolei CYP153A | ABM17701.1 |
| | | | | Mycobacterium marinum CYP153A16 | YP_001851443.1 |
| | | | | Polaromonas sp. CYP153A | YP_548418.1 |
| | | | | Nicotiana tabacum CYP94A5 | AAL54887.1 |
| | | | | Vicia sativa CYP94A1 | AAD10204.1 |
| | | | | Vicia sativa CYP94A2 | AAG33645.1 |
| | | | | Arabidopsis thaliana CYP94B1 | BAB08810.1 |
| | | | | Arabidopsis thaliana CYP86A8 | CAC67445.1 |
| | | | | Candida tropicalis CYP52A1 | AAA63568.1, AAA34354.1, AAA34334.1 |
| | | | | Candida tropicalis CYP52A2 | AAA34353.2, CAA35593.1 |
| | | | | Homo sapiens CYP4A11 | AAQ56847.1 |
| ω-hydroxy-acid→ω-oxo-acid | ω-Hydroxy-Carboxylic Acid → ω-Oxo-Carboxylic Acid | 1.1.1.- | Alcohol oxidase/alcohol dehydrogenase | Rhodococcus ruber SC1 cddC | AAL14237.1 |
| | | | | Acinetobacter sp. SE19 chnD | AAG10028.1 |
| | | | | E. coli yah K | NP_414859.1 |
| | | | | E. coli yjgB | NP_418690.4 |
| ω-oxo-acid→dicarboxylic acid | ω-Oxo-Carboxylic Acid → Dicarboxylic Acid | 1.2.1.- | Aldehyde dehydrogenase | Rhodococcus ruber SC1 cddD | AAL14238.1 |
| | | | | Acinetobacter sp SE19 chnE | AAG10022.1 |

TABLE A-continued

Termination Pathways for Conversion of CoA Intermediates to Desired Products

| Reaction | Illustration | EC | Enzyme names | Source organism and gene name | Protein Accession Numbers |
|---|---|---|---|---|---|
| Carboxylic Acid→ α-hydroxyacid | 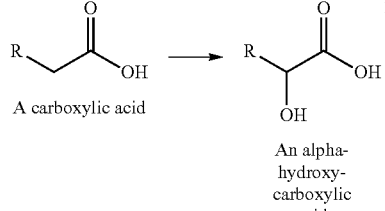 | 1.14.- | Carboxylic acid alpha hydroxy-lase | *Myxococcus xanthus* MXAN_0191 *Stigmatella aurantiaca* STIAU_3334 | YP_628473.1 YP_003957653.1 |

The synthetic pathway disclosed in this invention serves as a platform for the generation of valuable chemical products from less valuable and more abundant hydrocarbon feedstocks. Methane, for example, can be converted into liquid "drop in" fuels for use in the current transportation infrastructure. The methods, materials and systems herein thus allow for various chain length hydrocarbons to be activated and assimilated into central carbon metabolism allowing for product synthesis via numerous native and synthetic pathways.

The process involves performing traditional cultures using industrial organisms (such as *E. coli, S. cerevisiae, Methylococcus capsulatus*, or *Pichia pactoris*) that convert short-chain hydrocarbons (such as methane, ethane, propane, butane, or pentane) into chemical products. These organisms are considered workhorses of modern biotechnology, and are easy to genetically engineer, and scale up for industrial production levels of desired products.

The pathways in a living system are generally made by transforming the microbe with an expression vector encoding one or more of the proteins, but the genes can also be added to the chromosome by recombineering, homologous recombination, and similar techniques. Where the needed protein is endogenous, as is the case in some instances, it may suffice as is, but it is usually overexpressed using an inducible promoter for better functionality and user-control over the level of active enzyme.

As used herein, the expressions "microorganism," "microbe," "strain" and the like may be used interchangeably and all such designations include their progeny. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

As used herein, reference to a "cell" is generally understood to include a culture of such cells, as the work described herein is done in cultures having $10^{9-15}$ cells.

As used herein, "growing" cells used it its art accepted manner, referring to exponential growth of a culture of cells, not the few cells that may not have completed their cell cycle at stationary phase or have not yet died in the death phase or after harvesting.

As used in the claims, "homolog" means an enzyme with at least 50% identity to one of the listed sequences and also having the same general catalytic activity. While higher identity (60%, 70%, 80%) and the like may be preferred, it is typical for bacterial sequences to diverge significantly (40-60%), yet still be identifiable as homologs, while mammalian species tend to diverge less (80-90%).

Reference to proteins herein can be understood to include reference to the gene encoding such protein. Thus, a claimed "permease" protein can include the related gene encoding that permease. However, it is preferred herein to refer to the protein by standard name per ecoliwiki or HUGO since both enzymatic and gene names have varied widely, especially in the prokaryotic arts.

Once an exemplary protein is obtained, many additional examples of proteins with similar activity can be identified by BLAST search. Further, every protein record is linked to a gene record, making it easy to design overexpression vectors. Many of the needed enzymes are already available in vectors, and can often be obtained from cell depositories or from the researchers who cloned them. But, if necessary, new clones can be prepared based on available sequence information using RT-PCR techniques. Thus, it should be easily possible to obtain all of the needed enzymes for overexpression.

Another way of finding suitable enzymes/proteins for use in the invention is to consider other enzymes with the same EC number, since these numbers are assigned based on the reactions performed by a given enzyme. An enzyme that thus be obtained, e.g., from AddGene or from the author of the work describing that enzyme, and tested for functionality as described herein. In addition, many sites provide lists of proteins that all catalyze the same reaction.

Understanding the inherent degeneracy of the genetic code allows one of ordinary skill in the art to design multiple nucleotides that encode the same amino acid sequence. NCBI™ provides codon usage databases for optimizing DNA sequences for protein expression in various species. Using such databases, a gene or cDNA may be "optimized" for expression in *E. coli*, yeast, algae or other species using the codon bias for the species in which the gene will be expressed.

Initial cloning experiments have proceeded in *E. coli* for convenience since most of the required genes are already available in plasmids suitable for bacterial expression, but the addition of genes to bacteria is of nearly universal applicability. Indeed, since recombinant methods were invented in the 70's and are now so commonplace, even school children perform genetic engineering experiments using bacteria. Such species include e.g., *Bacillus, Streptomyces, Azotobacter, Trichoderma, Rhizobium, Pseudomonas, Micrococcus, Nitrohacter, Proteus, Lactobacillus, Pediococcus, Lactococcus, Salmonella, Streptococcus, Paracoccus, Methanosarcina*, and *Methylococcus*, or any of the completely sequenced bacterial species. Indeed, hundreds of bacterial genomes have been completely sequenced, and this information greatly simplifies both the generation of vectors encoding the needed genes, as well as the planning of a recombinant engineering protocol. Such species are listed along with links at en.wikipedia.org/wiki/List_of_sequenced_bacterial_genomes.

Additionally, yeast, such as *Saccharomyces*, are a common species used for microbial manufacturing, and many species can be successfully transformed. Indeed, yeast are already available that express recombinant thioesterases—one of the termination enzymes described herein and the reverse beta oxidation pathway has also been achieved in yeast. Other species include but are not limited to *Candida, Aspergillus, Arxula adeninivorans, Candida boidinii, Hansenula polymorpha (Pichia angusta), Khuyveromyes lactis, Pichia pastoris*, and *Yarroivia lipolytica*, to name a few.

It is also possible to genetically modify many species of algae, including e.g., *Spirulina, Apergillus, Chlamydomonas, Laminaria japonica, Undaria pinnatifida, Porphyra, Eucheuma, Kappaphycus, Gracilaria, Monostroma, Enteromorpha, Arthrospira, Chlorella, Aphanizomenon, Isochrysis, Pavlova, Phaeodactylum, Ulkenia, Haematococcus, Chaetoceros, Nannochloropsis, Skeletonema, Thalassiosira,* and *Laminaria japonica*, and the like. Indeed, the microalga *Pavlova lutheri* is already being used as a source of economically valuable docosahexaenoic (DHA) and eicosapentaenoic acids (EPA), and *Crypthecodinium cohnii* is the heterotrophic algal species that is currently used to produce the DHA used in many infant formulas.

Furthermore, a number of databases include vector information and/or a repository of vectors and can be used to choose vectors suitable for the chosen host species. See e.g., AddGene.org which provides both a repository and a searchable database allowing vectors to be easily located and obtained from colleagues. See also Plasmid Information Database (PlasmID) and DNASU having over 191,000 plasmids. A collection of cloning vectors of *E. coli* is also kept at the National Institute of Genetics as a resource for the biological research community. Furthermore, vectors (including particular ORFS therein) are usually available from colleagues.

The enzymes can be added to the genome or via expression vectors, as desired. Preferably, multiple enzymes are expressed in one vector or multiple enzymes can be combined into one operon by adding the needed signals between coding regions. Further improvements can be had by overexpressing one or more, or even all of the enzymes, e.g., by adding extra copies to the cell via plasmid or other vector. Initial experiments may employ expression plasmids hosting 3 or more ORFs for convenience, but it may be preferred to insert operons or individual genes into the genome for long term stability.

Still further improvements in yield can be had by reducing competing pathways, such as those pathways for making e.g., acetate, formate, ethanol, and lactate, and it is already well known in the art how to reduce or knockout these pathways. See e.g., the Rice patent portfolio by Ka-Yiu San and George Bennett (U.S. Pat. Nos. 7,569,380, 7,262,046, 8,962,272, 8,795,991) and patents by these inventors (U.S. Pat. Nos. 8,129,157 and 8,691,552) (each incorporated by reference herein in its entirety for all purposes). Many others have worked in this area as well.

In calculating "% identity" the unaligned terminal portions of the query sequence are not included in the calculation. The identity is calculated over the entire length of the reference sequence, thus short local alignments with a query sequence are not relevant (e.g., % identity=number of aligned residues in the query sequence/length of reference sequence). Alignments are performed using BLAST homology alignment as described by Tatusova T A & Madden T L (1999) FEMS Microbiol. Lett. 174:247-250, and available through the NCBI website. The default parameters were used, except the filters were turned OFF.

"Operably associated" or "operably linked", as used herein, refer to functionally coupled nucleic acid or amino acid sequences.

"Recombinant" is relating to, derived from, or containing genetically engineered material. In other words, the genetics of an organism was intentionally manipulated in some way.

"Reduced activity" is defined herein to be at least a 75% reduction in protein activity, as compared with an appropriate control species (e.g., the wild type gene in the same host species). Preferably, at least 80, 85, 90, 95% reduction in activity is attained, and in the most preferred embodiment, the activity is eliminated (100%). Proteins can be inactivated with inhibitors, by mutation, or by suppression of expression or translation, by knock-out, by adding stop codons, by frame shift mutation, and the like. All reduced activity genes or proteins are signified herein by "−".

By "null" or "knockout" what is meant is that the mutation produces undetectable active protein. A gene can be completely (100%) reduced by knockout or removal of part of all of the gene sequence. Use of a frame shift mutation, early stop codon, point mutations of critical residues, or deletions or insertions, and the like, can also completely inactivate (100%) gene product by completely preventing transcription and/or translation of active protein. All null mutants herein are signified by Δ.

"Overexpression" or "overexpressed" is defined herein to be at least 150% of protein activity as compared with an appropriate control species, or any expression in a species that lacks the activity altogether. Preferably, the activity is increased 100-500% or even ten fold. Overexpression can be achieved by mutating the protein to produce a more active form or a form that is resistant to inhibition, by removing inhibitors, or adding activators, and the like. Overexpression can also be achieved by removing repressors, adding multiple copies of the gene to the cell, or up-regulating the endogenous gene, and the like. All overexpressed genes or proteins are signified herein by "+".

In certain species it is possible to genetically engineer the endogenous protein to be overexpressed by changing the regulatory sequences or removing repressors. However, overexpressing the gene by inclusion on selectable plasmids or other vectors that exist in hundreds of copies in the cell may be preferred due to its simplicity and ease of exerting externals controls, although permanent modifications to the genome may be preferred in the long term for stability reasons.

The terms "operably associated" or "operably linked," as used herein, refer to functionally coupled nucleic acid sequences.

As used herein "recombinant" is relating to, derived from, or containing genetically engineered material. In other words, the genome was intentionally manipulated by the hand of man in some way.

The term "endogenous" or "native" means that a gene originated from the species in question, without regard to subspecies or strain, although that gene may be naturally or intentionally mutated, or placed under the control of a promoter that results in overexpression or controlled expression of said gene. Thus, genes from Clostridia would not be endogenous to *Escherichia*, but a plasmid expressing a gene from *E. coli* or would be considered to be endogenous to any genus of *Escherichia*, even though it may now be overexpressed.

"Expression vectors" are used in accordance with the art accepted definition of a plasmid, virus or other propagatable sequence designed for protein expression in cells. There are thousands of such vectors commercially available, and typically each has an origin of replication (ori); a multiple cloning site; a selectable marker; ribosome binding sites; a promoter and often enhancers; and the needed termination sequences. Most expression vectors are inducible, although constitutive expressions vectors also exist.

As used herein, "inducible" means that gene expression can be controlled by the hand of man, by adding e.g., a ligand to induce expression from an inducible promoter. Exemplary inducible promoters include the lac operon, inducible by IPTG, the yeast AOX1 promoter inducible with methanol, the strong LAC4 promoter inducible with lactate, and the like. Low level of constitutive protein synthesis may occur even in expression vectors with tightly controlled promoters.

As used herein, an "integrated sequence" means the sequence has been integrated into the host genome, as opposed to being maintained on an expression vector. It will still be expressable, and preferably is inducible as well.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The following abbreviations are used herein:

| ABBREVIATION | TERM |
| --- | --- |
| ACP | Acyl carrier protein |
| Box-R | Beta oxidation pathway in reverse. |
| FAS | Fatty acid biosynthesis |
| GC | Gas chromatograph |
| HPLC | High pressure liquid chromatograph |
| ORF | Open reading Frame |

(R)-benzylsuccinate CoA-transferase (Q9KJF0, Q9KJE9); RsMcd: *R. sphaeroides* (2S)-methylsuccinyl-CoA dehydrogenase (ADC44452.1); RsMch: *R. sphaeroides* mesaconyl-coenzyme A hydratase (Q3IZ78).

Figure 11:
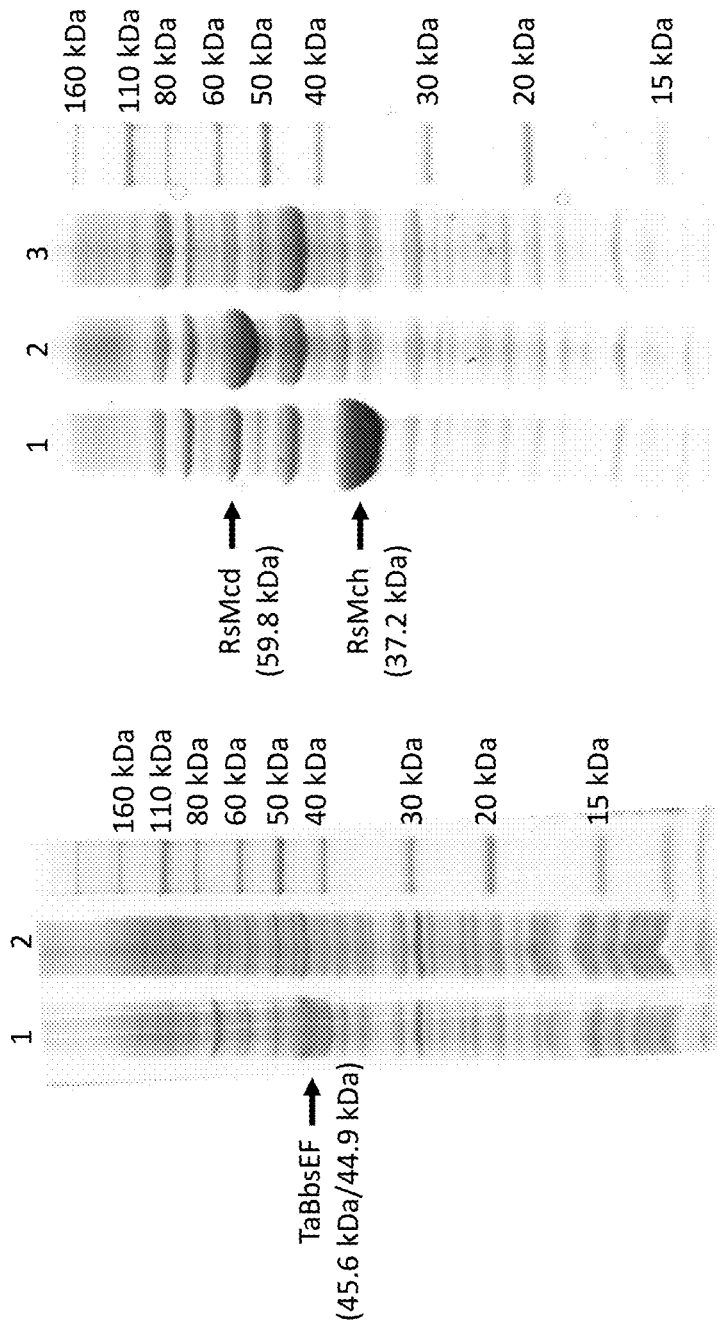

FIG. 11. Expression of enzymes involved in the oxygen-independent alkane utilization pathway. Left: Whole cell extract of *E. coli* cells expressing *T. aromatica* succinyl-CoA:(R)-benzylsuccinate CoA-transferase TaBbsEF (Q9KJF0, Q9KJE9), Lane 1: pCDFDuet-1-P1-TaBbsEF; Lane 2: pCDFDuet-1. Right: Soluble cell extract of *E. coli* cells expressing *R. sphaeroides* (2S)-methylsuccinyl-CoA dehydrogenase RsMcd (ADC44452.1) and *R. sphaeroides* mesaconyl-coenzyme A hydratase RsMch (Q3IZ78), Lane 1: pCDFDuet-1-P1-P2-RsMch-RsMcd; Lane 2: pCDFDuet-1-P1-P2-RsMch; Lane 3: pCDFDuet-1. RsMcd: *R. sphaeroides* (2S)-methylsuccinyl-CoA dehydrogenase (ADC44452.1); RsMch: *R. sphaeroides* mesaconyl-coenzyme A hydratase (Q3IZ78).

Figure 12:
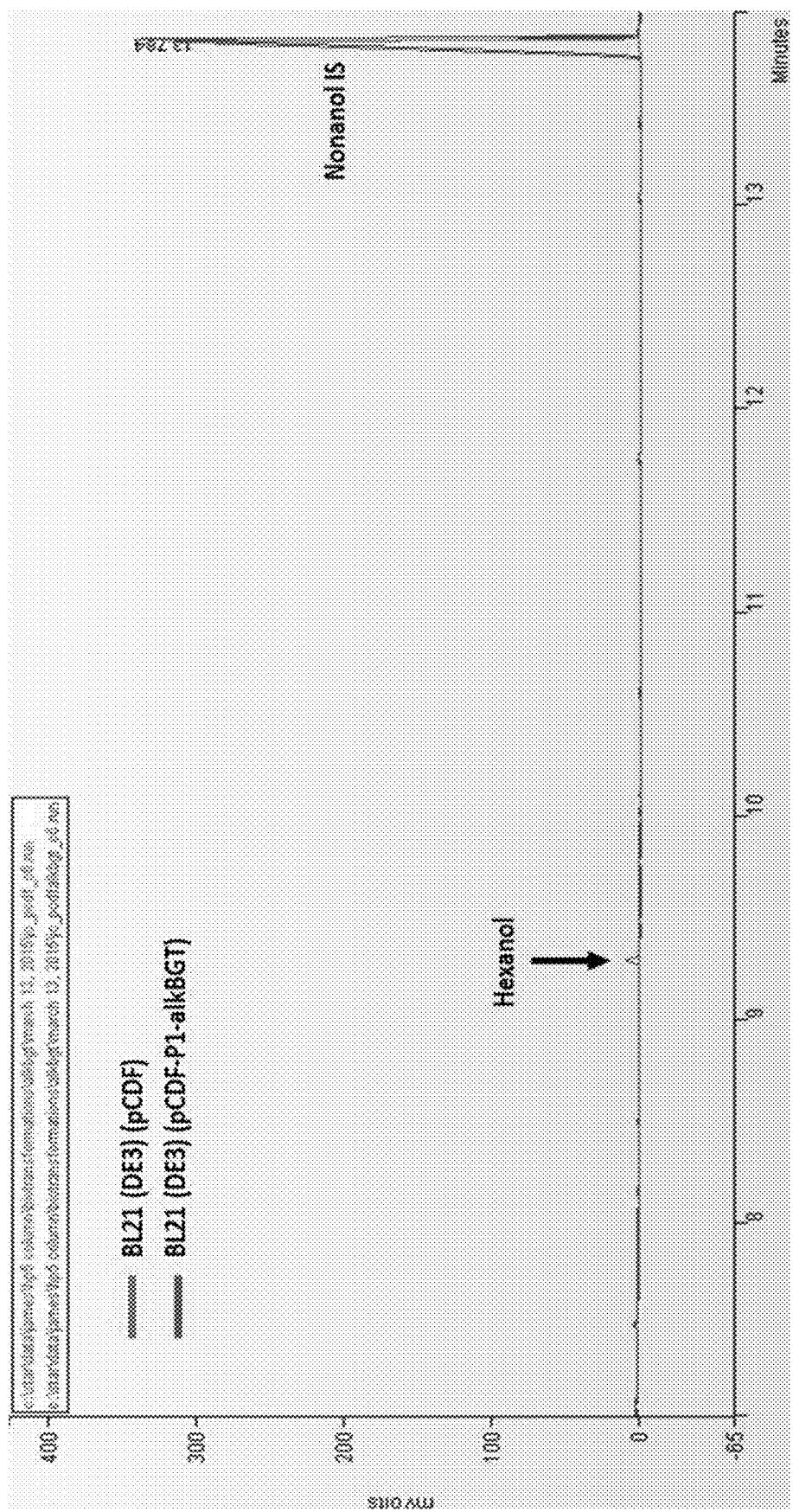

FIG. 12. Oxygen-dependent alkane activation of hexane with *P. putida* alkane hydroxylase AlkBGT. GC-FID chromatogram for products of whole cell biotransformation of BL21(DE3) cells with indicated vectors shown. 1 mL of cell suspension ($OD_{550\ nm}$=12) incubated with 250 µL hexane at 30° C. for 2 hours. Hexanol only observed only in cells expressing AlkBGT.

Figure 13:
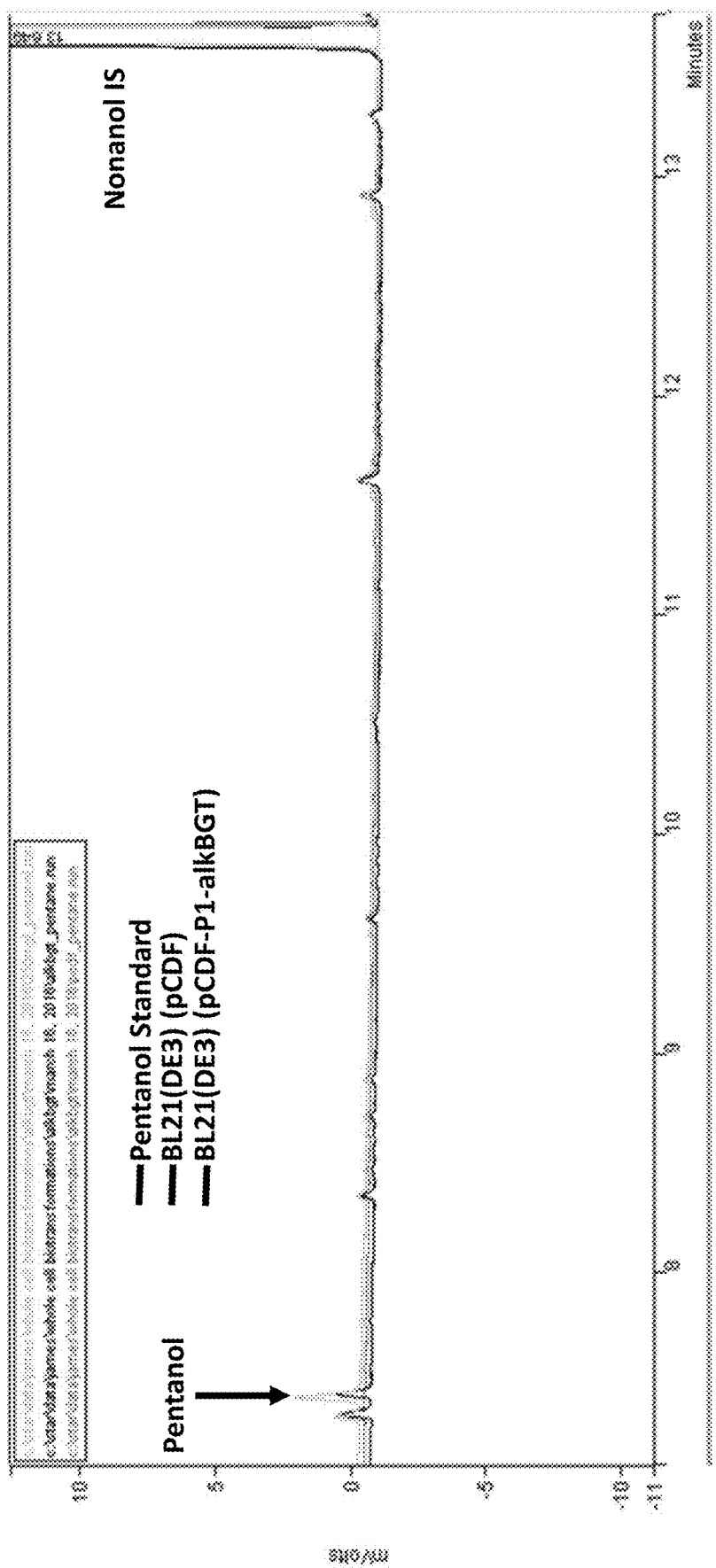

FIG. 13. Oxygen-dependent alkane activation of pentane with *P. putida* alkane hydroxylase AlkBGT. GC-FID chromatogram for products of whole cell biotransformation of BL21(DE3) cells with indicated vectors shown. 1 mL of cell suspension ($OD_{550\ nm}$=12) incubated with 250 µL pentane at 30° C. for 2 hours. Pentanol only observed only in cells expressing AlkBGT.

Figure 14A:
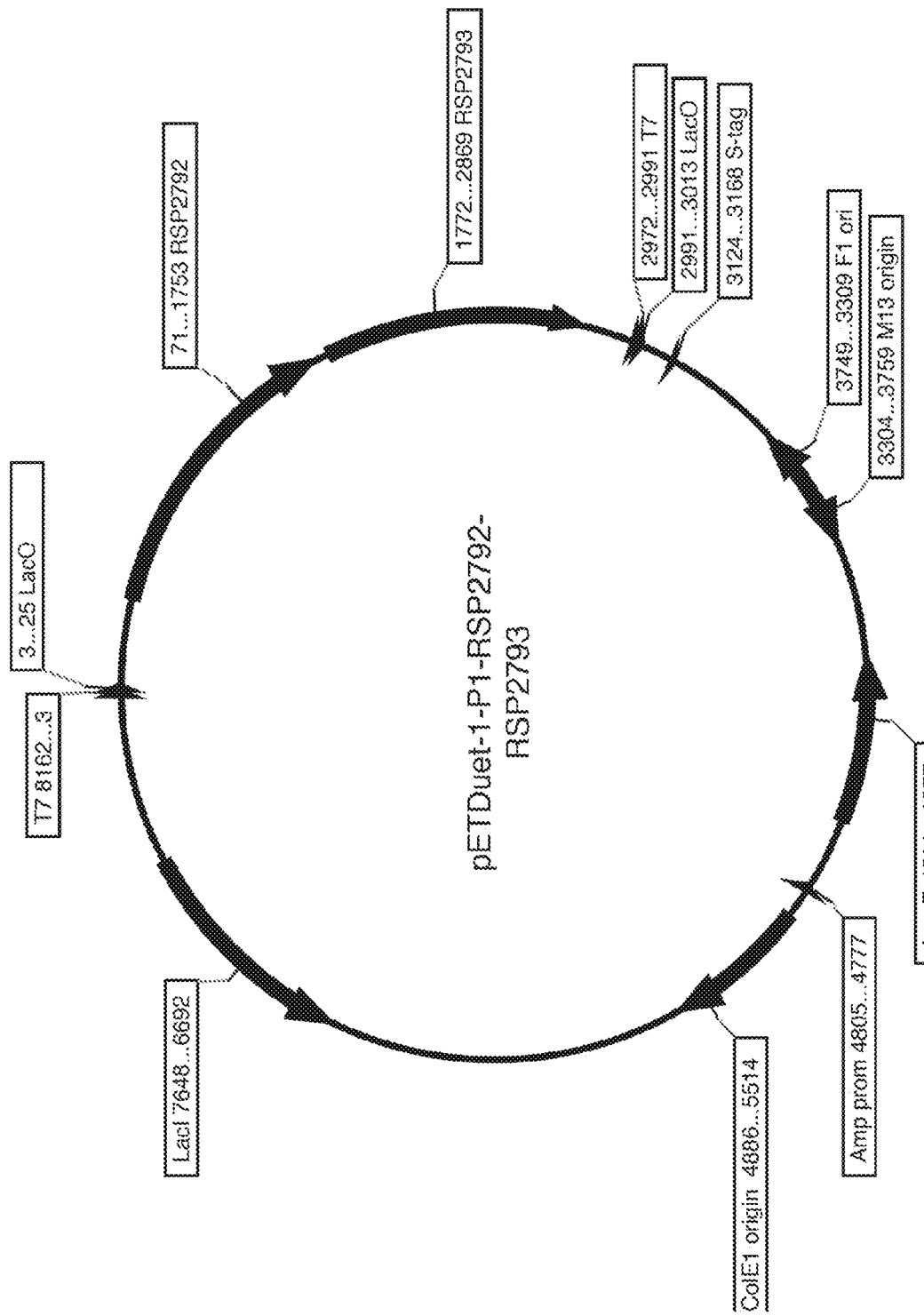
Figure 14B:
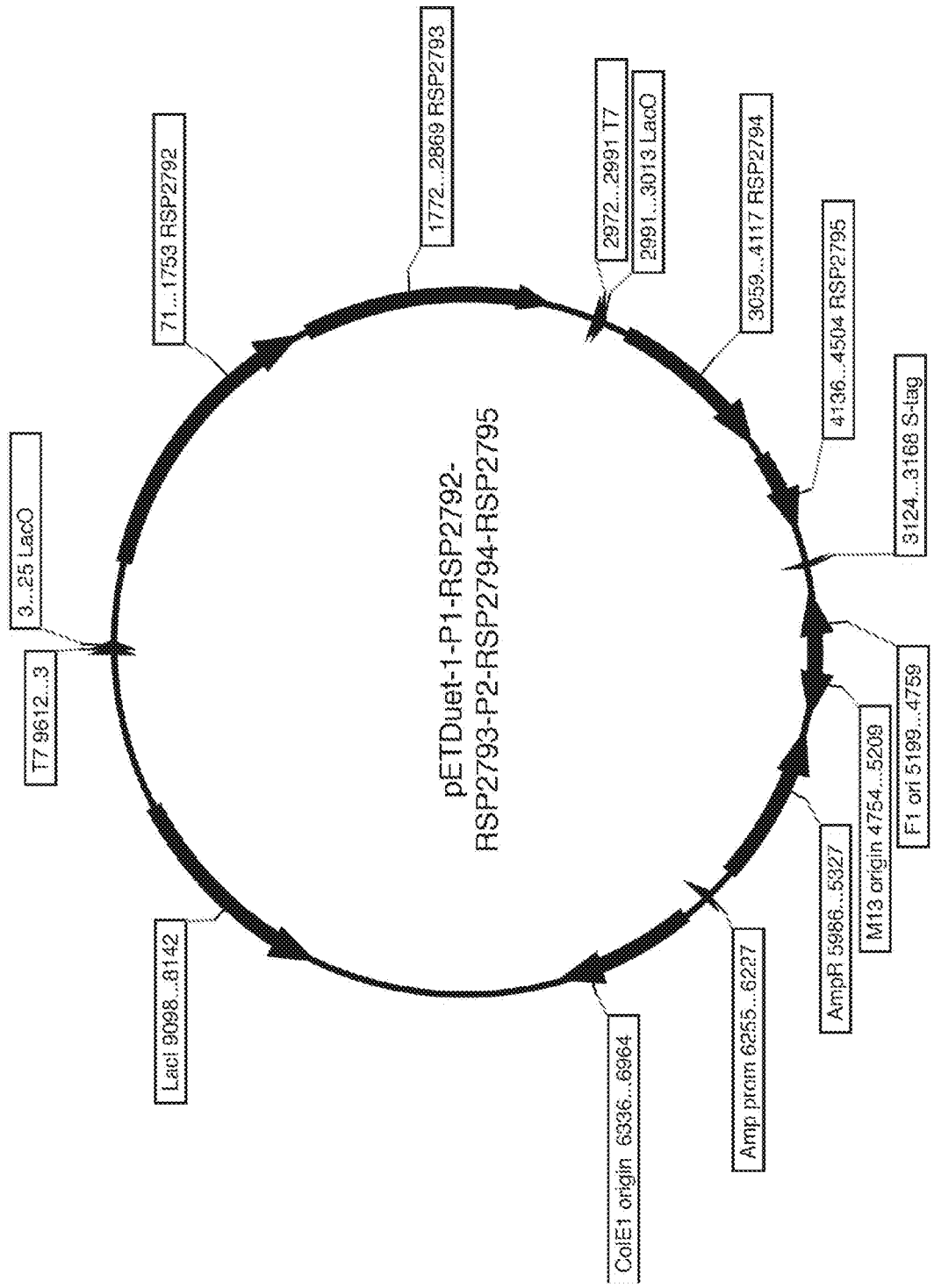

FIG. 14A-B. Vectors expressing the putative alkane monooxygenase from *Rhodobacter sphaeroides*. RSP2792: monooxygenase alpha subunit (YP_352924.1); RSP2793: monooxygenase reductase component (YP_352923.1); RSP2794: monooxygenase beta subunit (YP_352922.1); RSP2795: regulatory protein of multicomponent monooxygenase (YP_352921.1).

FIG. 15. TABLE G: list of some possible embodiments.

DETAILED DESCRIPTION

The activation of the short chain hydrocarbon substrates, such as methane of LNG components, requires the high stability and low reactivity of hydrocarbon compounds to be overcome through the cleavage of an inert C—H bond. Two main biological approaches can be exploited here for this purpose, 1) the oxygen-independent activation through the addition of fumarate to form a 2-methyl-alkyl-succinyl-CoA, or 2) the oxygen-dependent activation through the terminal addition of a hydroxyl group to the alkane to form a primary alcohol.

Figure 1:
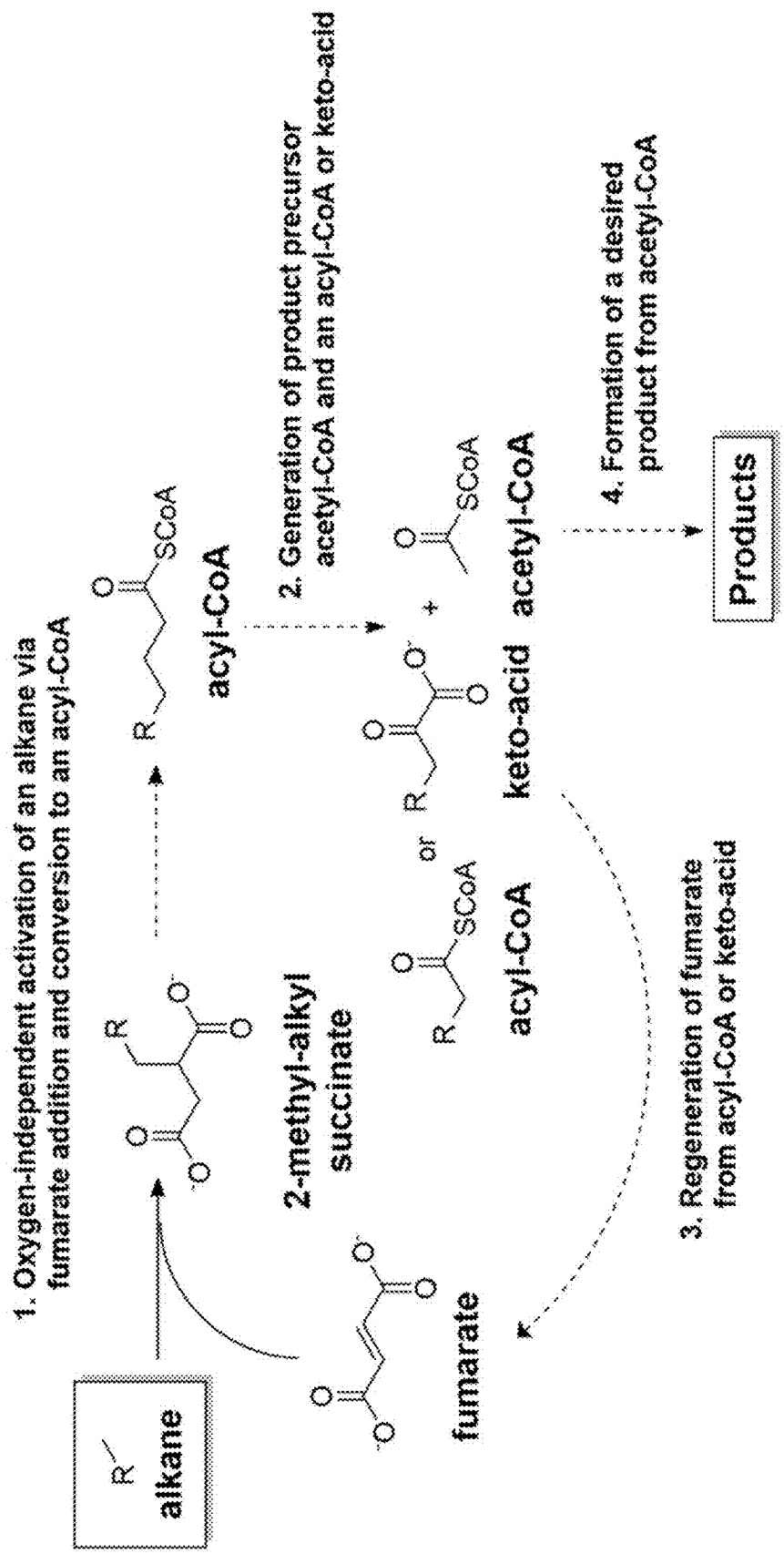
FIG. 1. Generalized pathway for the conversion of alkanes to desired products.
Figure 2:
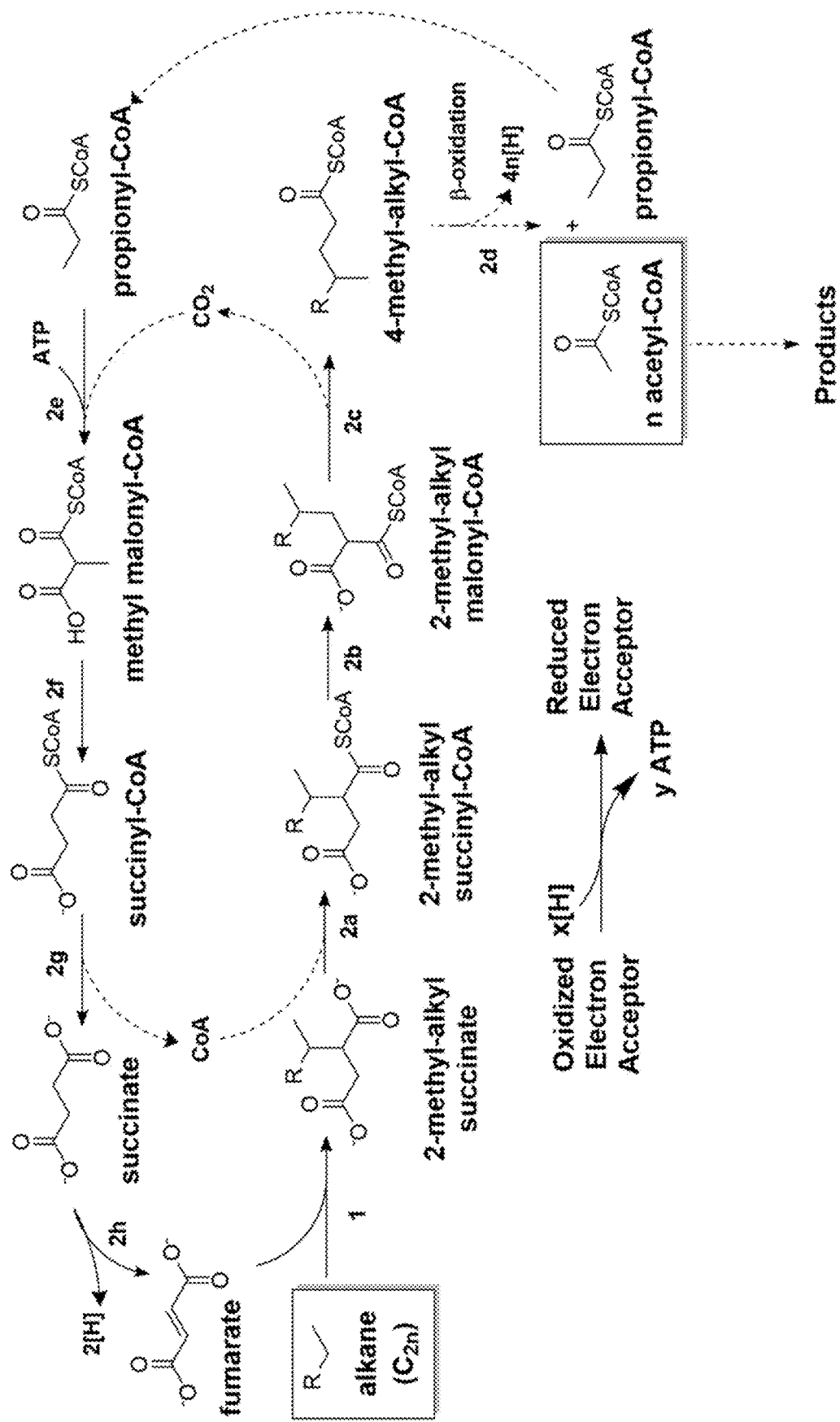
FIG. 2. Example of oxygen-independent alkane activation cycle via fumarate addition and conversion to an acyl-CoA, generation of product precursor acetyl-CoA and propionyl-CoA, regeneration of fumarate from propionyl-CoA, and generalized product formation from acetyl-CoA. Enzymes, 1: alkyl succinate synthase, 2a: succinyl-CoA:2-methyl-alkyl-succinyl-CoA transferase/2-methyl-alkyl-succinyl-CoA synthetase, 2b: 2-methyl-alkyl-malonyl-CoA mutase, 2c: 2-methyl-alkyl-malonyl-CoA decarboxylase, 2d: β-oxidation enzymes, 2e: propionyl-CoA carboxylase, 2f: methylmalonyl-CoA epimerase and methylmalonyl-CoA mutase, 2g: succinyl-CoA:2-methyl-alkyl-succinyl-CoA transferase/succinyl-CoA synthetase, 2h: succinate dehydrogenase.

The first approach leverages a native pathway for anaerobic hydrocarbon activation used by certain microorganisms for the degradation of $C_6$-$C_{20}$ alkanes (Callaghan, 2013). In this pathway, an alkyl-succinate synthase first forms a branched methyl-alkyl-succinate adduct from the addition of fumarate to the alkane, with further metabolism and fumarate regeneration steps resulting in the conversion of hydrocarbon substrates to central, intracellular metabolites (FIG. 2).

In order to meet ATP requirements of this cycle, native hydrocarbon degrading microorganisms utilize the electrons generated during substrate oxidation for anaerobic respiration with nitrate, metal ions, or sulfate, thereby making hydrocarbon degradation thermodynamically favorable (Mbadinga et al., 2011). An example of this type of process is found in strain HxN1, which can grow anaerobically on alkanes such as hexane when coupled to denitrification, with the key genes required for initial alkane activation proposed (Grundmann et al., 2008). Reports also have suggested similar activation with shorter chain hydrocarbons in bacterial consortiums, although the enzymes responsible have not been identified (Duncan et al., 2009; Kniemeyer et al., 2007).

Figure 3:
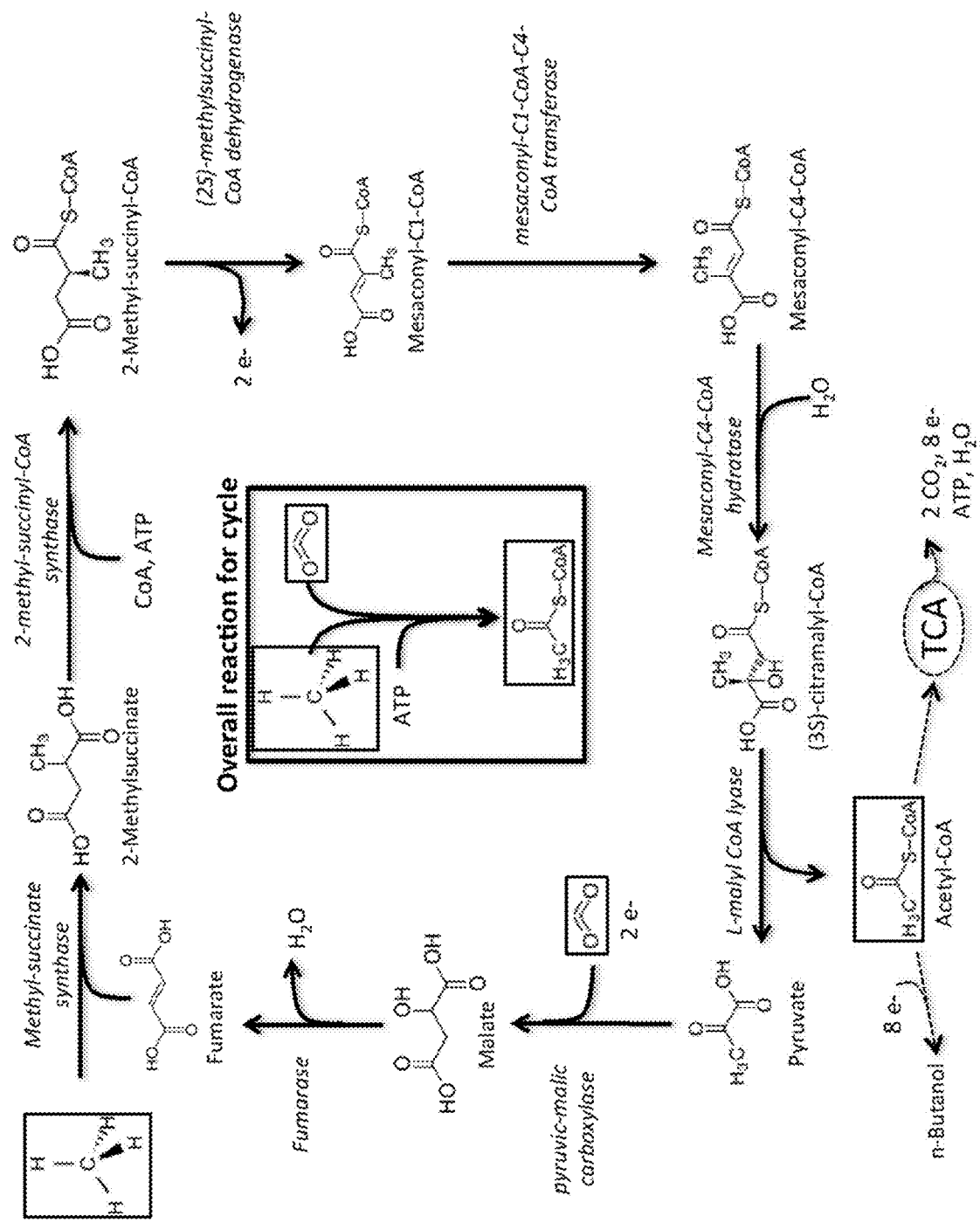
FIG. 3. Example of one specific oxygen-independent alkane activation cycle via fumarate addition and conversion to an acyl-CoA, generation of product precursor acetyl-CoA and pyruvate (a keto acid), regeneration of fumarate from pyruvate, and generalized product formation from acetyl-CoA.
Figure 4:
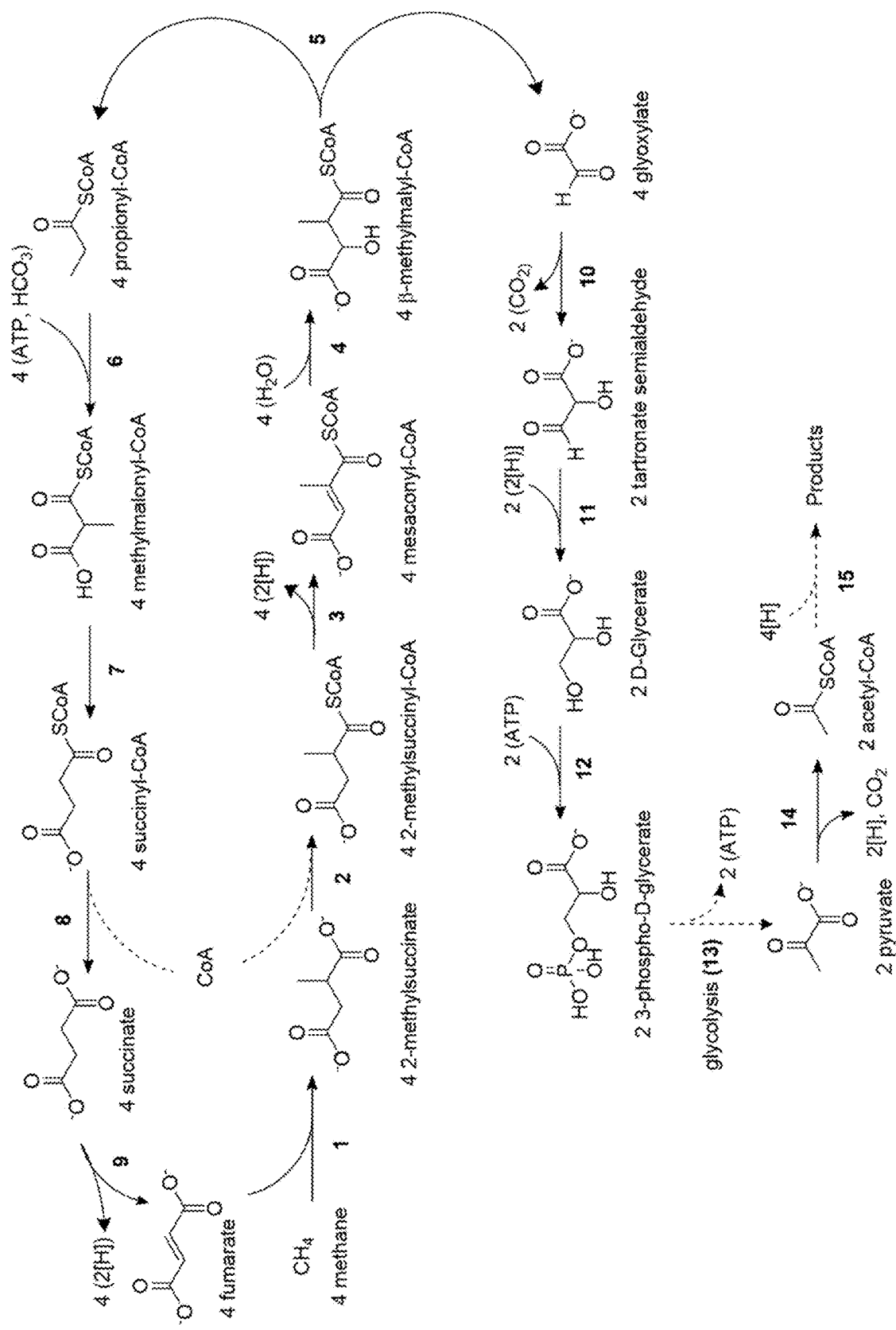
FIG. 4. Example of one specific oxygen-independent alkane activation cycle via fumarate addition and conversion to an acyl-CoA, generation of product precursor acetyl-CoA and propionyl-CoA, regeneration of fumarate from propionyl-CoA, and generalized product formation from acetyl-CoA. Enzymes, 1: methyl succinate synthase, 2: succinyl-CoA:2-methyl-alkyl-succinyl-CoA transferase/2-methyl-alkyl-succinyl-CoA synthetase, 3: 2-methyl-alkyl-succinyl-CoA dehydrogenase, 4: mesaconyl-CoA hydratase/β-methylmalyl-CoA dehydratase, 5: β-methylmalyl-CoA lyase, 6: propionyl-CoA carboxylase, 7: methylmalonyl-CoA epimerase and methylmalonyl-CoA mutase, 8: succinyl-CoA:2-methyl-alkyl-succinyl-CoA transferase/succinyl-CoA synthetase, 9: succinate dehydrogenase, 10: glyoxylate carboligase, 11: tartronate semialdehyde reductase, 12: glycerate kinase, 13: glycolytic enzymes (phosphoglycerate mutase, enolase, pyruvate kinase), 14: pyruvate dehydrogenase or pyruvate formate lyase, 15: β-oxidation reversal or fatty acid biosynthesis pathways with desired termination pathways.

Furthermore, several potential variations of this pathway exist in which various biological reactions can be utilized to convert the 2-methyl-alkyl-succinate adduct formed via fumarate addition into central metabolic intermediates (FIG. 3 and FIG. 4). Regardless of the pathway selected, the end result of the oxygen-independent hydrocarbon activation pathway is the formation of an acyl-CoA molecule that can be used to generate the product precursor acetyl-CoA. While in certain cases acetyl-CoA is directly formed as a result of initial acyl-CoA formation (FIG. 3 and FIG. 4), other initial acyl-CoA intermediates require further oxidation for the generation of acetyl-CoA (FIG. 2). In all cases, the end result is the generation of acetyl-CoA to serve as a product precursor, as well as another acyl-CoA of keto-acid compound that can be used for fumarate regeneration.

Considering the use of fumarate in the alkane activation cycle, this oxygen-independent activation approach also requires pathways for the regeneration of this compound from an acyl-CoA or keto-acid. Details on the pathways leading to the regeneration of fumarate from an acyl-CoA, such as propionyl-CoA, or a keto-acid, such as pyruvate, are shown in FIG. 2, FIG. 3, and FIG. 4. This regeneration enables the continued operation of the hydrocarbon activation cycle via fumarate addition.

Figure 5:
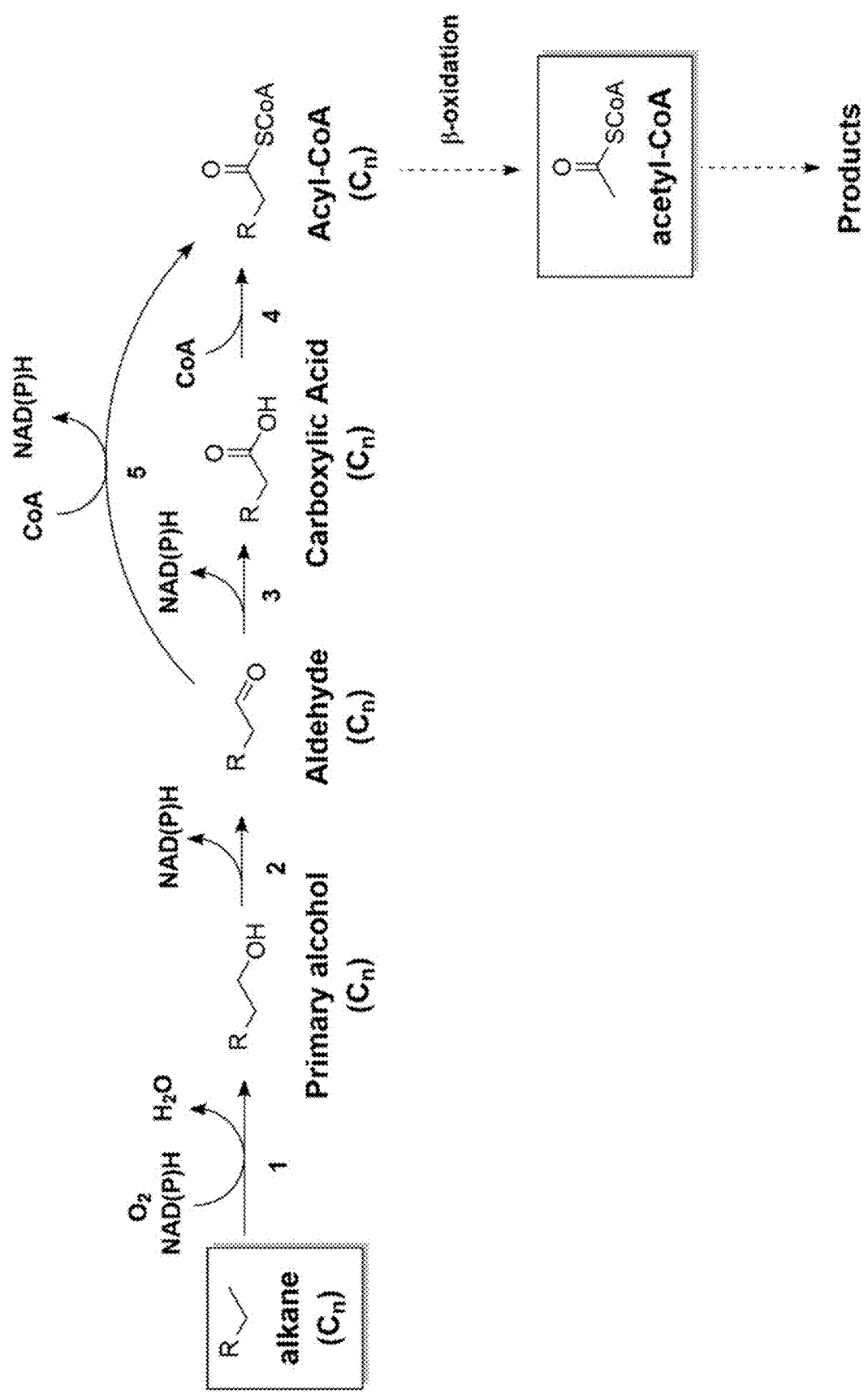
FIG. 5. Oxygen-dependent alkane activation via terminal addition of a hydroxyl group to a primary alcohol and conversion to acyl-CoA, generation of precursor acetyl-CoA, and generalized product synthesis from acetyl-CoA. Enzymes, 1: alkane monooxygenase or alkane hydroxylase, 2: alcohol dehydrogenase, 3: aldehyde dehydrogenase, 4: acyl-CoA synthetase, 5: acylating aldehyde dehydrogenase.
Figure 6A:
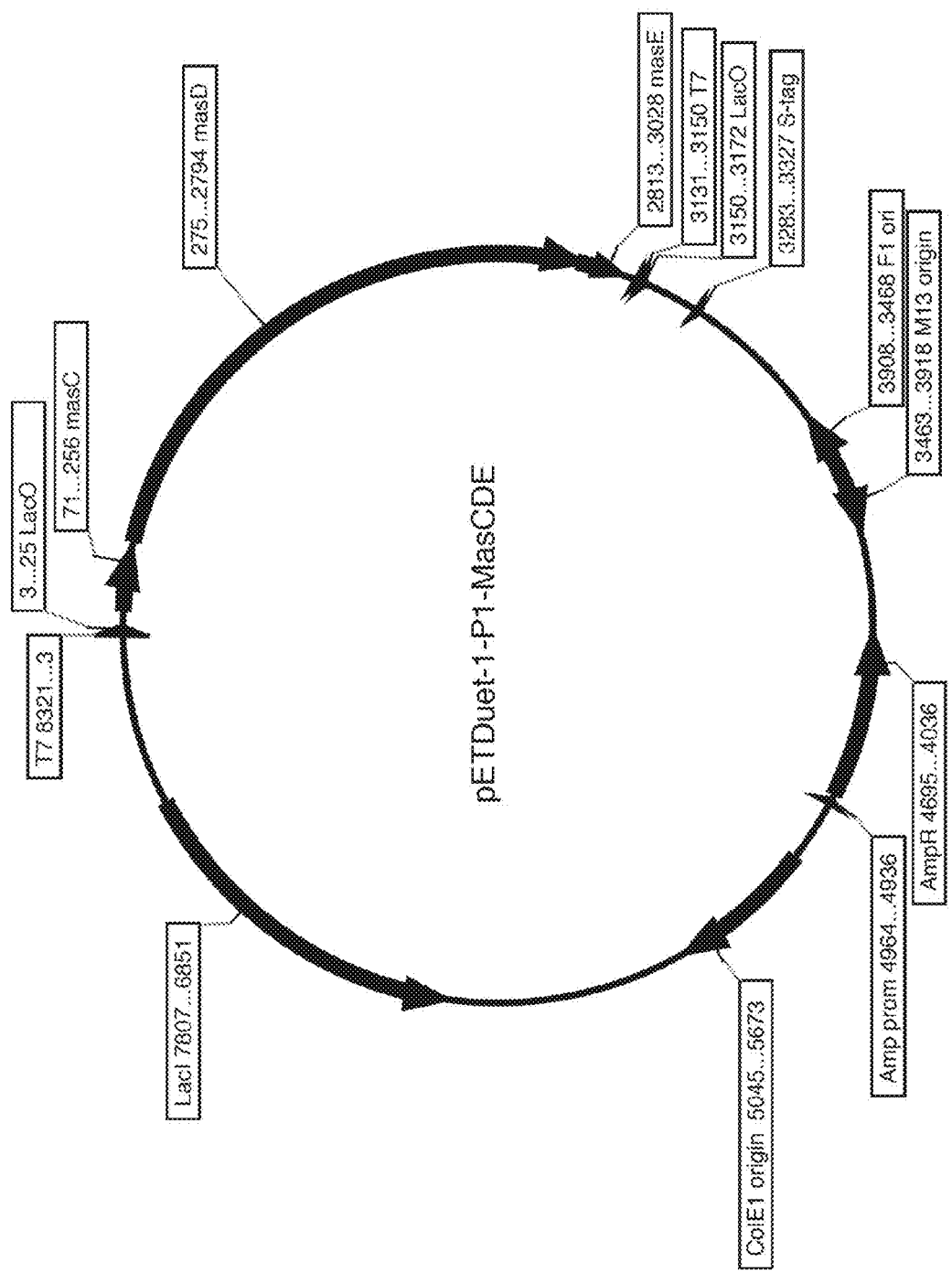
FIG. 6A-D. Vectors expressing the components of the oxygen-independent activation enzyme alkyl-succinate synthase from *Azoarcus* sp. HxN1, MasB (A9J4K0), MasC (A9J4K2), MasD (A9J4K4), MasE (A9J4K6), and MasG (A9J4J6) have been proposed as required components for enzyme function.
Figure 6B:
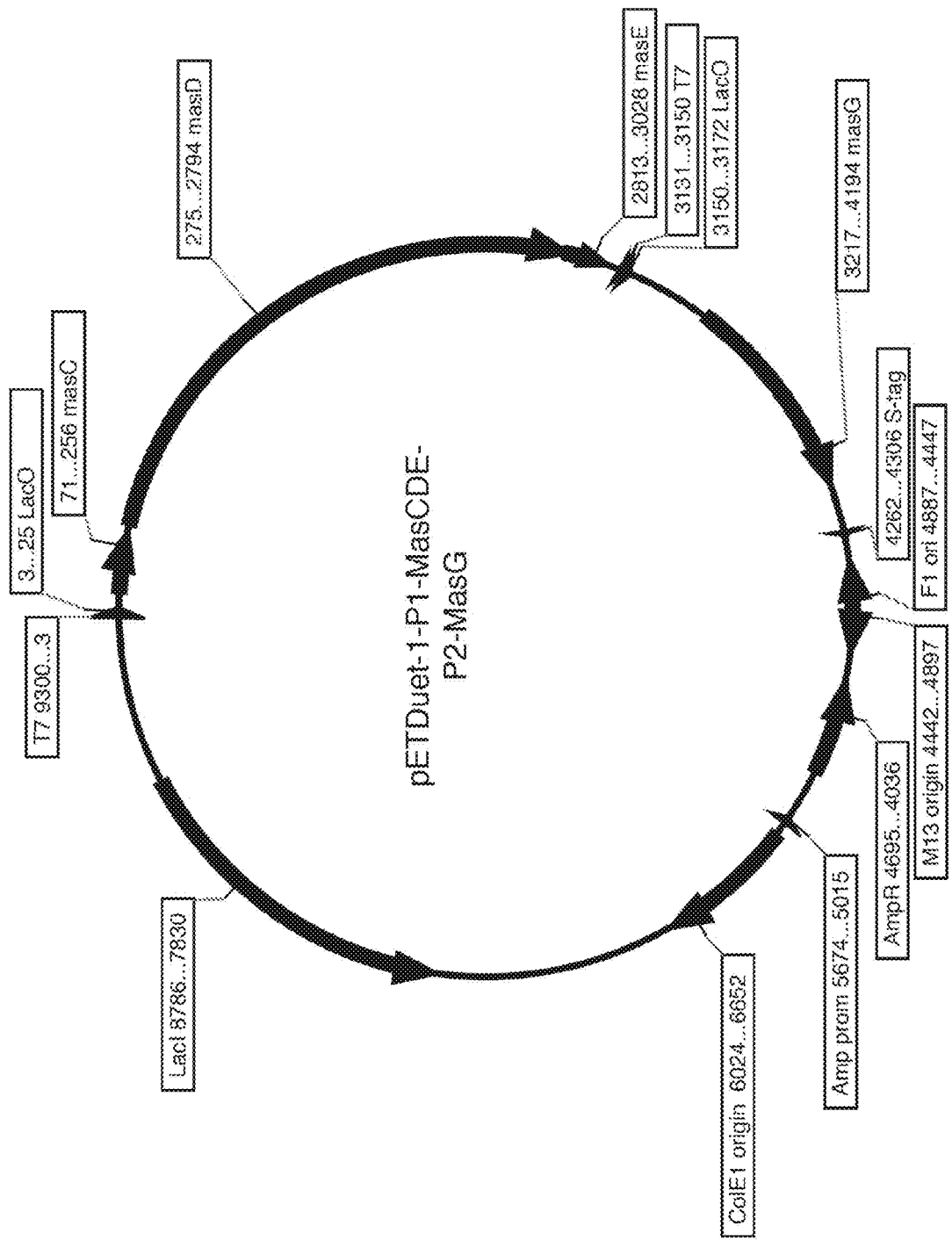
Figure 6C:
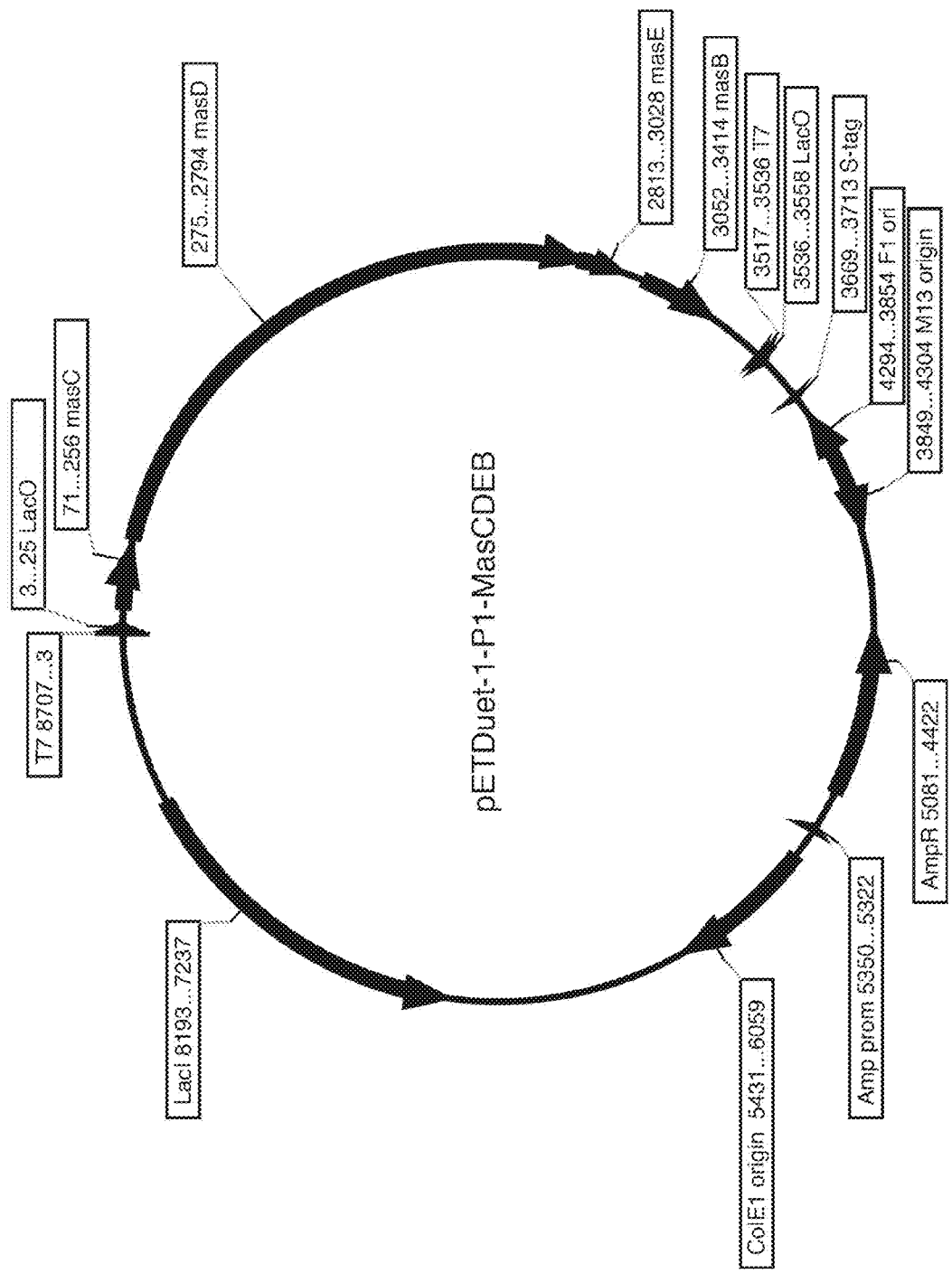
Figure 6D:
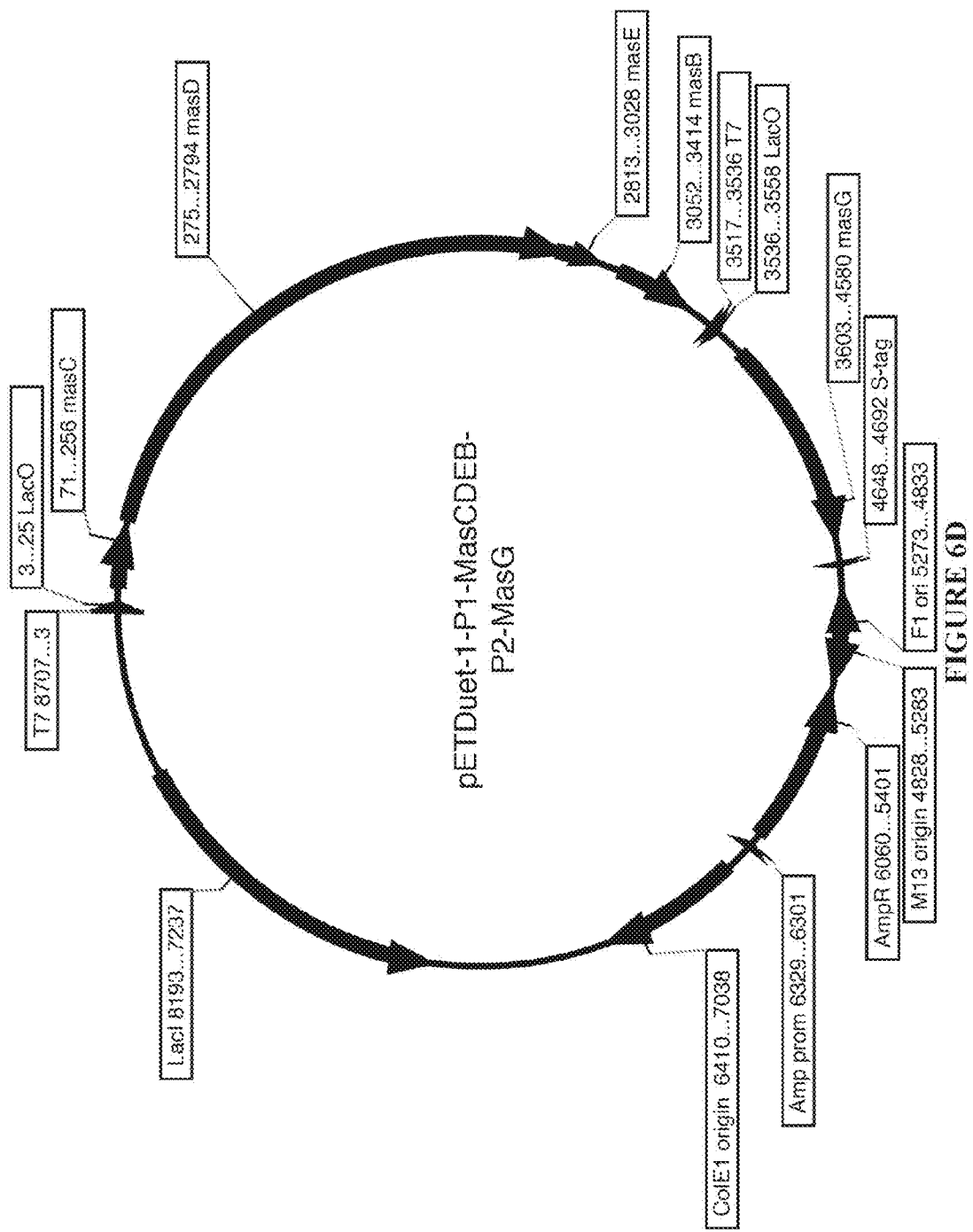

In contrast to hydrocarbon activation via fumarate addition, an alternative pathway for the cleavage of an inert C—H bond is the use of an oxygen-dependent activation mechanism in which an alkane hydroxylase/monooxygenase adds a terminal alcohol group to the hydrocarbon, which is then further oxidized (FIG. 5). The end result of the oxygen-dependent activation pathway is an acyl-CoA intermediate than can be used for the generation of the product precursor acetyl-CoA. Given the direct use of oxygen in this pathway for activation, no additional pathways are required to regenerate an activation compounds as in the above oxygen-independent approach.

Once the product precursor acetyl-CoA has been formed through the above described approaches, the desired products can then be synthesized through various native or engineered metabolic pathways. These include both the reversal of the β-oxidation cycle and the fatty acid biosynthesis pathway, which both proceed from acetyl-CoA as the starting compound. While the type of condensation reaction for chain elongation varies between the 2 pathways (reversal of the β-oxidation cycle utilizes a non-decarboxylative condensation while the fatty acid biosynthesis pathway employs a decarboxylative condensation), both proceed through a series of condensation, reduction, dehydration, and reduction reactions that result in an intermediate 2 carbons longer than the starting unit. As such, each of these pathways can be exploited for the synthesis of a wide range of products through the selection of termination pathways that convert cycle intermediates to products such as carboxylic acids and alcohols among others.

Thus, either of these product synthesis pathways, combined with the key pathway modules for hydrocarbon activation and conversion to an acyl-CoA intermediate, generation of product precursor acetyl-CoA, and generation of an addition acyl-CoA or keto-acid for fumarate when required, and the formation of a desired product from acetyl-CoA enables an engineered microorganism capable of the conversion of short-chain hydrocarbons (e.g. methane, ethane, propane, butane, pentane) to fuels and chemicals (e.g. carboxylic acids, alcohols, hydrocarbons, and their alpha-, beta-, and omega-functionalized derivatives).

The following description provides additional details, any one of which can be subject to patenting in combination with any other. The specification in its entirety is to be treated as providing a variety of details that can be used interchangeably with other details, as the specification would be of inordinate length if one were to list every possible combination of genes/vectors/enzymes/hosts that can be made to convert short chain hydrocarbons to desired fuels and chemicals of interest. Some possible combinations are listed in Table G, however, (FIG. 15).

Enzymes of interest can be expressed from vectors such as pETDuet-1 or pCDFDuet-1 (MERCK, Germany), which makes use of the DE3 expression system. Genes can be codon optimized according to the codon usage frequencies of the host organism and synthesized by a commercial vendor or in-house. However, thousands of expression vectors and hosts are available, and this is a matter of convenience.

The genes can be amplified by PCR using primers designed with 15-22 base pairs of homology for the appropriate vector cut site. For enzymes that will not require a 6×-histidine tag fusion for purification, pCDFDuet-1 can be linearized with NcoI and EcoRI. Enzymes that will be purified by Ni-NTA column will make use of the 6×-HIS tag in pCDFDuet-1. The vector can be linearized using only EcoRI in this case.

The PCR product can be inserted into the vector using e.g., the In-Fusion HD EcoDry Cloning System and the vector transformed by heat shock into competent $E.$ $coli$ cells. Transformants can be selected on solid media containing the appropriate antibiotic. Plasmid DNA can be isolated using any suitable method, including QIAprep Spin Miniprep Kit (QIAGEN, Limburg), and the construct confirmed by PCR and sequencing. Confirmed constructs can be transformed by e.g., electroporation into a host strain such as $E.$ $coli$ for expression, but other host species can be used with suitable expression vectors and possible codon optimization for that host species.

Expression of the desired enzymes from the constructed strain can be conducted in liquid culture, e.g., shaking flasks, bioreactors, chemostats, fermentation tanks and the like. Gene expression is typically induced by the addition of a suitable inducer, when the culture reaches an $OD_{550\ nm}$ of approximately 0.5-0.8. Induced cells can be grown for about 4-8 hours, at which point the cells can be pelleted and saved to −20° C. Expression of the desired protein can be confirmed by running samples on SDS-PAGE.

The expressed enzyme can be directly assayed in crude cell lysates, simply by breaking the cells by chemical, enzymatic, heat or mechanical means. Depending on the expression level and activity of the enzyme, however, purification may be required to be able to measure enzyme activity over background levels. Purified enzymes can also allow for the in vitro assembly of the pathway, allowing for its controlled characterization.

N- or C-terminal HIS-tagged proteins can be purified using e.g., a Ni-NTA Spin Kit (Qiagen, Venlo, Limburg) following the manufacturer's protocol, or other methods could be used. The HIS-tag system was chosen for convenience only, and other tags are available for purification uses. Further, the proteins in the final assembled pathway need not be tagged if they are for in vivo use. Tagging was convenient, however, for the enzyme characterization work performed hereunder.

Reaction conditions for enzyme assays can vary greatly with the type of enzyme to be tested. In general, however, enzyme assays follow a similar general protocol. Purified enzyme or crude lysate is added to suitable reaction buffer. Reaction buffers typically contain salts, necessary enzyme cofactors, and are at the proper pH. Buffer compositions often change depending on the enzyme or reaction type. The reaction is initiated by the addition of substrate, and some aspect of the reaction related either to the consumption of a substrate or the production of a product is monitored.

Choice of the appropriate monitoring method depends on the compound to be measured. Spectrophotometric assays are convenient because they allow for the real time determination of enzyme activity by measuring the concentration dependent absorbance of a compound at a certain wavelength. There are not always compounds with a measurable absorbance at convenient wavelengths in the reaction, unfortunately. In these situations, other methods of chemical analysis may be necessary to determine the concentration of the involved compounds.

As an example, cultures for enzymatic assays were conducted in 125 mL Erlenmeyer flasks containing 25 mL LB media inoculated at 3% from an overnight culture. $E.$ $coli$ strains containing constructs expressing genes of interest were grown under appropriate conditions until an optical density of ~0.5 was reached, at which point inducer(s) were added and the cells incubated for an additional 4 hrs. Cell harvesting and preparation of crude cell extracts for enzyme assays was conducted as described elsewhere (Dellomonaco et al., 2011). Enzymatic reactions were then monitored on either a Synergy HT plate reader (BioTek Instruments, Inc., Winooski, VT) or a Biomate 5 Spectrophotometer (Thermo Scientific, Waltham, MA) according to established protocols.

Furthermore, whole cell biotransformations represent another method to determine enzyme/pathway functionality. As an example, biotransformations for alkane activation were conducted using $E.$ $coli$ BL21(DE3) with appropriate vectors. 750 μL of an overnight LB culture with appropriate antibiotics was used to inoculate 25 mL LB media with 10 μM $FeSO_4$ in a 125 mL Pyrex Erlenmeyer flask. Flasks were incubated at 37° C. and 200 rpm in an NBS Benchtop Incubator Shaker until an optical density of ~0.5 was reached, at which point appropriate inducers were added. Cultures were grown for 4 hrs post-induction and then centrifuged (8000 rpm, 22° C., 5 min) and re-suspended to an optical density ~12 in 100 mM $KP_i$ buffer (pH 7.0) with 1% glycerol (Koch et al., 2009). 250 μL alkane was then added to a 2 mL cell suspension in a 5 mL glass vial and incubated with rotation (60 rpm) at 30° C. for 2 hrs, Following the biotransformations, products (alcohols) were extracted and analyzed as previously described (Kim et al., 2015).

Gas chromatography (GC) is convenient for the quantification of volatile substances, of which fatty acids and alcohols are of particular relevance. Internal standards, typically one or more molecules of similar type not involved in the reaction, are added to the reaction mixture, and the reaction mixture is extracted with an organic solvent, such as hexane. Fatty acid samples, for example, can be dried under a stream of nitrogen and converted to their trimethylsilyl derivatives using N,O-Bis(trimethylsilyl)trifluoroacetamide (BSTFA) and pyridine in a 1:1 ratio. After 30 minutes incubation, the samples are once again dried and resuspended in hexane to be applied to the gas chromatograph (GC). Aldehyde samples do not need to be derivatized. Samples can be run e.g., on a Varian CP-3800 gas chromatograph (VARIAN ASSOCIATES, Palo Alto, CA) equipped with a flame ionization detector and HP-5 capillary column (AGILENT TECH., CA).

Once pathways have been fully studied in vitro, they can be constructed in vivo with greater confidence. The strain construction for the in vivo pathway operation should allow for the well-defined, controlled expression of the enzymes of the pathway. As before, E. coli or yeast will be a host of choice for the in vivo pathway, but other hosts could be used. The Duet system, for example, allows for the simultaneous expression of up to eight proteins by induction with IPTG in E. coli, and initial experiments will use this host.

Pathway enzymes can also be inserted into the host chromosome, allowing for the maintenance of the pathway without requiring antibiotics to ensure the continued upkeep of plasmids. A large number of genes that can be placed on the chromosome, as chromosomal expression does not require separate origins of replication as is the case with plasmid expression.

DNA constructs for chromosomal integration usually include an antibiotic resistance marker with flanking FRT sites for removal, as described by Datsenko and Wanner, a well characterized promoter, a ribosome binding site, the gene of interest, and a transcriptional terminator. The overall product is a linear DNA fragment with 50 base pairs of homology for the target site on the chromosome flanking each side of the construct.

However, the Flp-FRT recombination method is only one system for adding genes to a chromosome, and other systems are available, such as the RecBCD pathway, the RecF pathway, RecA recombinase, non-homologous end joining (NHEJ), Cre-Lox recombination, TYR recombinases and integrases, SER resolvases/invertases, SER integrases, PhiC31 Integrase, and the like. Chromosomal modifications in E. coli can also achieved by the method of recombineering, as originally described by Datsenko and Wanner.

In a recombineering method, for example, the cells are prepared for electroporation following standard techniques, and the cells transformed with linear DNA that contains flanking 50 base pair targeting homology for the desired modification site. For seamless integration of a DNA construct, a two-step approach can be taken using a cassette that contains both positive and negative selection markers, such as the combination of cat and sacB. In the first round of recombineering, the cat-sacB cassette with targeting homology for the desired modification site is introduced to the cells. The cat gene provides resistance to chloramphenicol, which allows for positive recombinants to be selected for on solid media containing chloramphenicol.

A positive isolate can be subjected to a second round of recombineering introducing the desired DNA construct with targeting homology for sites that correspond to the removal of the cat-sacB cassette. The sacB gene encodes for an enzyme that provides sensitivity to sucrose. Thus, growth on media containing sucrose allows for the selection of recombinants in which the cat-sacB construct was removed. P1 phage lysates can be made from isolates confirmed by PCR and sequencing. The lysates can be used to transduce the modification into desired strains, as described previously.

Engineered strains expressing the designed pathway can be cultured under the following or similar conditions. Overnight cultures started from a single colony can be used to inoculate flasks containing appropriate media. Cultures are grown for a set period of time, and the culture media analyzed. The conditions will be highly dependent on the specifications of the actual pathway and what exactly is to be tested. For example, the ability for the pathway to be used for hydrocarbon utilization can be tested by the use of short-chain alkanes as a substrate in MOPS minimal media, as described by Neidhardt, supplemented with appropriate antibiotics, and inducers.

Analysis of culture media after fermentation provides insight into the performance of the engineered pathway. Quantification of hydrocarbons and longer chain fatty acid and alcohol products can be analyzed by GC. Other metabolites, such as short chain organic acids and alcohols can be analyzed by high pressure liquid chromatograph (HPLC). Once the pathway is fully functional, the cultures can be grown in chemostat, providing continuous uninterrupted production of product if desired.

Various -omics techniques, such as microarray or 2D-PAGE can give information about gene expression or protein expression, respectively. Genome scale modeling allows for the identification of additional modifications to the host strain that might lead to improved performance. Deletion of competing pathways, for example, might increase carbon flux through the engineered pathway for product production.

Standard molecular biology techniques were used for gene cloning, plasmid isolation, and E. coli transformation. Native E. coli genes were amplified from E. coli MG1655 genomic DNA using primers to append 15 bp of homology on each end of the gene insert for recombination into the vector backbone. Genes from other organisms were codon optimized and synthesized by either GeneArt (LIFE TECH., CA or GENSCRIPT, NJ). Plasmids were linearized by the appropriate restriction enzymes and recombined with the gene inserts using the In-Fusion HD Eco-Dry Cloning system (CLONTECH LAB. CA). The mixture was subsequently transformed into Stellar competent cells (CLONTECH LAB.).

Transformants that grew on solid media (LB+Agar) supplemented with the appropriate antibiotic were isolated and screened for the gene insert by PCR. Plasmid was isolated from the verified transformants and the sequence of the gene insert was further confirmed by DNA sequencing (LONE STAR LABS, TX). Plasmids (also referred to as vectors) in each case contain at least one promoter, a ribosome binding site for each gene, the gene(s) of interest, at least one terminator, an origin of replication, and an antibiotic resistance marker. Exemplary plasmids are shown in FIGS. 6A-D, 8A-C, 9A-C, 10A-C and 14.

Genes that encode the enzymes of the engineered pathway were cloned and expressed as described above. The crude protein extracts or purified enzymes were assessed for their ability to catalyze the proposed reactions. Tables β-F below describe the characterization of enzymes for required pathway steps depicted in FIG. 2, FIG. 3, FIG. 4, and FIG. 5. In addition to the experimental data provided, several literature examples are listed to provide additional evidence to the ability of known enzymes to possess the required enzymatic activity of several pathway steps. Thus, a great variety of enzymes are exemplified herein.

TABLE B describes the characterization of enzymes involved in hydrocarbon activation/utilization and conversion to acyl-CoA intermediates through the fumarate addition pathway as depicted in FIG. 2.

TABLE B

Characterization of enzymes involved in the pathway for bioconversion of hydrocarbons via fumarate addition as depicted in FIG. 2

| Enzyme Number | Enzyme class | Enzyme | Substrate | Measured specific activity (µmol/mg protein/min) | Reference |
|---|---|---|---|---|---|
| 1 | alkylsuccinate synthase | | See Table C for details | | |
| 2a | succinyl-CoA: 2-methyl-alkyl-succinyl-CoA transferase/2-methyl-alkyl-succinyl-CoA synthetase | T. aromatica BSCT | Methylsuccinate and succinyl-CoA | Methylsuccinyl-CoA formation observed | Leutwein and Heider (2001) |
| 2b | 2-methyl-alkyl-malonyl-CoA mutase | R. Sphaeroides Ecm | ethylmalonyl-CoA | 0.05, $K_m$: 60 µM (methylsuccinyl-CoA product) | Erb et al (2008) |
| 2c | 2-methyl-alkyl-malonyl-CoA decarboxylase | M. musculus ECHDC1 | ethylmalonyl-CoA | 8800, $K_m$: 0.96 µM | Linster et al (2011) |
| | | | methylmalonyl-CoA | $K_m$: 3.1 µM | Linster et al (2011) |
| 2e | propionyl-CoA carboxylase | M. sedula Pcc | propionyl-CoA | 3.3, $K_m$: 70 µM (75° C.) | Hugler et al (2003) |
| | | S. coelicolor Pcc | propionyl-CoA | 0.2, $K_m$: 76 µM | Arabolaza et al (2010) |
| 2f | methylmalonyl-CoA epimerase | P. horikoshii Mce | (S)-2-methylmalonyl-CoA | 162, $K_m$: 79 µM | Bobik and Rasche (2004) |
| | methylmalonyl-CoA mutase | P. freudenreichii subsp. shermanii Mcm | (R)-2-methylmalonyl-CoA | 26, $K_m$: 124 µM | Chowdhury et al (1999); Padovani et al (2006) |
| 2g | succinyl-CoA:2-methyl-alkyl-succinyl-CoA transferase/succinyl-CoA synthetase | E. coli SucCD | Succinate (reversible reaction) | 18.6, $K_m$: 141 µM | Nolte at al (2014) |
| 2h | succinate dehydrogenase | E. coli SdhCDAB | succinate | $K_m$: 2.5 µM | Maklashina at al (2001) |
| 2d: β-oxidation enzymes | | | | | |
| — | Acyl-CoA dehydrogenase | E. coli FadE | butyryl-CoA | 0.008 ± 0.001 | This work |
| — | Enoyl-CoA hydratase | E. coli FadB | crotonyl-CoA | 0.051 ± 0.004 | This work |
| — | 3-hydroxyacyl-CoA dehydrogenase | E. coli FadB | 3-hydroxybutyryl-CoA | 0.185 ± 0.001 | This work |
| — | 3-ketoacyl-CoA thiolase | E. coli AtoB | acetoacetyl-CoA | 17.1 ± 1.2 | This work |
| | | E. coli FadA | acetoacetyl-CoA | 0.013 ± 0.002 | This work |
| | | R. eutropha BktB | acetoacetyl-CoA | 27.0 ± 1.1 | This work |
| | | S. collinus FadA | acetoacetyl-CoA | 115.6 ± 1.0 | This work |
| | | P. putida FadAx | acetoacetyl-CoA | 30.9 ± 0.3 | This work |

Additional details on alkylsuccinate synthase enzymes, required for the activation of hydrocarbons via fumarate addition are provided in TABLE C:

TABLE C

Observed alkane activation via fumarate addition (alkylsuccinate synthases)

| Hydrocarbon Substrate | Organism(s) | Product | Literature Evidence | Reference |
|---|---|---|---|---|
| Methane | bacterial consortium (Alaskan North Slope) | methylsuccinate | Product detected (2.08 µM) in oil field sample | Duncan at al. (2009) |
| | bacterial consortium | methylsuccinate | Product detected in production field sample from oil reservoir | Bian at al (2015) |
| Ethane | bacterial consortium (Alaskan North Slope) | ethylsuccinate | Product detected (1.77 µM) in oil field sample | Duncan et al. (2009) |
| | bacterial consortium | ethylsuccinate | Product detected in production field sample from oil reservoir | Bian et al (2015) |
| Propane | bacterial consortium (Alaskan North Slope) | methylethylsuccinate | Product detected (2.18 µM) in oil field sample | Duncan et al. (2009) |
| | Desulfosarcina sp. BuS5 | methylethylsuccinate/n-propylsuccinate | Terminal and sub-terminal product formation from bacterial cultures | Kniemeyer et al. (2007) |
| | bacterial consortium | methylethylsuccinate | Product detected in production field sample from oil reservoir | Bian et al (2015) |

TABLE C-continued

Observed alkane activation via fumarate addition (alkylsuccinate synthases)

| Hydro-carbon Substrate | Organism(s) | Product | Literature Evidence | Reference |
|---|---|---|---|---|
| Butane | bacterial consortiums (Alaskan North Slope) | methylpropylsuccinate | Product detected (0.76 µM) in field sample | Duncan et al. oil (2009) |
| | Desultosarcina sp. BuS5 | methylpropylsuccinate | Terminal and sub-terminal product formation from bacterial cultures | Kniemeyer et al. (2007) |
| | bacterial consortium | methylpropylsuccinate | Product detected in production field sample from oil reservoir | Bian et al (2015) |
| Pentane | Azoarcus sp. H × N1 | Methylbutylsuccinate | Product formation from crude enzyme assay (~5% relative to hexane) | Webner (2012) |
| | bacterial consortium | methylbutylsuccinate | Product detected in production field sample from oil reservoir | Bian et al (2015) |
| Hexane | Azoarcus sp. H × N1 | methylpentylsuccinate | Product formation from crude enzyme assay (55 µM in crude extract assays) | Webner (2012) |
| | bacterial consortium | methylpentylsuccinate | Product detected in production field sample from oil reservoir | Bian et al (2015) |
| Heptane | Azoarcus sp. H × N1 | methylhexylsuccinate | Product formation from crude enzyme assay (~120% relative to hexane) | Webner (2012) |
| | bacterial consortium | methylhexylsuccinate | Product detected in production field sample from oil reservoir | Bian et al (2015) |
| Octane | Azoarcus sp. H × N1 | methylheptylsuccinate | Product formation from crude enzyme assay (~50% relative to hexane) | Webner (2012) |
| | bacterial consortium | methylheptylsuccinate | Product detected in production field sample from oil reservoir | Bian at al (2015) |

Figure 7:
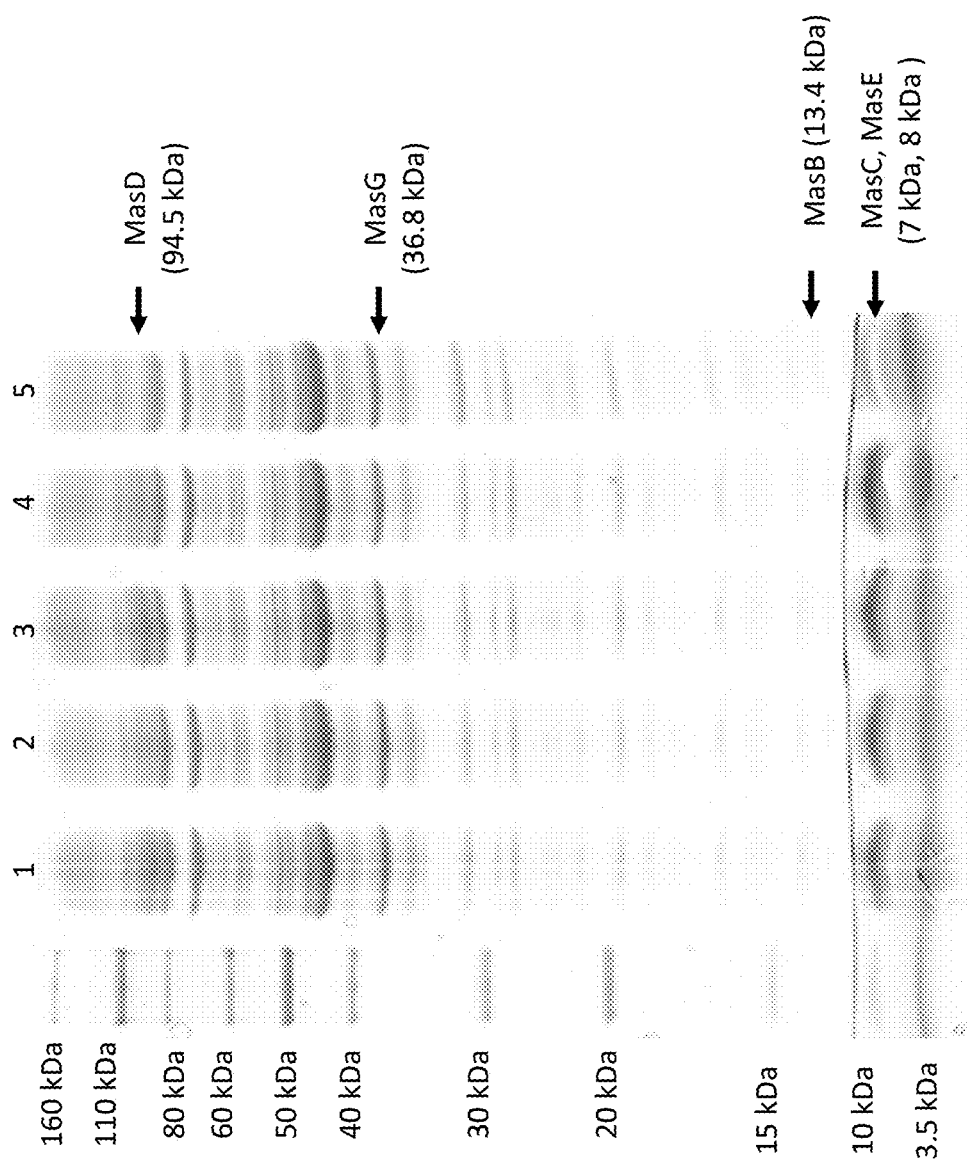
FIG. 7. Expression of components of the alkyl-succinate synthase from *Azoarcus* sp. HxN1, part of the oxygen-independent alkane activation/utilization pathway. Soluble cell extract of *E. coli* cells expressing MasB (A9J4K0), MasC (A9J4K2), MasD (A9J4K4), MasE (A9J4K6), and MasG (A9J4J6). Lane 1: pETDuet-1-P1-MasCDEB-P2-MasG; Lane 2: pETDuet-1-P1-MasCDE-P2-MasG; Lane 3: pETDuet-1-P1-MasCDEB; Lane 4: pETDuet-1-P1-MasCDE; Lane 5: pETDuet-1.
Figure 8A:
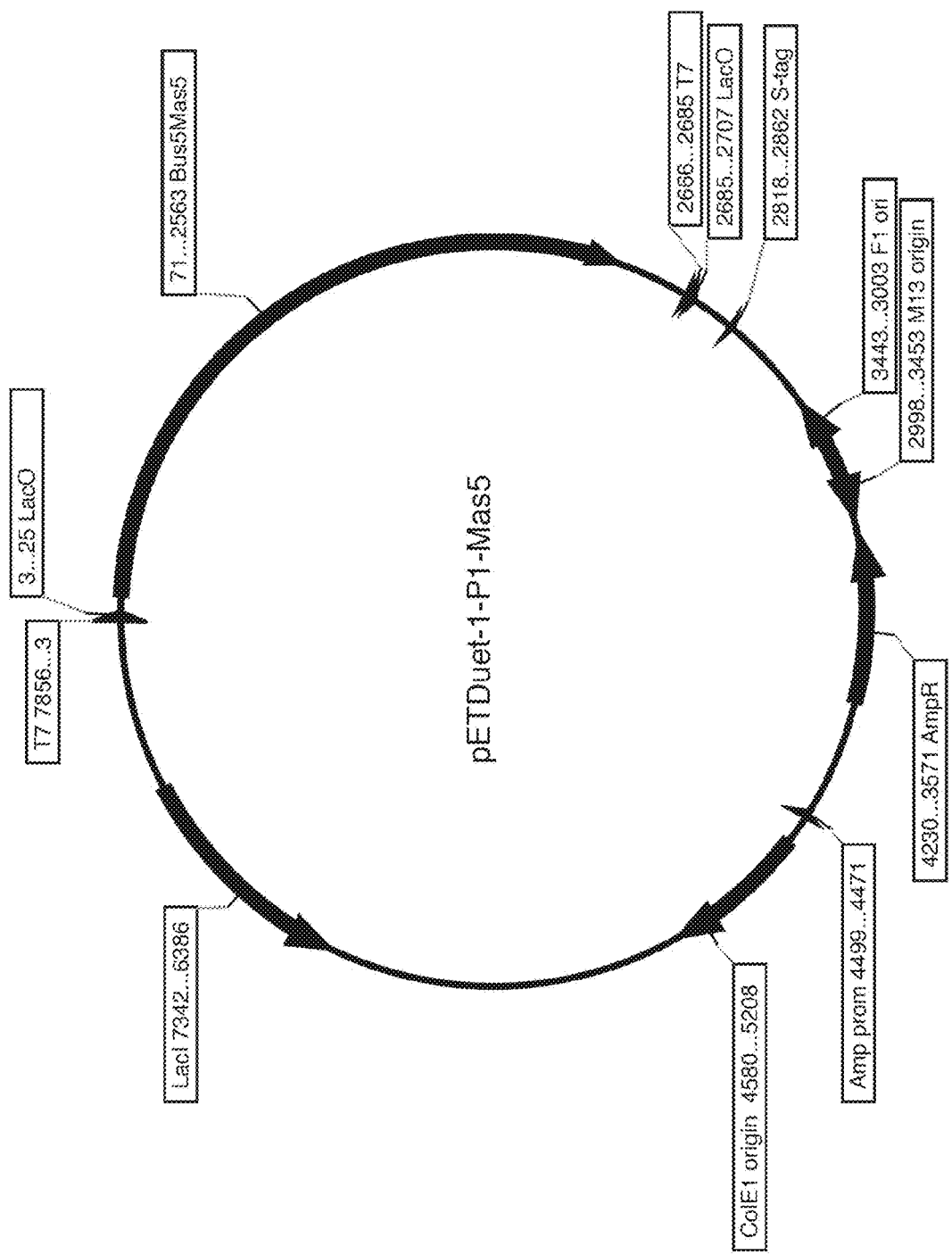
FIG. 8A-C. Vectors expressing the components of the oxygen-independent activation enzyme alkyl-succinate synthase from *Desulfosarcina* sp. BuS5. Proteins identified through similarity to *Azoarcus* sp. HxN1 MasBCDEG as well as physical location in *Desulfosarcina* sp. BuS5 genome. Mas5: WP_027352796.1; Mas8: WP_051374532.1; Mas11: WP_027352800.1.
Figure 8B:
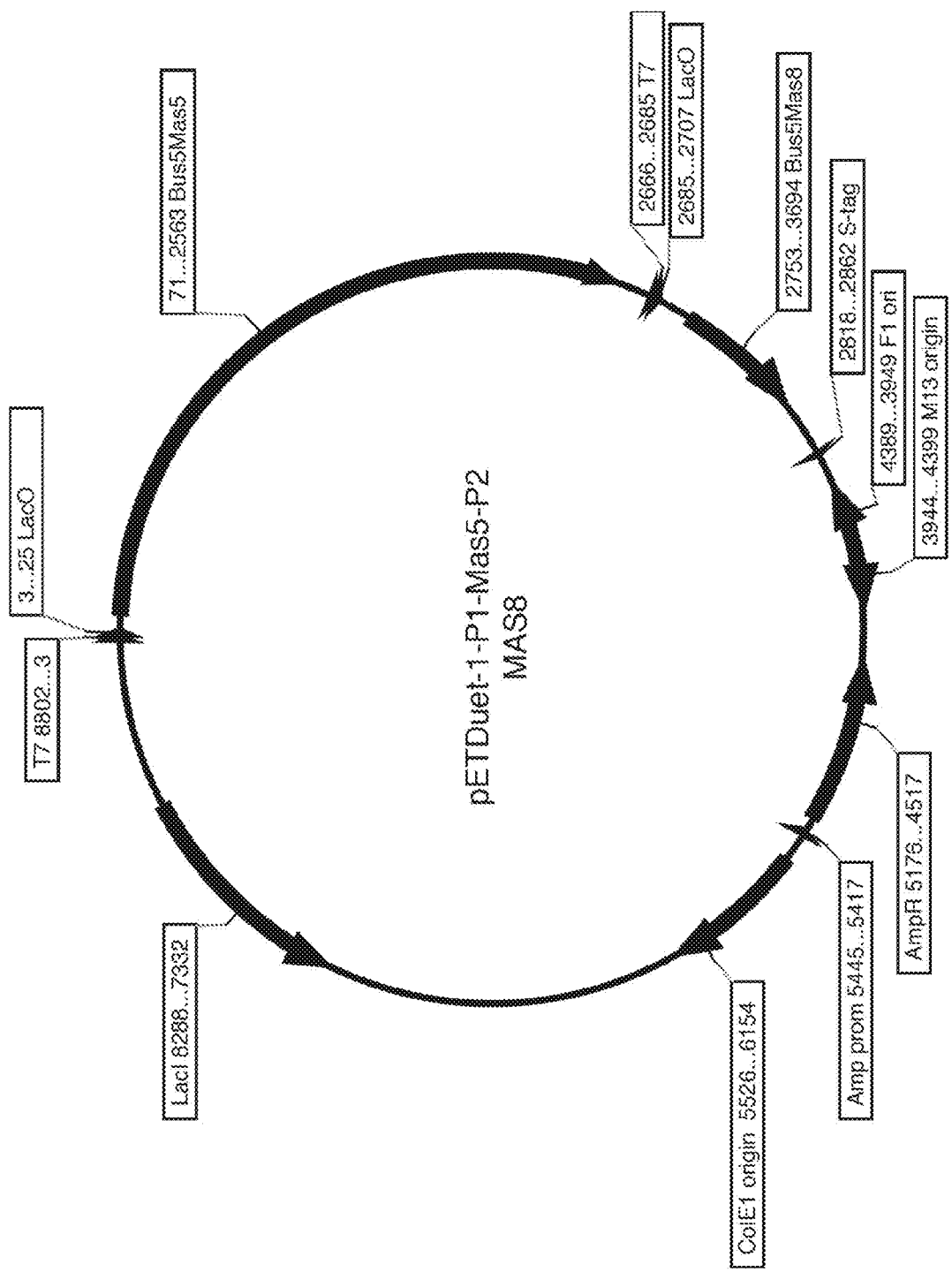
Figure 8C:
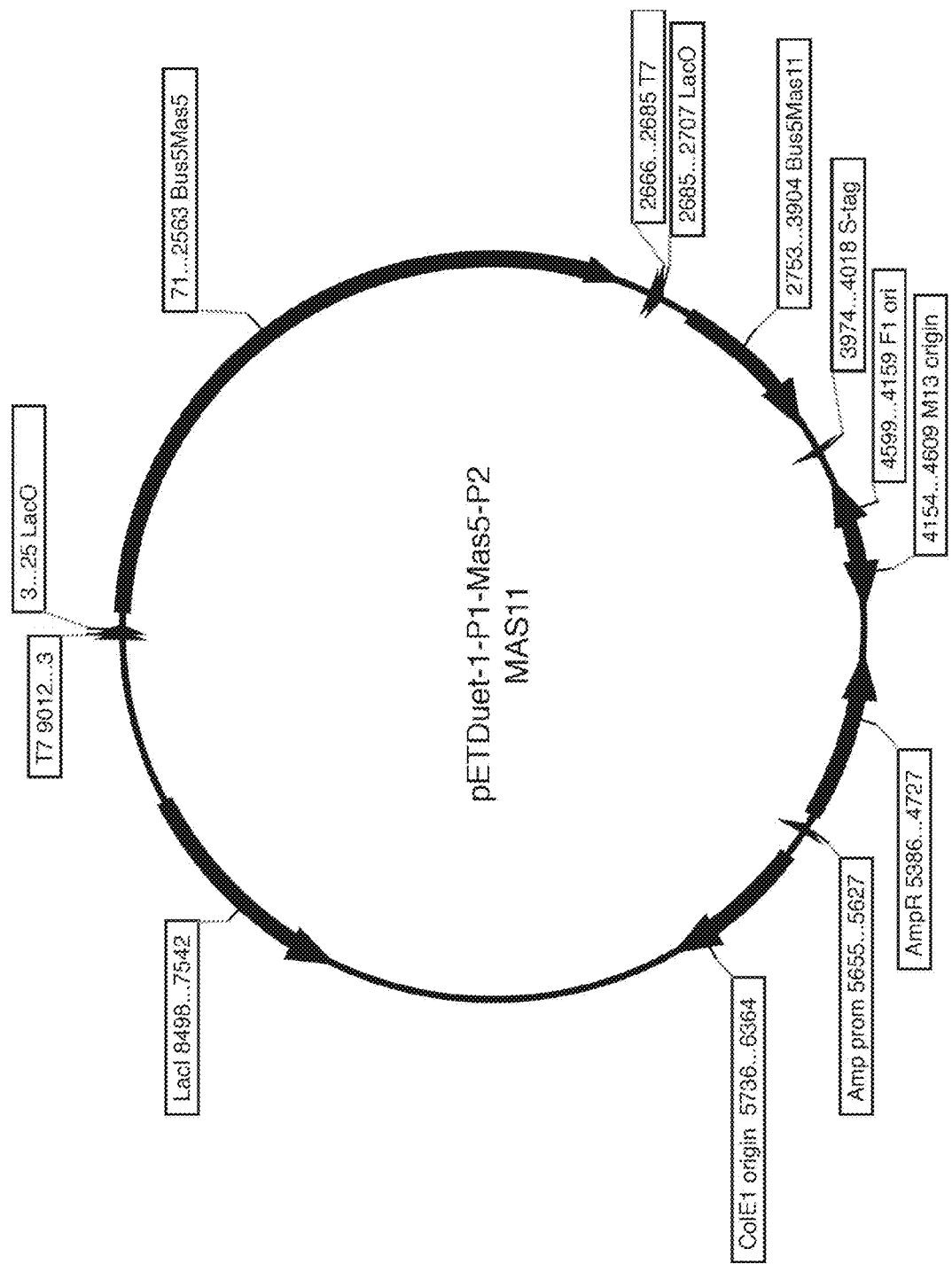
Figure 9A:
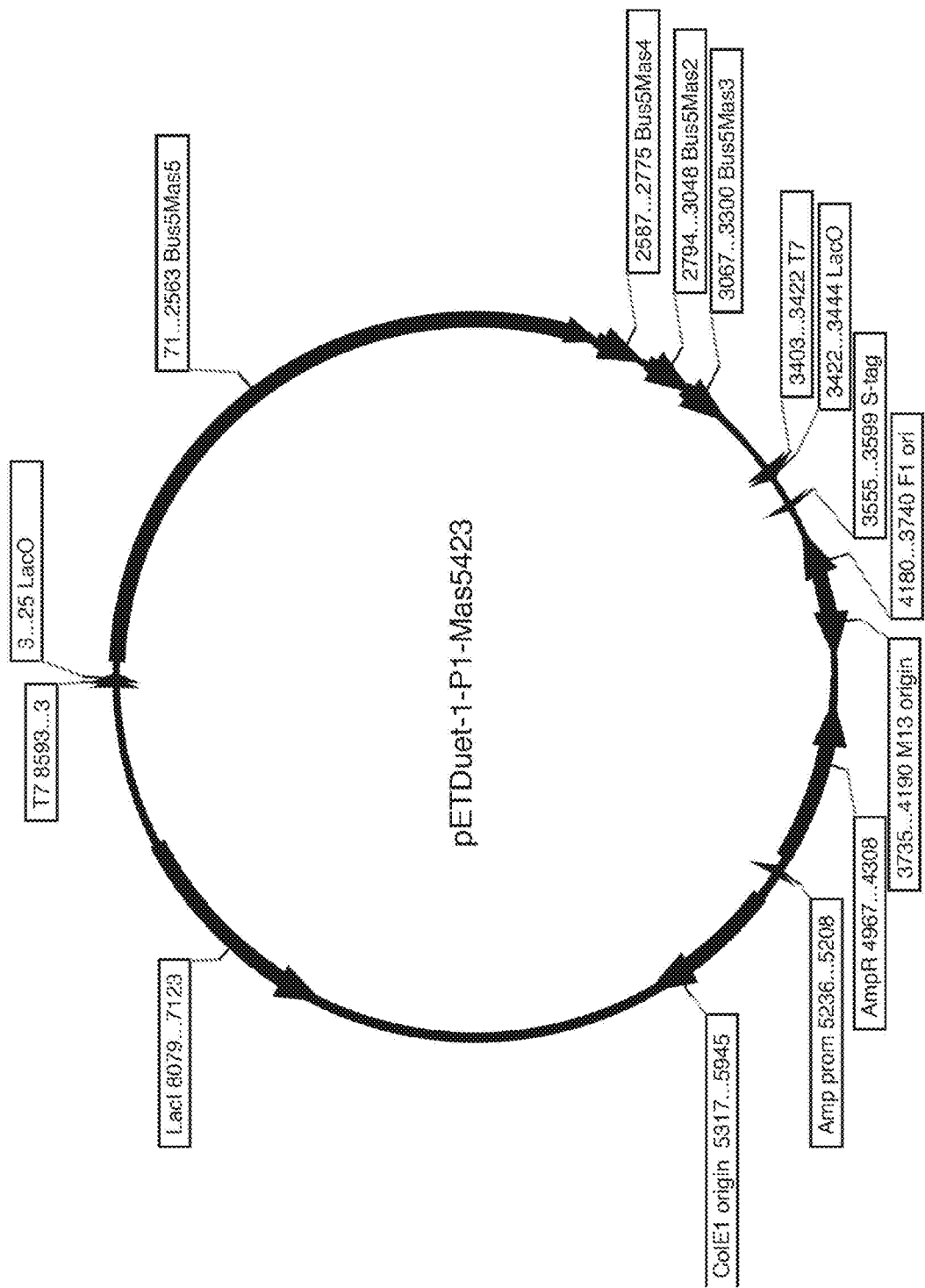
FIG. 9A-C. Vectors expressing the components of the oxygen-independent activation enzyme alkyl-succinate synthase from *Desulfosarcina* sp. BuS5. Proteins identified through similarity to *Azoarcus* sp. HxN1 MasBCDEG as well as physical location in *Desulfosarcina* sp. BuS5 genome. Mas5: WP_027352796.1; Mas4: WP_027352795.1; Mas3: WP_027352794.1; Mast: WP_027352793.1; Mas8: WP_051374532.1; Mas11: WP 027352800.1.
Figure 9B:
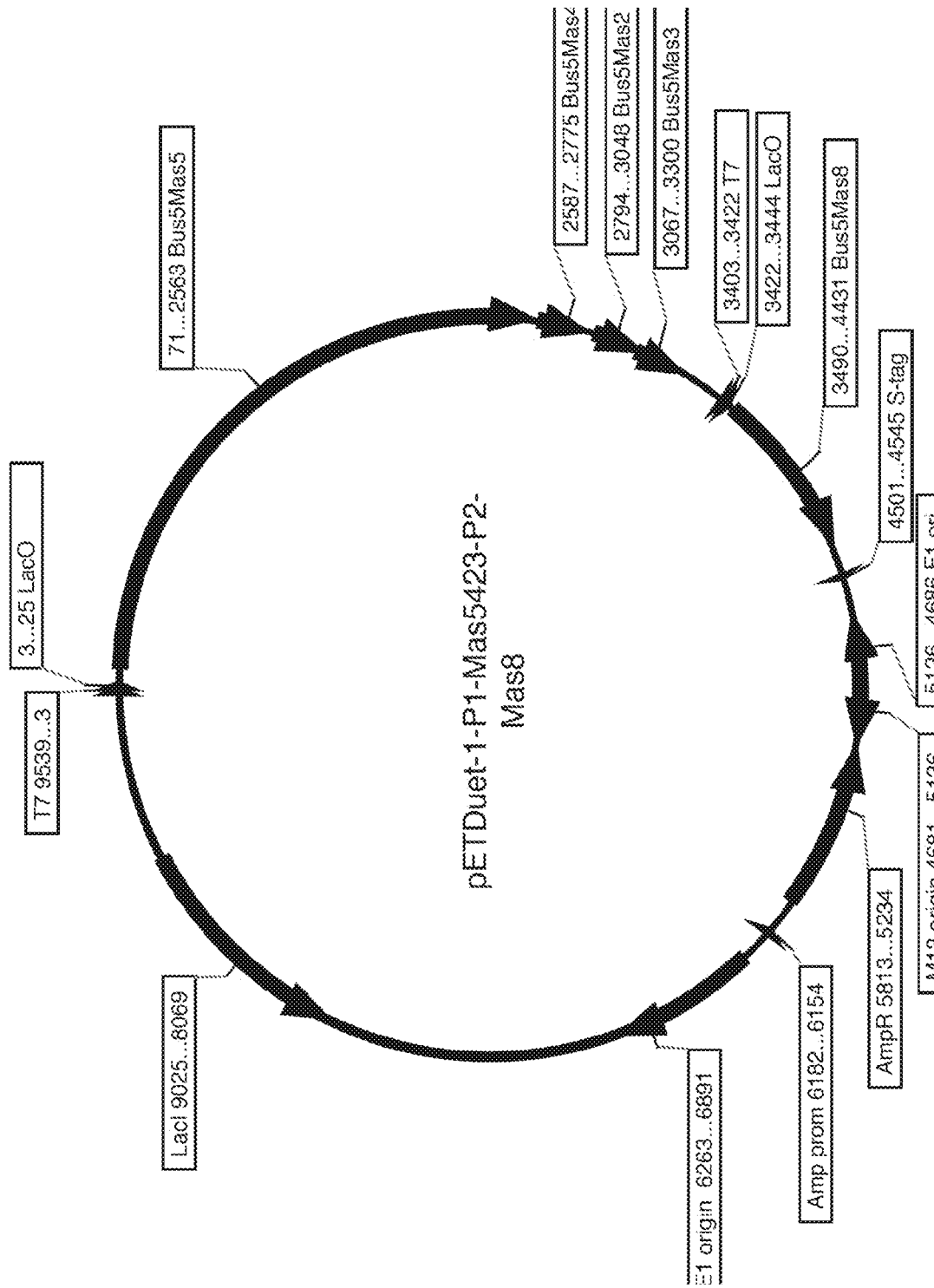
Figure 9C:
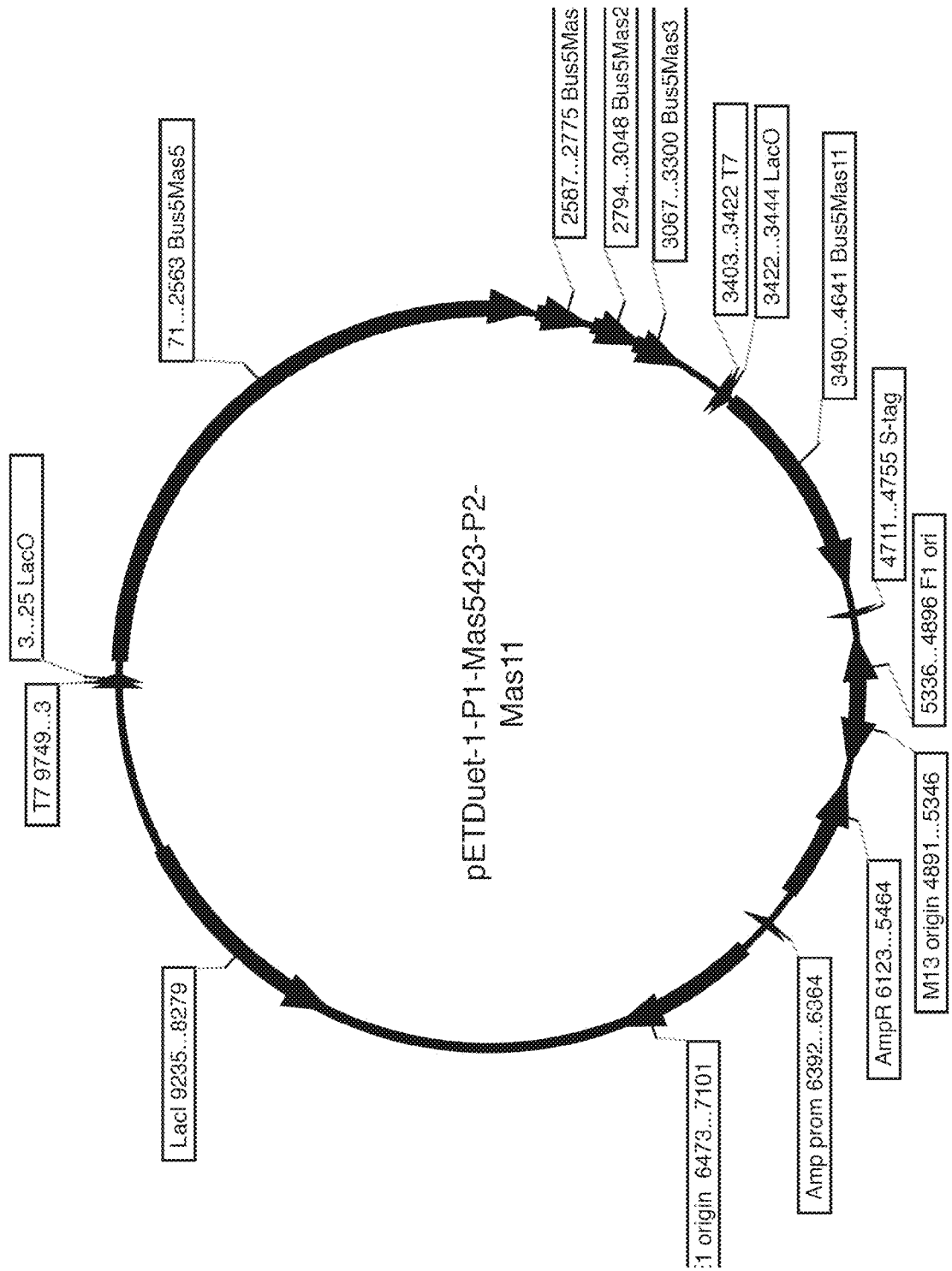
Figure 10A:
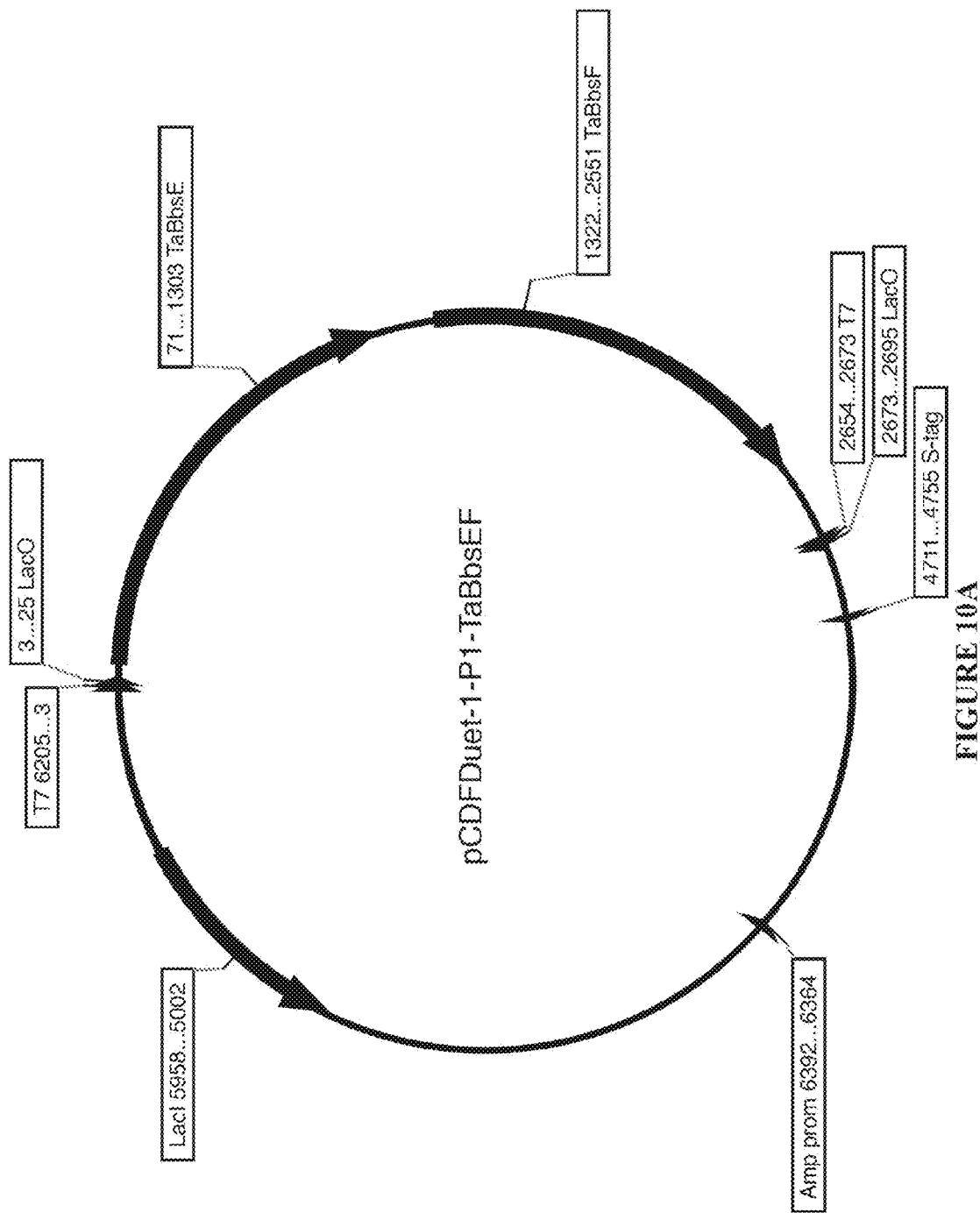
FIG. 10A-C. Vectors expressing enzymes for the conversion of fumarate activated hydrocarbon intermediates to product precursors. TaBbsEF: *T. aromatica* succinyl-CoA.
Figure 10B:
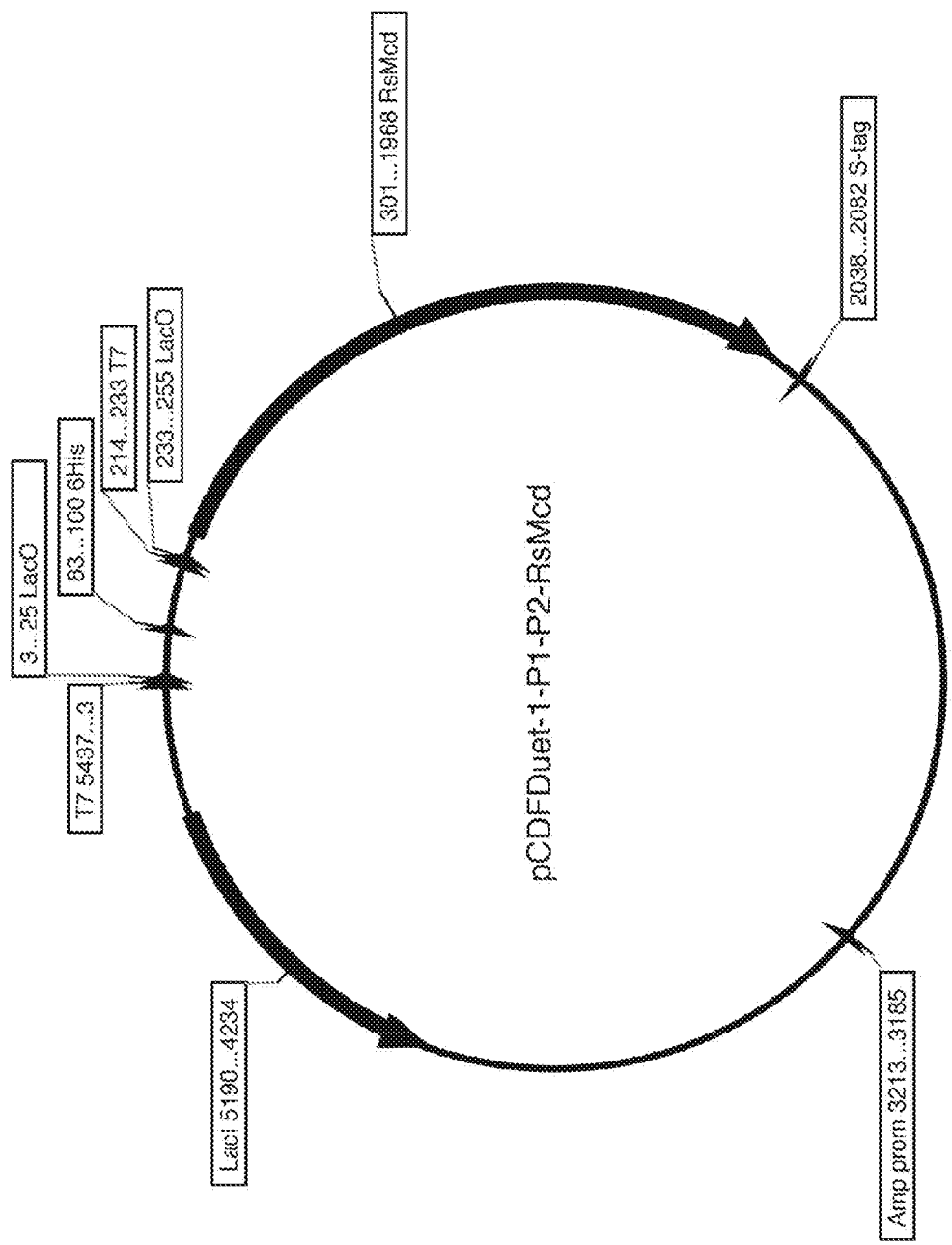
Figure 10C:
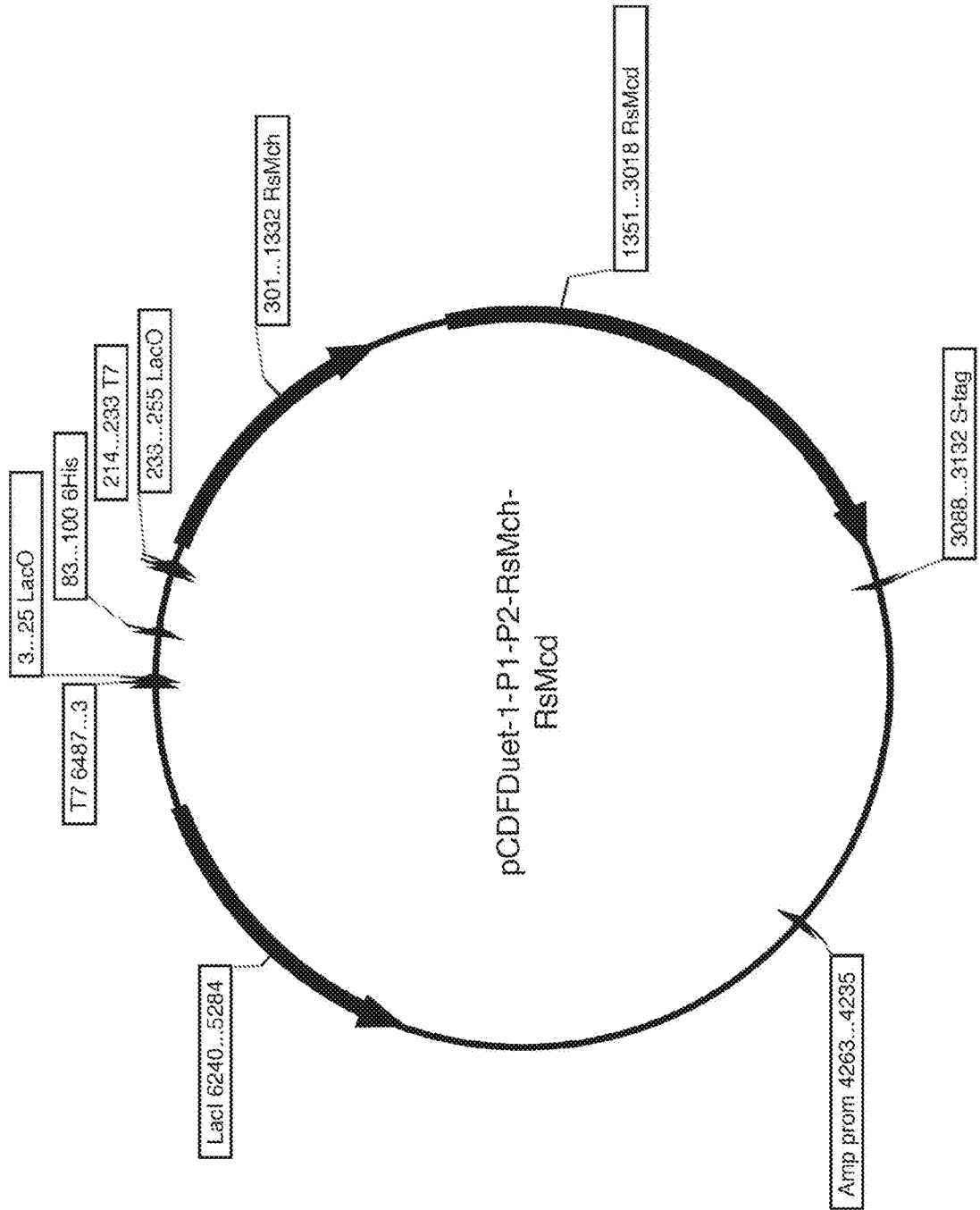

Included in these alkylsuccinate synthase enzymes are those from *Azoarcus* sp. HxN1 (Grundmann et al., 2008) and *Desulfosarcina* sp. BuS5 (Kniemeyer et al., 2007) for which the catalytic subunit, and associated subunits for the case of *Azoarcus* sp. HxN1, have been proposed. Genes encoding the proposed subunits of the *Azoarcus* sp. HxN1 alkylsuccinate synthase have been cloned into required expression vectors as shown in FIG. 6. Evaluation of the expression of alkylsuccinate synthase subunits in *E. coli* is shown in FIG. 7.

Furthermore, several candidate alkylsuccinate synthase subunits and associated proteins have been identified through a BLAST search of *Azoarcus* sp. HxN1 alkylsuccinate synthase subunits against the recently sequenced *Desulfosarcina* sp. BuS5 genome, a strain that degrades propane and butane via fumarate addition. This search identified several enzymes within close physical proximity to the large catalytic MasD subunit (WP_027352796.1), including 2 enzymes with high similarity to the *Azoarcus* sp. HxN1 MasE subunit (WP_027352794.1 and WP_027352793.1), a protein with similarity to alkylsuccinate synthase gamma subunits from *Desulfatibacillum alkenivorans* AK-01 and *Smithella* sp. SCADC (WP_027352795.1), and enzymes with similarity to the *Azoarcus* sp. HxN1 MasG activating enzyme (WP_051374532.1) and other radical SAM enzymes (WP_027352800.1). In all, 13 proteins appear to be encoded from an operon within the *Desulfosarcina* sp. BuS5 genome spanning the locus from 66239-79342 in the associated genome sequence NZ_AXAM01000003.1. Genes encoding potential subunits of the alkylsuccinate synthase (WP_027352793.1, WP_027352794.1, WP_027352795.1, and WP_027352796.1) and activation enzyme (WP_051374532.1 and WP_027352800.1) have been cloned into required expression vectors as shown in FIG. 8 and FIG. 9.

This type of homology search can be further exploited to identify other potential alkylsuccinate synthase enzymes/operons through a BLAST search of these enzymes against other hydrocarbon degrading species. For example, a search of the *Desulfosarcina* sp. BuS5 MasD subunit (WP_027352796.1) was used to identify potential MasD subunits from species such as *Peptococcaceae* bacterium SCADC1_2_3 (WP_036734374.1), *Desulfoglaeba alkanexedens* ALDC (ADJ51097.1), and *Peptococcaceae* bacterium BRH_c4a (KJS01634.1), among others.

Furthermore, additional enzymes required for conversion of fumarate activated hydrocarbon intermediates to product precursors have been investigated. Enzymes such as *T. aromatica* succinyl-CoA:(R)-benzylsuccinate CoA-transferase (Q9KJF0, Q9KJE9), *R. sphaeroides* (2S)-methylsuccinyl-CoA dehydrogenase (ADC44452.1), and *R. sphaeroides* mesaconyl-coenzyme A hydratase (Q3IZ78) enable the conversion of the fumarate activated hydrocarbons to product precursors, which can then be converted to desired products. Genes encoding the above proteins have been cloned into required expression vectors (FIG. 10A-C) and their expression in *E. coli* evaluated (FIG. 11).

The above described enzymes for hydrocarbon activation/utilization and conversion to acyl-CoA intermediates through the fumarate addition pathway provide a route for the bioconversion of short-chain hydrocarbons of varying chain length. For the specific case of methane activation/utilization, the pathways depicted in FIG. 3 and FIG. 4 can also be exploited for the conversion of fumarate activated methane into product precursors as well as for the regeneration of fumarate. TABLE D and TABLE E describe the characterization of enzymes involved in these versions of the bioconversion pathway:

TABLE D

Characterization of enzymes involved in the pathway for bioconversion of hydrocarbons via fumarate addition as depicted in FIG. 3

| Enzyme name | Enzyme | Substrate | Measured specific activity ($\mu$mol/mg protein/min) | Reference |
|---|---|---|---|---|
| alkylsuccinate synthase | | | See Table B for details | |
| succinyl-CoA: 2-methyl-alkyl-succinyl-CoA transferase/2-methyl-alkyl-succinyl-CoA synthetase | T. aromatica BSCT | Methylsuccinate and succinyl-CoA | Methylsuccinyl-CoA formation observed | Leutwein and Heider (2001) |
| 2-methyl-alkyl-succinyl-CoA dehydrogenase | R. sphaeroides Mcd | (2S)-methylsuccinyl-CoA | mesaconyl-CoA formation observed | Erb et al (2009) |
| mesaconyl-C1-CoA-C4 transferase | C. aurantiacus Mct | mesaconyl-C1-CoA | mesaconyl-C4-CoA formation observed | Zarzycki et al (2009) |
| mesaconyl-C4-CoA hydratase | C. aurantiacus Meh | mesaconyl-C4-CoA | (S)-citramalyl-CoA formation observed | Zarzycki et al (2009) |
| L-malyl-CoA/citramalyl-CoA lyase | C. aurantiacus Mmc | (S)-citramalyl-CoA | Acetyl-CoA and pyruvate formation observed | Zarzycki et al (2009) |
| pyruvic-malic carboxylase | E. coli MaeA | pryuvate | 1.3, $K_m$: 16 mM | Stols and Donnelly (1997) |
| fumarase | E. coli FumA | L-malate | 706, $K_m$: 700 mM | van Vugt-Lussenburg et al (2013) |

TABLE E

Characterization of enzymes involved in the pathway for bioconversion of hydrocarbons via fumarate addition as depicted in FIG. 4

| Enzyme Number | Enzyme class | Enzyme | Substrate | Measured specific activity ($\mu$mol/mg protein/min) | Reference |
|---|---|---|---|---|---|
| 1 | alkylsuccinate synthase | | | See Table C for details | |
| 2 | succinyl-CoA:2-methyl-alkyl-succinyl-CoA transferase/2-methyl-alkyl-succinyl-CoA synthetase | T. aromatica BSCT | Methylsuccinate and succinyl-CoA | Methylsuccinyl-CoA formation observed | Leutwein and Heider (2001) |
| 3 | 2-methyl-alkyl-succinyl-CoA dehydrogenase | R. sphaeroides Mcd | (2S)-methylsuccinyl-CoA | mesaconyl-CoA formation observed | Erb et al (2009) |
| 4 | mesaconyl CoA hydratase/β methylmalyl-CoA dehydratase | R. sphaeroides Mch | β methylmalyl CoA (reverse reaction) | 1400, mesaconyl CoA formation observed | Zarzycki et al (2008) |
| 5 | β-methylmalyl-CoA lyase | R. sphaeroides Mcl1 | β-methylmalyl-CoA | 26, $K_m$: 10 $\mu$M | Erb et al (2010) |
| 6 | propionyl-CoA carboxylase | M. sedula Pcc | propionyl-CoA | 3.3, $K_m$: 70 $\mu$M (75° C.) | Hugler et al (2003) |
| | | S. coelicolor Pcc | propionyl-CoA | 0.2, $K_m$: 76 $\mu$M | Arabolaza et al (2010) |
| 7 | methylmalonyl-CoA epimerase | P. horikoshii Mce | (S)-2-methylmalonyl-CoA | 162, $K_m$: 79 $\mu$M | Bobik and Rasche (2004) |
| | methylmalonyl-CoA mutase | P. freudenreichii subsp. shermanii Mcm | (R)-2-methylmalonyl-CoA | 26, $K_m$: 124 $\mu$M | Chowdhury et al (1999); Padovani et al (2006) |
| 8 | succinyl-CoA:2-methyl-alkyl-succinyl-CoA transferase/succinyl-CoA synthetase | E. coli SucCD | Succinate (reversible reaction) | 18.6, $K_m$: 141 $\mu$M | Nolte et al (2014) |
| 9 | succinate dehydrogenase | E. coli SdhCDAB | succinate | $K_m$: 2.5 $\mu$M | Maklashina et al (2001) |
| 10 | glyoxylate carboligase | E. coli Gcl | glyoxylate | 17.5, $K_m$: 900 $\mu$M | Kaplun et al (2008) |
| 11 | tartronate semialdehyde reductase | E. coli GarR | tartronate semialdehyde | $K_m$: 280 $\mu$M | Njau et al (2000) |
| 12 | glycerate kinase | E. coli GlxK | D-glycerate | $K_m$: 70 $\mu$M | Ornston and Ornston (1969) |

Together, these enzymatic components described above provide a full route for the conversion of short chain hydrocarbons to acyl-CoA (e.g. acetyl-CoA) product precursors, which can subsequently be converted into fuels and chemicals (e.g. carboxylic acids, alcohols, hydrocarbons, and their alpha-, beta-, and omega-functionalized derivatives) through numerous product synthesis pathways, such as beta-oxidation reversal (BOX-R) or fatty acid biosynthesis. BOX-R is not described in great detail herein, since it has been described in the inventor's prior patents and publications.

The use of an oxygen-dependent activation mechanism in which an alkane hydroxylase adds a terminal alcohol group to the hydrocarbon can also be exploited for the bioconversion of short chain hydrocarbons to fuels and chemicals as depicted in FIG. 5. Characterization of required enzymes for hydrocarbon activation and conversion to product precursors is shown in TABLE F:

In addition to the demonstrated activation of hydrocarbon such as pentane and hexane to the associated alcohols, the enzymes required for the conversion of these alcohols to product precursors have also been characterized. The combination of these enzymatic components provide a full route for the conversion of short chain hydrocarbons to acyl-CoA (e.g. acetyl-CoA) product precursors, which can subsequently be converted into fuels and chemicals (e.g. carboxylic acids, alcohols, hydrocarbons, and their alpha-, beta-, and omega-functionalized derivatives) through numerous product synthesis pathways, such as beta-oxidation reversal or fatty acid biosynthesis.

The enzymes described in TABLE F represent a number of examples of enzymes with required pathway activity, however this list is not representative of all available enzymes. Many additional enzymes have been shown to possess the required activities in literature and as such, can easily be integrated with the pathway framework. Further-

TABLE F

Characterization of enzymes involved in the pathway for bioconversion of hydrocarbons via hydroxylation as depicted in FIG. 5

| Enzyme Number | Enzyme class | Enzyme | Substrate | Measured specific activity (μmol/mg protein/min) | Reference |
|---|---|---|---|---|---|
| 1 | alkane monooxygenase or alkane hydroxylase | *M. capsulatus* (Bath) sMMO | Methane | $K_{m,methane}$: 3 μM | Green and Dalton (1986) |
| | | *M. capsulatus* (Bath) pMMO | | 0.139 ± 0.005 | Sirajuddin et al. (2014) |
| | | *Thauera butanivorans* sBMO | | $K_{m,methane}$: 1100 μM | Cooley et al. (2009) |
| | | *Thauera butanivorans* sBMO | Ethane | $K_{m,methane}$: 2.2 μM | Cooley et al. (2009) |
| | | *P. putida* AlkBFG | Propane | Propanol formation observed | Koch et al. (2009) |
| | | *Mycobacterium* sp. strain HXN-1500 CYP153A6 | | Propanol formation observed | Koch et al. (2009) |
| | | *Thauera butanivorans* sBMO | | $K_{m,propane}$: 0.94 μM | Cooley et al. (2009) |
| | | *P. putida* AlkBFG | Butane | Butanol formation observed | Koch et al. (2009) |
| | | *Mycobacterium* sp. strain HXN-1500 CYP153A6 | | Butanol formation observed | Koch et al. (2009) |
| | | *Thauera butonivorans* sBMO | | $K_{m,butane}$: 0.24 μM | Cooley et al. (2009) |
| | | *P. putida* AlkBGT | Pentane | Pentanol formation observed, see FIG. 13 | This work |
| | | *P. putida* AlkBGT | Hexane | Hexanol formation observed, see FIG. 12 | This work |
| 2 | alcohol dehydrogenase | *E. coli* FucO | butyraldehyde | 5.08 ± 0.08 | This work |
| 3 | Coenzyme A-acylating aldehyde dehydrogenase | *L. Reuteri* PduP | propionaldehyde | 25 ± 0.2, $K_m$: 28 mM | Sabet-Azad et al. (2013) |
| 4 | acyl-CoA synthetase | *E. coli* Acs | acetate | $K_m$: 200 μM | Brown et al. (1977) |
| | | *P. Aeruginosa* butyryl-CoA synthetase | butyrate | 0.255, $K_m$: 10 μM | Shimizu et al. (1981) |
| 5 | acylating aldehyde dehydrogenase | *E. coli* AdhE | butyryl-CoA | 0.073 ± 0.00 | This work |
| | | *E. coli* MhpF | butyryl-CoA | 0.009 ± 0.003 | This work |
| | β-oxidation enzymes | | | | |
| — | Acyl-CoA dehydrogenase | *E. coli* FadE | butyryl-CoA | 0.008 ± 0.001 | This work |
| — | Enoyl-CoA hydratase | *E. coli* FadB | crotonyl-CoA | 0.051 ± 0.004 | This work |
| — | 3-hydroxyacyl-CoA dehydrogenase | *E. coli* FadB | 3-hydroxybutyryl-CoA | 0.185 ± 0.001 | This work |
| — | 3-ketoacyl-CoA thiolase | *E. coli* AtoB | acetoacetyl-CoA | 17.1 ± 1.2 | This work |
| | | *E. coli* FadA | acetoacetyl-CoA | 0.013 ± 0.002 | This work |
| | | *R. eutropha* BktB | acetoacetyl-CoA | 27.0 ± 1.1 | This work |
| | | *S. collinus* FadA | acetoacetyl-CoA | 115.6 ± 1.0 | This work |
| | | *P. putida* FadAx | acetoacetyl-CoA | 30.9 ± 0.3 | This work | more, sequence similarity can also be used for the identification of additional enzymes. As an example, components of putative alkane monooxygenase system in *Rhodobacter sphaeroides* were identified through a BLAST using the soluble methane monooxygenase (sMMO) system of *Methylococcus capsulatus* (Bath). Required hydroxylase alpha (YP_352924.1) and reductase (YP_352923.1) subunits were identified, which are part of a 4 gene operon also including a hydroxylase beta subunit (YP_352922.1) and a regulatory protein (YP_352921.1). Genes encoding potential subunits this putative alkane monooxygenase have been cloned into required expression vectors as shown in FIG. 14A-B.

By exploiting either of these hydrocarbon activation described above, various fuels and chemicals (e.g. carboxylic acids, alcohols, hydrocarbons, and their alpha-, beta-, and omega-functionalized derivatives) can be synthesized from short-chain hydrocarbons through the metabolic pathways described and demonstrated herein.

Each of the following is incorporated by reference herein in its entirety for all purposes:

U.S. 61/440,192, filed Feb. 7, 2011, WO2013036812, US20130316413 Reverse beta oxidation pathway by Clomburg et al.

U.S. 61/531,911, filed Sep. 7, 2011, WO2013036812 US20140273110 Functionalized carboxylic acids and alcohols by reverse fatty acid oxidation by Gonzalez & Clomburg 61/932,057, filed Jan. 27, 2014, WO2015112988, Type II fatty acid synthesis enzymes in reverse beta-oxidation by Gonzalez & Clomburg All accession numbers (generally in brackets after a gene or protein) are expressly incorporated by reference for all purposes herein. Inclusion of the information at each accession entry, would render the patent of inordinate length, and thus, incorporation of all sequences (and other information found therein) by reference is preferred. A person of ordinary skill in the art will recognize the accession numbers and be able to access them from a variety of databases.

Arabolaza A, et al., (2010) Crystal structures and mutational analyses of acyl-CoA carboxylase beta subunit of *Streptomyces coelicolor*. *Biochemistry* 49, 7367-7376

Bian X Y, et al., (2015) Insights into the anaerobic biodegradation pathway of n-alkanes in oil reservoirs by detection of signature metabolites. *Sci Rep* 5

Bobik T A & Rasche M E (2004) Purification and partial characterization of the *Pyrococcus horikoshii* methylmalonyl-CoA epimerase. *Appl Microbiol Biotechnol* 63, 682-685

Brown T D, et al., (1977). The enzymic interconversion of acetate and acetyl-coenzyme A in *Escherichia coli*. *J Gen Microbiol* 102(2), 327-36

Callaghan A V (2013) Enzymes involved in the anaerobic oxidation of n-alkanes: from methane to long-chain paraffins. *Front Microbiol* 4(89), 10-3389

Chowdhury S & Banerjee R (1999) Role of the dimethylbenzimidazole tail in the reaction catalyzed by coenzyme B12-dependent methylmalonyl-CoA mutase *Biochemistry* 38, 15287-15294

Cooley R B, et al., (2009) Kinetic characterization of the soluble butane monooxygenase from *Thauera butanivorans*, formerly '*Pseudomonas butanovora*'. *Microbiology* 155, 2086-96

Datsenko I C A & Wanner B L (2000) One-step inactivation of chromosomal genes in *Escherichia coli* K-12 using PCR products. *PNAS* 97(12), 6640-5

Dellomonaco C, et al., (2011) Engineered reversal of the beta-oxidation cycle for the synthesis of fuels and chemicals. *Nature* 476, 355-359

Duncan K E, et al., (2009) Biocorrosive thermophilic microbial communities in Alaskan North Slope oil facilities. *Environ Sci Technol* 43, 7977-84

Erb T J, et al., (2010) The apparent malate synthase activity of *Rhodobacter sphaeroides* is due to two paralogous enzymes, (3S)-malyl-coenzyme A (CoA)/β-methylmalyl-CoA lyase and (3 S)-malyl-CoA thioesterase. *J Bacteriol* 192, 1249-58

Erb T J, et al., (2009) (2S)-Methylsuccinyl-CoA dehydrogenase closes the ethylmalonyl-CoA pathway for acetyl-CoA assimilation. *Mol Microbiol* 73, 992-1008

Erb T J, et al., (2008) Ethylmalonyl-CoA mutase from *Rhodobacter sphaeroides* defines a new subclade of coenzyme B12-dependent acyl-CoA mutases. *J Biol. Chem* 283, 32283-32293

Green J & Dalton H. (1986) Steady-state kinetic analysis of soluble methane mono-oxygenase from *Methylococcus capsulatus* (Bath). *Biochem J* 236, 155-62

Grundmann O, et al., (2008) Genes encoding the candidate enzyme for anaerobic activation of n-alkanes in the denitrifying bacterium, strain HxN1. *Environ Microbiol* 10(2), 376-85

Hugler M, et al., (2003) Characterization of acetyl-CoA/propionyl-CoA carboxylase in *Metallosphaera sedula*. Carboxylating enzyme in the 3-hydroxypropionate cycle for autotrophic carbon fixation. *Eur J Biochem* 270, 736-744

Kaplun A, et al., (2008) Glyoxylate carboligase lacks the canonical active site glutamate of thiamine-dependent enzymes. *Nat Chem Biol* 4, 113-118

Kim S, et al., (2015) Synthesis of medium-chain length (C6-C10) fuels and chemicals via β-oxidation reversal in *Escherichia coli*. *J Ind Microbiol Biotechnol* 42(3), 465-75

Kniemeyer O, et al., (2007) Anaerobic oxidation of short-chain hydrocarbons by marine sulphate-reducing bacteria. *Nature* 449, 898-901

Koch D J, et al., (2009) In vivo evolution of butane oxidation by terminal alkane hydroxylases AlkB and CYP153A6. *Appl Environ Microbiol* 75, 337-44

Leutwein C & Heider J (2001) Succinyl-CoA:(R)-benzylsuccinate CoA-transferase: an enzyme of the anaerobic toluene catabolic pathway in denitrifying bacteria. *J Bacteriol* 183, 4288-4295

Lian J & Zhao Z, (2014) Reversal of the β-Oxidation Cycle in *Saccharomyces cerevisiae* for Production of Fuels and Chemicals, ACS Synth. Biol. 4 (3): 332-341

Linster C L, et al., (2011) Ethylmalonyl-CoA decarboxylase, a new enzyme involved in metabolite proofreading *J Biol Chem* 286, 42992-43003

Maklashina E, et al., (2001) Retention of heme in axial ligand mutants of succinate-ubiquinone oxidoreductase (complex II) from *Escherichia coli* *J Biol. Chem* 276, 18968-18976

Mbadinga S M, et al., (2011) Microbial communities involved in anaerobic degradation of alkanes. *Int Biodeterior Biodegrad* 65(1), 1-13

Neidhardt F C, et al., (1974) Culture Medium for *Enterobacteria*. *J Bacteriol* 119(3), 736-747

Njau R K, et al., (2000) Novel beta-hydroxyacid dehydrogenases in *Escherichia coli* and *Haemophilus influenza*. *J Biol Chem* 275, 38780-6.

Nolte J C, et al., (2014) Novel characteristics of succinate coenzyme A (succinate-CoA) ligases: conversion of malate to malyl-CoA and CoA-thioester formation of succinate analogues in vitro. *Appl Environ Microbiol* 80, 166-176

Ornston M K & Ornston L N (1969) Two forms of D-glycerate kinase in *Escherichia coli*. *J Bacteriol* 97, 1227-33

Padovani D & Banerjee R (2006) Alternative pathways for radical dissipation in an active site mutant of B12-dependent methylmalonyl-CoA mutase *Biochemistry* 45, 2951-2959

Sabet-Azad R, et al., (2013). Coenzyme A-acylating propionaldehyde dehydrogenase (PduP) from *Lactobacillus reuteri*: kinetic characterization and molecular modeling. *Enzyme Microb Technol* 53(4), 235-242

Shimizu S, et al., (1981). Butyryl-CoA synthetase of *Pseudomonas aeruginosa*. Purification and characterization. *Biochem Biophys Res Commun* 103, 1231-1237

Sirajuddin S, et al., (2014) Effects of zinc on particulate methane monooxygenase activity and structure. *J Biol Chem* 289, 21782-94.

Stols L & Donnelly M I (1997) Production of succinic acid through overexpression of NAD (+)-dependent malic enzyme in an *Escherichia coli* mutant. Appl Environ Microbiol 63, 2695-701 van Vugt-Lussenburg B M, et al., (2013) Biochemical similarities and differences between the catalytic [4Fe-4S] cluster containing fumarases FumA and FumB from *Escherichia coli*. *PloS One* 8, e55549

Webner K (2012) Die Gene der (1-Methylalkyl)succinat-Synthase im anaeroben n-Alkanabbau des Betaproteobakteriums Stamm HxN1: Universität Bremen Zarzycki J, et al., (2009) Identifying the missing steps of the autotrophic 3-hydroxypropionate $CO_2$ fixation cycle in *Chloroflexus aurantiacus*. *PNAS* 106, 21317-22.

Zarzycki J, et al., (2008) Mesaconyl-coenzyme A hydratase, a new enzyme of two central carbon metabolic pathways in bacteria. *J Bacteriol* 190, 1366-1374

We claim:

1. A method of producing a product comprising growing a genetically engineered bacteria in a culture broth containing a C1-C5 alkane and a terminal electron acceptor, wherein said genetically engineered bacteria converts the alkane to the product by oxygen-independent activation of the alkane, generating precursor intermediate acetyl-CoA, and producing a product from the acetyl-CoA, and wherein the genetically engineered bacteria selected from the group consisting of *E. coli, Bacillus, Streptomyces, Azotobacter, Trichoderma, Rhizobium, Pseudomonas, Micrococcus, Nitrobacter, Proteus, Lactobacillus, Pediococcus, Lactococcus, Salmonella, Streptococcus, Paracoccus, Methanosarcina*, and *Methylococcus* comprises a vector expressing enzymes or overexpressing enzymes catalyzing:

a) a sequence of reactions for the oxygen-independent activation of the alkane via fumarate addition to a 2-methyl-alkyl-succinate and subsequent conversion of said 2-methyl-alkyl-succinate to an acyl-CoA;

b) a sequence of reactions for the generation of the product precursor acetyl-CoA and an acyl-CoA or keto-acid from said acyl-CoA;

c) a sequence of reactions for the regeneration of the fumarate through the conversion of said acyl-CoA or keto-acid to the fumarate; and d) a sequence of reactions for the formation of the product from said product precursor acetyl-CoA;

wherein the alkane is the sole carbon source in the broth that can be activated;

wherein the enzymes comprise an alkyl succinate synthase that catalyzes the addition of the fumarate to the alkane to produce the 2-methyl-alkyl-succinate;

wherein one or more of the enzymes are overexpressed; and wherein the method further comprises isolating the product formed in step d).

2. The method of claim 1, wherein said enzymes catalyzing the sequence of reactions for the oxygen-independent activation and conversion to the acyl-CoA comprises:

a. the alkyl succinate synthase, wherein the alkyl succinate synthase is overexpressed;

b. an overexpressed succinyl-CoA:2-methyl-alkyl-succinyl-CoA transferase or 2-methyl-alkyl-succinyl-CoA synthetase that catalyzes the conversion of said 2-methyl-alkyl-succinate to a 2-methyl-alkyl-succinyl-CoA;

c. an overexpressed 2-methyl-alkyl-malonyl-CoA mutase that catalyzes the isomerization of said 2-methyl-alkyl-succinyl-CoA to a 2-methyl-alkyl-malonyl-CoA; and d. an overexpressed 2-methyl-alkyl-malonyl-CoA decarboxylase that catalyzes the decarboxylation of said 2-methyl-alkyl-malonyl-CoA to the acyl-CoA.

3. The method of claim 1, wherein said enzymes catalyzing the sequence of reactions for the oxygen-independent activation and conversion to the acyl-CoA and generation of the product precursor acetyl-CoA and the acyl-CoA or the keto-acid comprises:

a. the alkyl succinate synthase, wherein the alkyl succinate synthase is overexpressed;

b. an overexpressed 2-methyl-alkyl-succinyl-CoA synthetase that catalyzes the conversion of said 2-methyl-alkyl-succinate to a 2-methyl-alkyl-succinyl-CoA;

c. an overexpressed 2-methyl-alkyl-succinyl-CoA dehydrogenase that catalyzes the conversion of said 2-methyl-alkyl-succinyl-CoA to 2-methyl-alkyl-2-butenoyl-CoA;

d. an overexpressed mesaconyl-C1-CoA-C4-CoA transferase that catalyzes the conversion of said 2-methyl-alkyl-2-butenoyl-CoA to 3-methyl-alkyl-2-butenoyl-CoA;

e. an overexpressed mesaconyl-C4-CoA hydratase that catalyzes the conversion of said 3-methyl-alkyl-2-butenoyl-CoA to 3-methyl-alkyl-3-hydroxy-succinyl-CoA; and f. an overexpressed citramalyl-CoA lyase that catalyzes the conversion of said 3-methyl-alkyl-3-hydroxy-succinyl-CoA to the product precursor acetyl-CoA and the keto-acid.

4. The method of claim 1, wherein said enzymes catalyzing the sequence of reactions for the oxygen-independent activation and conversion to the acyl-CoA and generation of the product precursor acetyl-CoA and the acyl-CoA comprises:

a. the alkyl succinate synthase, wherein the alkyl succinate synthase is overexpressed;

b. an overexpressed succinyl-CoA:2-methyl-alkyl-succinyl-CoA transferase or 2-methyl-alkyl-succinyl-CoA synthetase that catalyzes the conversion of said 2-methyl-alkyl-succinate to a 2-methyl-alkyl-succinyl-CoA;

c. an overexpressed 2-methyl-alkyl-succinyl-CoA dehydrogenase that catalyzes the conversion of said 2-methyl-alkyl-succinyl-CoA to 2-methyl-alkyl-2-butenoyl-CoA;

d. an overexpressed mesaconyl-CoA hydratase/β-methylmalyl-CoA dehydratase that catalyzes the conversion of said 2-methyl-alkyl-2-butenoyl-CoA to 3-hydroxy-2-methyl-alkyl-succinyl-CoA;
e. an overexpressed β-methylmalyl-CoA lyase that catalyzes the conversion of said 3-hydroxy-2-methyl-alkyl-succinyl-CoA to glyoxylate and the acyl-CoA;
f. an overexpressed glyoxylate carboligase that catalyzes the conversion of said glyoxylate to tartronate semialdehyde;
g. an overexpressed tartronate semialdehyde reductase that catalyzes the conversion of said tartronate semialdehyde to D-glycerate;
h. an overexpressed glycerate kinase that catalyzes the conversion of said D-glycerate to 3-phospho-D-glycerate;
i. glycolytic enzymes that catalyze the conversion of said 3-phospho-D-glycerate to pyruvate, wherein the glycolytic enzymes are selected from the group consisting of phosphoglycerate mutase, enolase, and pyruvate kinase; and
j. a pyruvate formate lyase or pyruvate dehydrogenase that catalyze the conversion of said pyruvate to the acetyl-CoA.

5. The method of claim 1, wherein said enzymes catalyzing the sequence of reactions for the generation of the product precursor acetyl-CoA and the acyl-CoA comprises:
a. an overexpressed acyl-CoA dehydrogenase that catalyzes the conversion of said acyl-CoA to a transenoyl-CoA;
b. an overexpressed enoyl-CoA hydratase that catalyzes the hydration of said transenoyl-CoA to a 3-hydroxyacyl-CoA;
c. an overexpressed 3-hydroxyacyl-CoA dehydrogenase that catalyzes the oxidation of said 3-hydroxyacyl-CoA to a ß-ketoacyl-CoA; and
d. an overexpressed thiolase that catalyzes the cleavage of the acetyl-CoA from said ß-ketoacyl-CoA to produce the acetyl-CoA and an acyl-CoA 2-carbons shorter than said acyl-CoA in step a.

6. The method of claim 1, wherein said enzymes catalyzing the sequence of reactions for the regeneration of fumarate from the acyl-CoA or the keto-acid comprises:
a. an overexpressed propionyl-CoA carboxylase that catalyzes the carboxylation of propionyl-CoA to (S)-methyl-malonyl-CoA;
b. an overexpressed methyl-malonyl-CoA epimerase that catalyzes the interconversion of said (S)-methyl-malonyl-CoA to (R)-methyl-malonyl-CoA;
c. an overexpressed methyl-malonyl-CoA mutase that catalyzes the isomerization of said (R)-methyl-malonyl-CoA to succinyl-CoA;
d. an overexpressed succinyl-CoA:2-methyl-alkyl-succinyl-CoA transferase or succinyl-CoA synthetase that catalyzes the conversion of said succinyl-CoA to succinate; and
e. an overexpressed succinate dehydrogenase that catalyzes the conversion of said succinate to fumarate.

7. The method of claim 1, wherein said pathway for the regeneration of the fumarate from the acyl-CoA or the keto-acid comprises:
a. an overexpressed malate dehydrogenase for the conversion of said keto-acid to malate, wherein the keto-acid is pyruvate; and
b. an overexpressed fumarase for the dehydration of said malate to fumarate.

8. The method of claim 1, wherein said pathway for the regeneration of the fumarate from the acyl-CoA or the keto-acid comprises:
a. an overexpressed carboxylic acid omega hydroxylase that catalyzes the conversion of said keto-acid to an omega-hydroxy-2-keto-acid;
b. an overexpressed alcohol dehydrogenase that catalyzes the conversion of said omega-hydroxy-2-keto acid to an omega-oxo-2-keto-acid;
c. an overexpressed aldehyde dehydrogenase that catalyzes the conversion of said omega-oxo-2-keto-acid to a dicarboxylic 2-keto-acid;
d. an overexpressed ketoreductase or malate dehydrogenase that catalyzes the conversion of said dicarboxylic 2-keto-acid to malate; and
e. an overexpressed fumarase for the dehydration of said malate to fumarate.

9. The method of claim 1, wherein said alkyl succinate synthase is encoded by *Azoarcus* sp. HxN1 masB, *Azoarcus* sp. HxN1 masC, *Azoarcus* sp. HxN1 masD, *Azoarcus* sp. HxN1 masE, *Azoarcus* sp. HxN1 masG, *Desulfosarcina* sp. BuS5 A39W_RS0101550, *Desulfosarcina* sp. BuS5 A39W_RS0101545, *Desulfosarcina* sp. BuS5 A39W_RS0101540, *Desulfosarcina* sp. BuS5 A39W_RS0101535, *Desulfosarcina* sp. BuS5 A39W_RS19630, or *Desulfosarcina* sp. BuS5 A39W_RS0101580.

10. The method of claim 1, wherein said enzymes catalyzing the sequence of reactions for the generation of the product precursor acetyl-CoA comprises:
a. an overexpressed acyl-CoA dehydrogenase that catalyzes the conversion of said acyl-CoA to a transenoyl-CoA;
b. an overexpressed enoyl-CoA hydratase that catalyzes the hydration of said transenoyl-CoA to a 3-hydroxyacyl-CoA;
c. an overexpressed 3-hydroxyacyl-CoA dehydrogenase that catalyzes the oxidation of said 3-hydroxyacyl-CoA to a ß-ketoacyl-CoA; and
d. an overexpressed thiolase that catalyzes the cleavage of the acetyl-CoA from said ß-ketoacyl-CoA to produce the acetyl-CoA and an acyl-CoA 2-carbons shorter than said starting acyl-CoA in step a.

11. The method of claim 1, wherein the sequence of reactions for the formation of the product from the product precursor acetyl-CoA is selected:
a. a reverse beta oxidation (BOX-R) cycle comprised of:
i. an overexpressed thiolase that catalyzes the non-decarboxylative condensation of an acyl-CoA primer with a 2-carbon donor acetyl-CoA to produce a ß-ketoacyl-CoA;
ii. an overexpressed 3-oxoacyl-[acyl-carrier-protein] reductase or overexpressed 3-hydroxyacyl-CoA dehydrogenase that catalyzes the reduction of a ß-ketoacyl-CoA to a ß-hydroxyacyl-CoA;
iii. an overexpressed 3-hydroxyacyl-[acyl-carrier-protein] dehydratase or an overexpressed enoyl-CoA hydratase or 3-hydroxyacyl-CoA dehydratase that catalyzes the dehydration of a (3R)-ß-hydroxyacyl-CoA to a transenoyl-CoA;
iv. an overexpressed enoyl-[acyl-carrier-protein] reductase or acyl-CoA dehydrogenase or transenoyl-CoA reductase that catalyzes the reduction of said transenoyl-CoA to an acyl-CoA that is two carbons longer than said acyl-CoA primer; and v. an overexpressed termination pathway that catalyzes the conversion of an intermediate from said BOX-R cycle to said product; or b. a fatty acid biosynthesis (FAS) pathway comprised of:

i. an overexpressed acetyl-CoA carboxylase that catalyzes the conversion of acetyl-CoA to malonyl-CoA;

ii. an overexpressed malonyl-CoA-[acyl-carrier-protein] ("ACP") transacylase that catalyzes the conversion of said malonyl-CoA to malonyl-ACP;

iii. an overexpressed β-ketoacyl-ACP synthase that catalyzes the decarboxylative condensation of said malonyl-ACP with an acyl-ACP primer to produce a ß-ketoacyl-ACP;

iv. an overexpressed 3-oxoacyl-ACP reductase that catalyzes the reduction of said ß-ketoacyl-ACP to a ß-hydroxyacyl-ACP;

v. an overexpressed 3-hydroxyacyl-ACP dehydratase that catalyzes the dehydration of a (3R)-ß-hydroxyacyl-ACP to a transenoyl-ACP;

vi. an overexpressed enoyl-ACP reductase that catalyzes the reduction of a transenoyl-ACP to an acyl-ACP that is two carbons longer than said acyl-ACP primer; and vii. an overexpressed termination pathway that catalyzes the conversion of an intermediate from said FAS pathway to said product.

12. The method of claim 11, wherein said termination pathway is selected from the group consisting of:

a. a CoA cleaving thioesterase, an acyl-CoA:acetyl-CoA transferase, a phosphotransacylase and a carboxylate kinase, or an ACP cleaving thioesterase said product is selected from the group consisting of carboxylic acids, (3R)-β-hydroxy carboxylic acids, β-keto carboxylic acids, and α,β-unsaturated carboxylic acids;

b. an alcohol-forming coenzyme-A thioester reductase, an aldehyde-forming CoA thioester reductase and an alcohol dehydrogenase, an alcohol-forming ACP thioester reductase, or an aldehyde-forming ACP thioester reductase and an alcohol dehydrogenase and said product is selected from the group consisting of primary alcohols, 1,(3R)β diols, β-keto primary alcohols, and α,β-unsaturated primary alcohols;

c. an aldehyde-forming CoA or ACP thioester reductase and an aldehyde decarbonylase and said product is selected from the group consisting of linear alkanes, linear alkan-2-ols, linear methyl-ketones, and 1-alkenes; and d. an aldehyde-forming CoA or ACP thioester reductase and a transaminase and said product is selected from the group consisting of primary amines, 3-hydroxyamines, 3-keto-amines, and α,β-unsaturated primary amines.

13. The method of claim 1, wherein the terminal electron acceptor is $SO_4^{2-}$, $NO_3^-$, $Fe^{3+}$, $O_2$, or $Mn^{4+}$.

* * * * *

UNITED STATES PATENT AND TRADEMARK OFFICE
CERTIFICATE OF CORRECTION

| | |
|---|---|
| PATENT NO. | : 11,913,049 B2 |
| APPLICATION NO. | : 16/878032 |
| DATED | : February 27, 2024 |
| INVENTOR(S) | : Ramon Gonzalez, James M. Clomburg and Alexander Chou |

Page 1 of 1

It is certified that error appears in the above-identified patent and that said Letters Patent is hereby corrected as shown below:

On the Title Page

Item (71) Under Applicants: after "Ramon Gonzalez" delete "Friendswood, TX" and insert --Tampa, FL--; and delete "James Clomburg, Houston,TX (US); Alexander Chou, Houston,TX (US)".

In the Claims

Column 34, Claim 12, Line 14: please delete "1,(3R)β" and insert --1,(3R)-β--.

Signed and Sealed this
Thirtieth Day of April, 2024

Katherine Kelly Vidal
*Director of the United States Patent and Trademark Office*